US009822156B2

(12) United States Patent
Haque et al.

(10) Patent No.: US 9,822,156 B2
(45) Date of Patent: Nov. 21, 2017

(54) AMYLOID BETA EXPRESSION CONSTRUCTS AND USES THEREFOR

(71) Applicant: Whitehead Institute for Biomedical Research, Cambridge, MA (US)

(72) Inventors: Aftabul Haque, Belmont, MA (US); Susan L. Lindquist, Cambridge, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 14/738,016

(22) Filed: Jun. 12, 2015

(65) Prior Publication Data
US 2015/0361148 A1 Dec. 17, 2015

Related U.S. Application Data

(60) Provisional application No. 62/012,107, filed on Jun. 13, 2014.

(51) Int. Cl.
| | | |
|---|---|---|
| *C12N 15/81* | (2006.01) | |
| *C07K 14/47* | (2006.01) | |
| *C12N 15/85* | (2006.01) | |
| *G01N 33/50* | (2006.01) | |

(52) U.S. Cl.
CPC .......... *C07K 14/4711* (2013.01); *C12N 15/81* (2013.01); *C12N 15/85* (2013.01); *G01N 33/5014* (2013.01); *C07K 2319/02* (2013.01); *C12N 2740/16043* (2013.01); *C12N 2800/22* (2013.01); *C12N 2830/003* (2013.01); *C12N 2830/008* (2013.01); *G01N 2333/4709* (2013.01); *G01N 2500/10* (2013.01); *G01N 2800/2821* (2013.01)

(58) Field of Classification Search
None
See application file for complete search history.

(56) References Cited

U.S. PATENT DOCUMENTS

| | | |
|---|---|---|
| 7,029,909 B1 | 4/2006 | Uemura et al. |
| 8,263,558 B2 | 9/2012 | Holzman et al. |
| 2002/0068325 A1 | 6/2002 | Ng et al. |
| 2005/0227322 A1 | 10/2005 | Lindquist et al. |
| 2006/0141449 A1 | 6/2006 | Lindquist et al. |
| 2013/0045483 A1 | 2/2013 | Treusch et al. |

FOREIGN PATENT DOCUMENTS

| | | |
|---|---|---|
| CN | 101492674 | 7/2009 |
| JP | 4056248 | 3/2008 |
| WO | WO2008/084254 | 7/2008 |
| WO | WO2011088059 | 7/2011 |

OTHER PUBLICATIONS

Cereghino et al., Heterologous protein expression in the methylotrophic yeast *Pichia pastoris*, FEMS Micro. Rev., 24:45-66, (2000).
Chacinska et al., "Effects of beta-amyloid on proliferation and morphology of yeast *Saccharomyces cerevisiae*," *Letters in Peptide Science* (2002), 9(4-5):197-201.
Culvenor et al., "Subcellular localization of the Alzheimer's disease amyloid precursor protein and derived polypeptides expressed in a recombinant yeast system." Amyloid, 1998, 5(2):79-89. Abstract only.
Hines et al., "The expression and processing of human beta-amyloid peptide precursors in *Saccharomyces cerevisiae*: evidence for a novel endopeptidase in the yeast secretory system." Cell Mol. Biol. Res., 1994, 40(4):273-84. Abstract only.
Jung et al., "Increased viability of PC12 cells exposed to amyloid-b peptide by transduction with human TAT-methionine sulfoxide reductase." Neuroreport, 2003, 14(18):2349-2353.
Klein et al., "Selection for genes encoding secreted proteins and receptors," Proc. Natl Acad. Sci., USA, 93:7108-7113, (1996).
Lin-Cereghino The Effect of α-Mating Factor Secretion Signal Mutations on Recombinant Protein Expression in *Pichia pastoris*, Gene 519(2):311-317, (2013).
PCT International Search Report and Written Opinion in PCT Application No. PCT/US15/35571, dated Dec. 3, 2015, 12 pages.
Posas et al., "Osmotic Activation of the HOG MAPK Pathway via Ste11p MAPKKK: Scaffold Role of Pbs2p," Science, 276(5319):1702-1705, (1997).
pPICZalpha Vector, vector map, http://plasmid.med.harvard.edu/PlasmidRepository/file/map/ppiczalpha_abc.pdf, retrieved from internet on Jun. 27, 2014.
Shen et al., "Expression, purification and characterization of recombinant human beta-amyloid 1-42 in Pichia pastoris," *Protein Expression and Purification, Academic Press* (2009), 63(2):84-88.
Treusch et al., "Functional Links Between Aβ Toxicity, Endocytic Trafficking, and Alzheimer's Disease Risk Factors in Yeast," *Science* (2011), 334(6060):1241-1245.

*Primary Examiner* — Jim Ketter
(74) *Attorney, Agent, or Firm* — Fish & Richardson P.C.

(57) ABSTRACT

Disclosed are yeast expression constructs encoding a polypeptide containing a signal sequence, a Golgi-directing pro sequence, and a human amyloid beta protein, and mammalian expression constructs encoding a polypeptide containing a selected signal sequence and a human amyloid beta protein. Also disclosed are methods of screening cells to identify compounds that prevent or suppress amyloid beta-induced toxicity and genetic suppressors or enhancers of amyloid beta-induced toxicity. Compounds identified by such screens can be used to treat or prevent neurodegenerative disorders such as Alzheimer's disease.

36 Claims, 18 Drawing Sheets

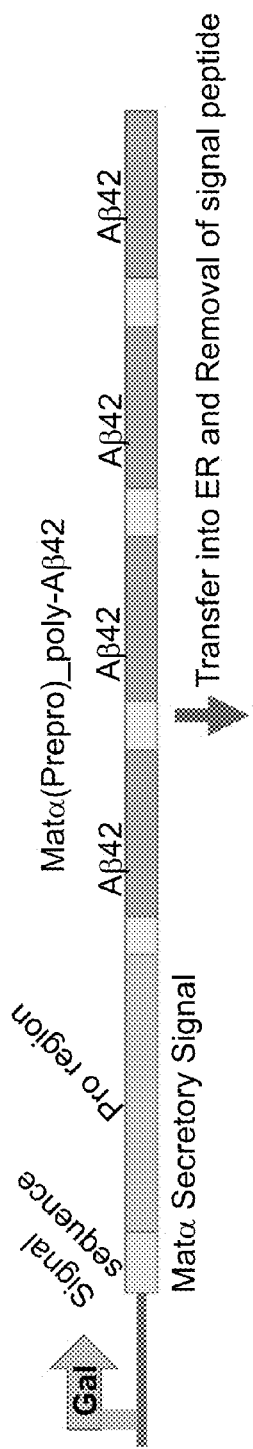
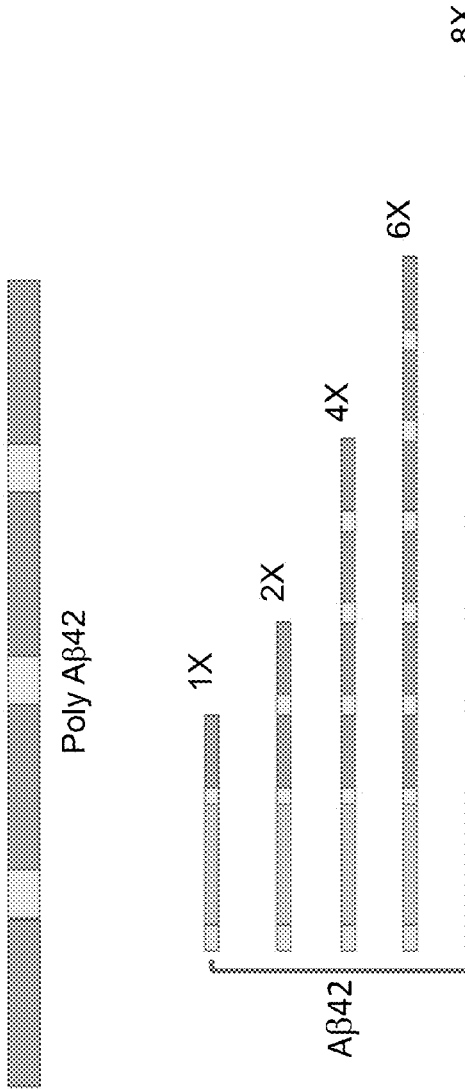
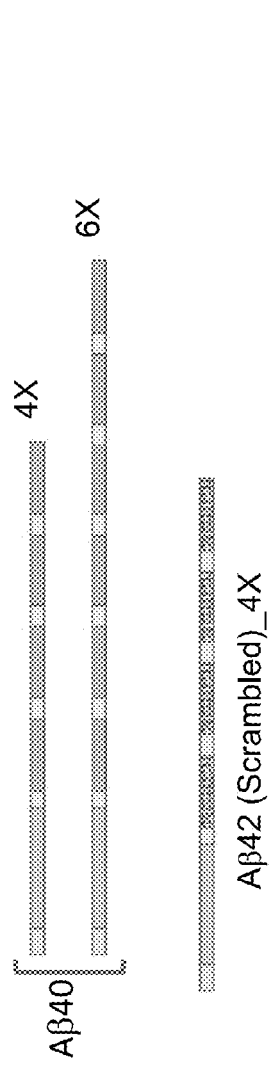
Fig. 1A
Fig. 1B

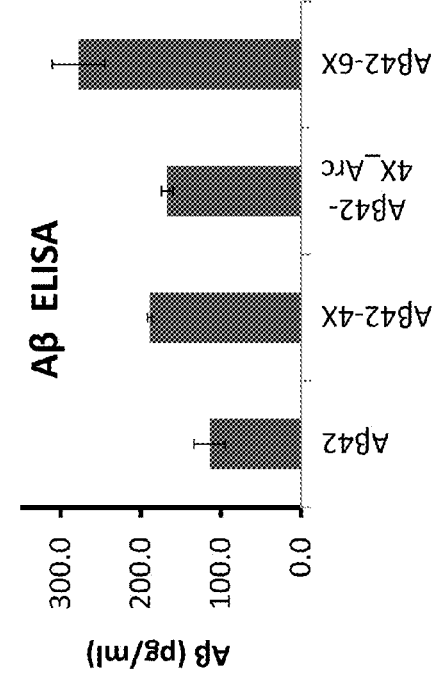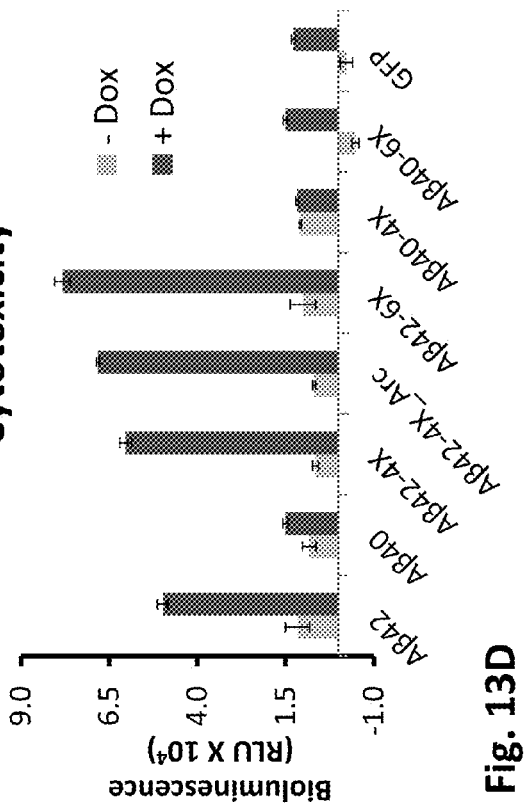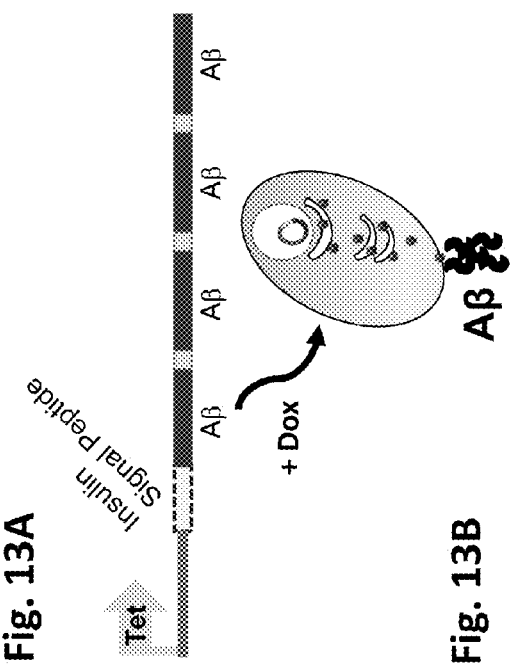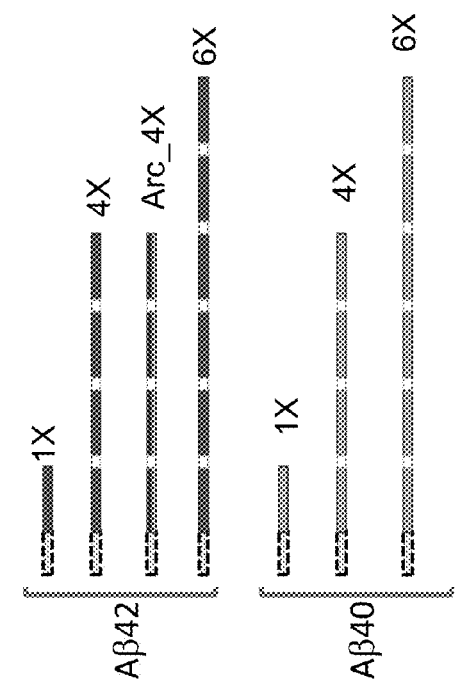

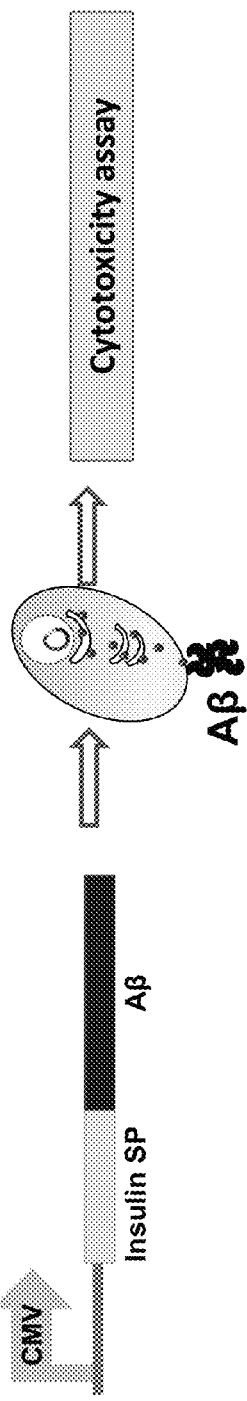
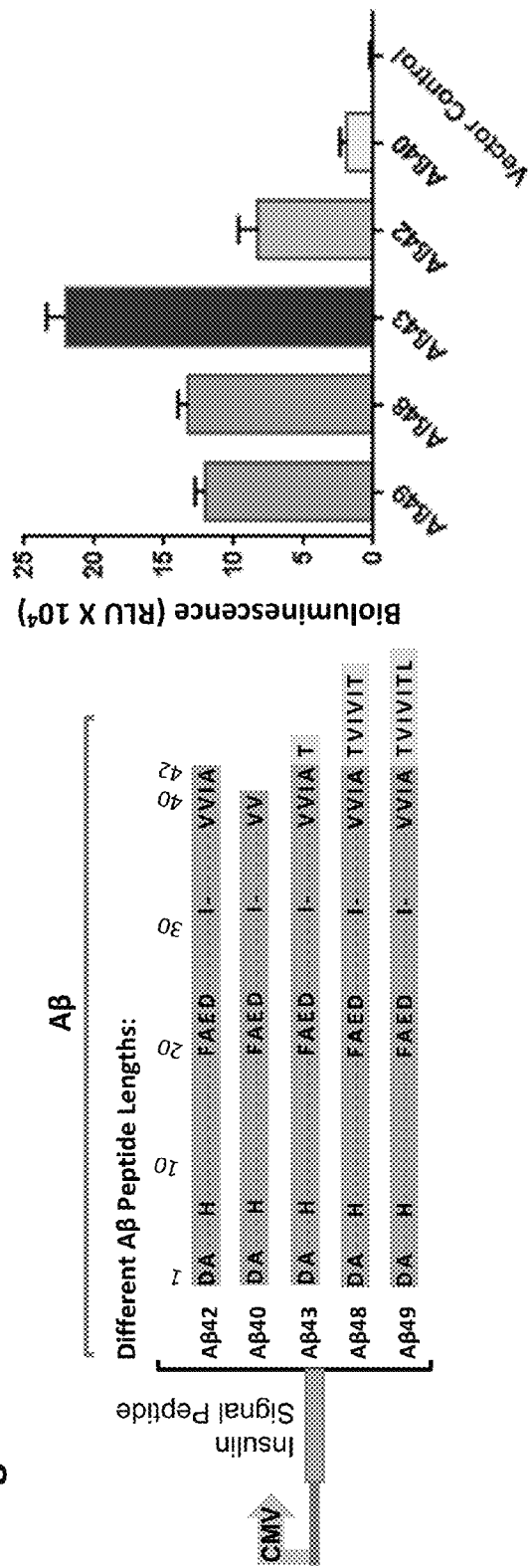
Fig. 17A
Fig. 17B
Fig. 17C

US 9,822,156 B2

AMYLOID BETA EXPRESSION CONSTRUCTS AND USES THEREFOR

TECHNICAL FIELD

The invention relates to protein chemistry and cellular and molecular biology.

BACKGROUND

Alzheimer's disease is a neurodegenerative disorder characterized by neurofibrillary tangles and plaques containing an amyloid beta peptide. Patients with Alzheimer's disease exhibit progressive dementia and personality dysfunction. Proteolytic cleavage of the amyloid precursor protein (APP) results in the generation of an amyloid beta peptide having a length ranging from 38 to 49 amino acids (e.g., 38-43 amino acids). The amyloid beta 1-42 peptide is particularly prone to self-aggregation and is strongly linked to development of Alzheimer's disease.

SUMMARY

The invention is based, at least in part, on the discovery that a yeast expression construct encoding a polypeptide containing a signal sequence, a Golgi-directing pro sequence, and a human amyloid beta protein can result in significant toxicity when expressed in yeast cells. The invention is also based, at least in part, on the discovery that a mammalian expression construct encoding a polypeptide containing a selected signal sequence and a human amyloid beta protein can result in significant toxicity when expressed in mammalian cells. This discovery permits the carrying out of screening assays using amyloid beta-expressing cells to identify compounds or genetic factors that modulate amyloid beta-induced toxicity. Compounds identified by such screens can be used for the treatment or prevention of neurodegenerative diseases such as Alzheimer's disease.

Described herein is an expression construct comprising a promoter operably linked to a nucleic acid encoding a polypeptide comprising a signal sequence, a Golgi-directing pro sequence, and a human amyloid beta protein.

Also provided herein is an expression construct comprising a promoter operably linked to a nucleic acid encoding a polypeptide comprising a signal sequence, a Golgi-directing pro sequence, and a polypeptide having the formula $[X-Y]_n$, wherein each X is, independently, absent or is a linker; each Y is, independently, a human amyloid beta peptide; and n is an integer between two and eight, inclusive.

A signal sequence causes the polypeptide containing it to be targeted to the endoplasmic reticulum within a cell. In some embodiments, the signal sequence is located at the amino terminus of the polypeptide encoded by the expression construct. The signal sequence can be identical to a naturally occurring signal sequence or can be an artificial (non-naturally occurring) signal sequence. In some embodiments, the signal sequence is identical to the signal sequence of a naturally occurring yeast protein. In some embodiments, the signal sequence is the yeast mating factor alpha signal sequence. In some embodiments, the signal sequence is the signal sequence of yeast killer toxin K1, secreted acid phosphatase, invertase or sucrase, or protoplast secreted protein 1 (Pst1).

A Golgi-directing pro sequence causes the transport of the polypeptide containing it to the Golgi. The Golgi-directing pro sequence can be identical to a naturally occurring Golgi-directing pro sequence or can be an artificial (non-naturally occurring) Golgi-directing pro sequence. In some embodiments, the Golgi-directing pro sequence is identical to the Golgi-directing pro sequence of a naturally occurring yeast protein. In some embodiments, the Golgi-directing pro sequence is the yeast mating factor alpha pro sequence. In some embodiments, the Golgi-directing pro sequence is the pro sequence of yeast KEX2, carboxypeptidase Y, Pep4, or Prb1.

The terms "human amyloid beta protein" and "human amyloid beta peptide," as used interchangeably herein, include proteins whose amino acid sequences are identical to naturally occurring wild type amyloid beta peptides as well as naturally occurring mutant amyloid beta peptides. Wild type amyloid beta peptides include amyloid beta 1-38 (Aβ38), amyloid beta 1-39 (Aβ39), amyloid beta 1-40 (Aβ40), amyloid beta 1-41 (Aβ41), amyloid beta 1-42 (Aβ42), amyloid beta 1-43 (Aβ43), amyloid beta 1-48 (Aβ48), and amyloid beta 1-49 (Aβ49). Amyloid beta mutations include A2T, A2V, H6R, D7N, E11K, F20E, A21G, E22G, E22Q, E22K, E22 deletion, D23N, I31E, E22G/I31E, A42T, and A42V. These mutations may optionally be present in any of the amyloid beta peptides 1-38, 1-39, 1-40, 1-41, 1-42, 1-43, 1-48, and 1-49.

In alternate embodiments, a variant of a human amyloid beta protein can be used. A "variant human amyloid beta protein" differs (via substitution, deletion, and/or insertion) from a naturally occurring amyloid beta peptide at up to 10 amino acids (e.g., differs at no more than 5 amino acids, differs at no more than 4 amino acids, differs at no more than 3 amino acids, differs at no more than 2 amino acids, or differs at 1 amino acid) and retains the ability to cause a decrease in growth or viability of a cell when expressed in a fusion polypeptide described herein.

An expression construct described herein can optionally be integrated in the genome of the yeast cell. For example, the expression construct can be an integrative plasmid such as pAG303, pAG304, pAG305, pAG306, pRS303, pRS304, pRS305, pRS306, or a derivative thereof.

An expression construct described herein can optionally be an episomal plasmid.

The promoter can be an inducible promoter such as GAL1-10, GAL1, GALL, GALS, GPD, ADH, TEF, CYC1, MRP7, MET25, TET, VP16, or VP16-ER. Alternatively, the promoter can be a constitutively active promoter.

In some embodiments, the polypeptide encoded by an expression construct described herein can include a plurality of human amyloid beta peptides. The polypeptide encoded by an expression construct described herein can optionally contain two, three, four, five, six, seven, eight, or more human amyloid beta peptides. In some embodiments, the polypeptide includes at least two human amyloid beta peptides. In some embodiments, the polypeptide includes at least four human amyloid beta peptides. In some embodiments, each of the human amyloid beta peptides has the same amino acid sequence. In other embodiments, the polypeptide includes at least two human amyloid beta peptides having different amino acid sequences.

The polypeptide encoded by an expression construct described herein can optionally comprise or consist of the amino acid sequence of SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, or SEQ ID NO:101.

Also disclosed is a yeast cell comprising an expression construct described herein, wherein expression of the nucleic acid and production of the polypeptide in the cell results in a decrease in growth or viability of the cell. In some embodiments, expression of the nucleic acid and production of the polypeptide renders the cell non-viable.

A yeast cell can have one or more (e.g., at least two, at least three, or at least four) copies (e.g., integrated or episomal copies) of an expression construct.

In some embodiments, the yeast is *Saccharomyces cerevisiae*, *Saccharomyces uvae*, *Saccharomyces kluyveri*, *Schizosaccharomyces pombe*, *Kluyveromyces lactis*, *Hansenula polymorpha*, *Pichia pastoris*, *Pichia methanolica*, *Pichia kluyveri*, *Yarrowia lipolytica*, *Candida* sp., *Candida utilis*, *Candida cacaoi*, *Geotrichum* sp., or *Geotrichum fermentans*.

In some embodiments, at least one gene that encodes a protein involved in drug efflux or cell permeability is disrupted in the yeast cell. For example, one or more of the genes PDR1, PDR3, PDR5, SNQ2, or ERG6 can be disrupted in the yeast cell.

Also disclosed is an expression construct comprising a promoter operably linked to a nucleic acid encoding a polypeptide comprising a signal sequence and a human amyloid beta protein, wherein the signal sequence is an insulin signal sequence (e.g., the human insulin signal sequence) or a trypsin signal sequence (e.g., the human trypsin signal sequence). In some embodiments, the human amyloid beta protein is fused directly to the signal sequence.

The invention further provides an expression construct comprising a promoter operably linked to a nucleic acid encoding a polypeptide comprising a signal sequence and a polypeptide having the formula $[X-Y]_n$, wherein each X is, independently, absent or is a linker; each Y is, independently, a human amyloid beta peptide; and n is an integer between two and eight, inclusive, wherein the signal sequence is an insulin signal sequence (e.g., the human insulin signal sequence) or a trypsin signal sequence (e.g., the human trypsin signal sequence).

The polypeptide encoded by an expression construct described herein can optionally comprise or consist of the amino acid sequence of SEQ ID NO:93, SEQ ID NO:95, or SEQ ID NO:103.

In some embodiments, the expression construct is a plasmid or viral vector.

Also disclosed is a mammalian cell comprising an expression construct comprising a promoter operably linked to a nucleic acid encoding a polypeptide comprising a signal sequence and a human amyloid beta protein, wherein the signal sequence is an insulin signal sequence (e.g., the human insulin signal sequence) or a trypsin signal sequence (e.g., the human trypsin signal sequence), wherein expression of the nucleic acid and production of the polypeptide in the cell results in a decrease in growth or viability of the cell. In some embodiments, expression of the nucleic acid and production of the polypeptide renders the cell non-viable. In some embodiments, the cell is a neuronal cell. In some embodiments, the cell is a 293T cell.

Also disclosed is a method of inducing toxicity in a cell by: providing a yeast or mammalian cell described herein; and allowing a level of inductive or constitutive expression of the nucleic acid in the cell that is toxic to the cell.

Also disclosed is a method of identifying a compound that prevents or suppresses amyloid beta-induced toxicity by: culturing a yeast or mammalian cell described herein in the presence of a candidate agent and under conditions that allow for expression of the nucleic acid at a level that, in the absence of the candidate agent, is sufficient to induce toxicity in the cell; measuring cell growth or viability in the presence of the candidate agent; and comparing cell growth or viability measured in the presence of the candidate agent to cell growth or viability in the absence of the candidate agent, wherein if cell growth or viability is increased in the presence of the candidate agent as compared to in the absence of the candidate agent, then the candidate agent is identified as a compound that prevents or suppresses amyloid beta-induced toxicity.

Also disclosed is a method of identifying a genetic suppressor or enhancer of amyloid beta-induced toxicity by: providing a yeast or mammalian cell described herein, wherein the cell has been genetically modified to overexpress a gene; culturing the cell under conditions that allow for expression of the protein at a level that, in the absence of overexpression of the gene, is sufficient to induce toxicity in the cell; measuring cell growth or viability in the presence of overexpression of the gene; and comparing cell growth or viability measured in the presence of overexpression of the gene to cell growth or viability in the absence of overexpression of the gene, wherein (i) if cell growth or viability is increased in the presence of overexpression of the gene as compared to in the absence of overexpression of the gene, then the gene is identified as a genetic suppressor of amyloid beta-induced toxicity, and (ii) if cell growth or viability is decreased in the presence of overexpression of the gene as compared to in the absence of overexpression of the gene, then the gene is identified as a genetic enhancer of amyloid beta-induced toxicity.

Also disclosed is a method of identifying a genetic suppressor or enhancer of amyloid beta-induced toxicity by: providing a yeast or mammalian cell described herein, wherein an endogenous gene of the cell has been disrupted; culturing the cell under conditions that allow for expression of the protein at a level that, in the absence of disruption of the endogenous gene, is sufficient to induce toxicity in the cell; measuring cell growth or viability in the presence of disruption of the endogenous gene; and comparing cell growth or viability measured in the presence of disruption of the endogenous gene to cell growth or viability in the absence of disruption of the endogenous gene, wherein (i) if cell growth or viability is increased in the presence of disruption of the endogenous gene as compared to in the absence of disruption of the endogenous gene, then the gene is identified as a genetic enhancer of amyloid beta-induced toxicity, and (ii) if cell growth or viability is decreased in the presence of disruption of the endogenous gene as compared to in the absence of disruption of the endogenous gene, then the gene is identified as a genetic suppressor of amyloid beta-induced toxicity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present application, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 1A depicts the yeast Aβ42 expression construct "Matα-Aβ42_4X", which contains four copies of Aβ42 in a single construct.

FIG. 1B depicts yeast expression constructs containing varying numbers of copies of Aβ42 or Aβ40.

FIG. 13A-13D show that poly-Aβ42 expression causes cytotoxicity in mammalian cells. FIG. 13A depicts a doxycycline-inducible poly-Aβ42 expression construct containing the signal sequence of human insulin (Ins). FIG. 13B depicts mammalian poly-A13 expression constructs. FIG. 13C is a graph depicting the cytotoxic effect of the indicated poly-Aβ expression construct upon doxycycline-induced expression in 293T cells. FIG. 13D is a graph depicting the amount of Aβ42 present in the cell supernatant of 293T cells 96 hours post-induction.

FIG. 17A-17C depicts a comparison of Aβ43-mediated toxicity to toxicity caused by other naturally-occurring Aβ peptide fragments in mammalian cells (293T). FIG. 17A shows a CMV promoter driven expression system for Aβ peptide in mammalian models and a cytotoxic end-point measurement. FIG. 17B depicts mammalian expression constructs for different Aβ peptides (various residues of amyloid beta peptides including SEQ ID NOS 1, 104, and 105). FIG. 17C is a graph depicting cytotoxicity in 293T cells caused by expression of the indicated Aβ peptides.

DETAILED DESCRIPTION

Figure 2:
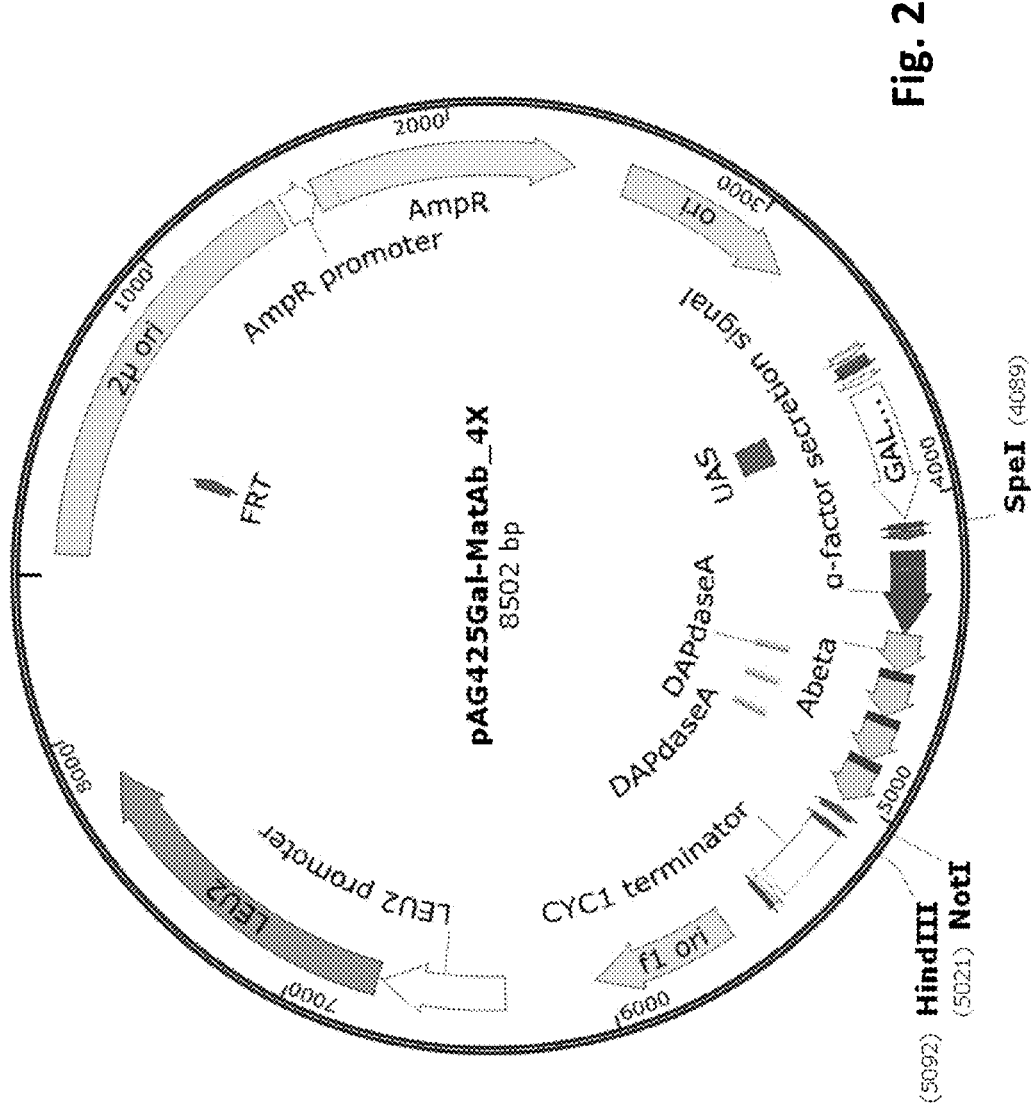
FIG. 2 depicts the map of the "pAG425Gal-MatAβ_4X" expression vector.

The expression constructs and amyloid beta-expressing cells described herein can be used to identify compounds or genetic factors that modulate amyloid beta-induced toxicity. Compounds identified by such screens can be used for the treatment or prevention of neurodegenerative diseases such as Alzheimer's disease.

Proteins and Nucleic Acids

Described herein are compositions and methods for identifying candidate compounds that prevent or suppress amyloid beta-induced toxicity and genetic suppressors or enhancers of amyloid beta-induced toxicity. A yeast expression construct used in the compositions and methods described herein contains a signal sequence, a Golgi-directing pro sequence, and a human amyloid beta protein (i.e., a human amyloid beta peptide). A mammalian expression construct used in the compositions and methods described herein contains a selected signal sequence and a human amyloid beta protein.

The invention provides a nucleic acid encoding a polypeptide comprising a signal sequence, a Golgi-directing pro sequence, and a polypeptide having the formula $[X-Y]_n$, wherein each X is, independently, absent or is a linker; each Y is, independently, a human amyloid beta peptide; and n is an integer between two and twenty, inclusive.

The invention further provides a nucleic acid encoding a polypeptide comprising a signal sequence and a polypeptide having the formula [X-Y]$_n$, wherein each X is, independently, absent or is a linker; each Y is, independently, a human amyloid beta peptide; and n is an integer between two and twenty, inclusive, wherein the signal sequence is an insulin signal sequence (e.g., the human insulin signal sequence) or a trypsin signal sequence (e.g., the human trypsin signal sequence).

"Human amyloid beta" refers to an amino acid sequence identical to human amyloid beta peptide that is derived through proteolytic processing of the human amyloid precursor protein (APP) and is associated with amyloid pathologies. The term amyloid beta (Aβ) includes naturally occurring wild type amyloid beta peptides as well as naturally occurring mutant amyloid beta peptides. The term "human amyloid beta protein" as used herein encompasses proteins produced synthetically by recombinant methods. Wild type amyloid beta peptides include Aβ38, Aβ39, Aβ40, Aβ41, Aβ42, Aβ43, Aβ48, and Aβ49, wherein the number next to Aβ denotes the length of the peptide defined by the number of amino acids after proteolytic processing from the amyloid precursor protein. Amyloid beta mutations include A2T, A2V, H6R (English), D7N (Tottori), E11K (Leuven), F20E, A21G (Flemish), E22G (Arctic), E22Q (Dutch), E22K (Italian), E22 deletion, D23N (Iowa), I31E, E22G/I31E, A42T, and A42V. In these mutations the first letter represents the naturally occurring amino acid, the middle number represents the position of the amino acid in the context of the Aβ peptide (1-42) and the last letter following the numbered position represents the amino acid to which the wild type peptide is mutated. The mutation "E22 deletion" represents an Aβ peptide where amino acid glutamic acid (E) at position 22 is deleted and E22G/I31E represents Aβ peptide in which both amino acids glutamic acid (E) and isoleucine (I) are replaced by glycine (G) and glutamic acid (E), respectively. These mutations may be present in any of the naturally occurring amyloid beta peptides Aβ38, Aβ39, Aβ40, Aβ41, Aβ42, Aβ43, Aβ48, and Aβ49, or their synthetic derivatives.

Amino acids 1-43 of human amyloid beta, which amino acids are used as the backbone of the amyloid beta peptides described herein, are as follows: DAEFRHDSGYEVHHQKLVFFAEDVGSNKGAIIGLMVGGVVIAT (SEQ ID NO:1). In other embodiments, amino acids 1-48 of human amyloid beta are used as the backbone of amyloid beta peptides described herein. Amino acids 1-48 of human amyloid beta are as follows: DAEFRHDSGYEVHHQKLVFFAEDVGSNKGAIIGLMVGGVVIATVIVIT (SEQ ID NO:104). In yet other embodiments, amino acids 1-49 of human amyloid beta are used as the backbone of amyloid beta peptides described herein. Amino acids 1-49 of human amyloid beta are as follows: DAEFRHDSGYEVHHQKLVFFAEDVGSNKGAIIGLMVGGVVIATVIVITL (SEQ ID NO:105).

As used herein, the term "signal sequence" refers to a peptide sequence that is present within a polypeptide and causes the polypeptide to be targeted to the endoplasmic reticulum within a cell. Exemplary signal sequences described in the working examples are the yeast mating factor alpha signal sequence (for a yeast expression construct) and the human insulin and human trypsin signal sequences (for mammalian expression constructs). Examples of additional signal sequences that can be used in a yeast expression construct include the signal sequences of killer toxin K1, secreted acid phosphatase, invertase (sucrase), and Pst1. Examples of additional signal sequences that can be used in a mammalian expression construct include the signal sequences of human serum albumin, orexin, human preproparathyroid hormone, somatostatin, shadoo, brain-derived neurotrophic factor, neuropeptide Y, vasoactive intestinal peptide, enkephalin, cholecystokinin, neurotensin, pro-thyrotropin-releasing hormone, neuropeptide W, somatoliberin, and somatotropin. Signal sequences are reviewed in e.g., Wilkinson et al. (1997) J Membr Biol. 155(3):189-97, Haguenauer-Tsapis (1992) Mol Microbiol. 6(5):573-9, and Pool (2005) Mol Membr Biol. 22(1-2):3-15.

A polypeptide containing a signal sequence and a human amyloid beta protein may optionally contain one or more heterologous sequences. The heterologous sequence of the fusion protein can optionally be a linker, an immunoglobulin element, a dimerizing domain, a targeting domain, a stabilizing domain, or a purification domain. Alternatively, an amyloid beta protein can be fused with a heterologous sequence such as a detection protein. Exemplary detection proteins include: a fluorescent protein such as green fluorescent protein (GFP), cyan fluorescent protein (CFP) or yellow fluorescent protein (YFP); an enzyme such as β-galactosidase or alkaline phosphatase (AP); and an epitope such as glutathione-S-transferase (GST) or hemagglutinin (HA). To illustrate, an amyloid beta protein can be fused to GFP at the N- or C-terminus or other parts of the amyloid beta protein. These fusion proteins provide methods for rapid and easy detection and identification of the amyloid beta protein in the recombinant yeast cell.

The term "linker," as used herein, refers to a sequence of amino acids linking two polypeptide moieties. Exemplary, non-limiting functions of a linker can include introduction of a flexible component or space-creating region between two protein domains, introduction of proteolytic processing sites (e.g., proteolytic cleavage sites), or creation of an affinity tag. A linker may be any suitable length, for example, a linker may include 1, 2, 3, 4, 5, 6, 7, 8, 9, 10, 11, 12, 13, 14, 15, 16, 17, 18, 19, 20, 30, 40, 50, or more amino acids. In some embodiments, a linker is a spacer peptide as described herein. In some embodiments, the spacer peptide is from the yeast mating factor alpha 1 gene. For example, in some embodiments, a linker may include an amino acid sequence selected from SEQ ID NOs:44-49 or a fragment thereof.

In some embodiments, a polypeptide containing a signal sequence and a human amyloid beta peptide may include a plurality of human amyloid beta peptides. In some embodiments, a polypeptide containing a signal sequence, a Golgi-directing pro sequence, and a human amyloid beta peptide may include a plurality of human amyloid beta peptides. The polypeptide encoded by an expression construct described herein can optionally contain two, three, four, five, six, seven, eight, nine, ten, eleven, twelve, thirteen, fourteen, fifteen, twenty, or more human amyloid beta peptides. In some embodiments, the polypeptide includes at least two human amyloid beta peptides. In some embodiments, the polypeptide includes at least four human amyloid beta peptides. In some embodiments, each of the human amyloid beta peptides includes the same amino acid sequence. For instance, in some embodiments, each of the human amyloid beta peptides is Aβ42. In other embodiments, the polypeptide includes at least two human amyloid beta peptides having different amino acid sequences. For instance, in some embodiments, the polypeptide includes Aβ42 and Aβ43.

Also described herein are methods of preparing and transferring nucleic acids encoding an amyloid beta protein into a cell so that the cell expresses the amyloid beta protein. The term "amyloid beta nucleic acid" encompasses a nucleic acid containing a sequence encoding any of the amyloid beta proteins described herein. Exemplary amyloid beta nucleic acids include those encoding Aβ42 or Aβ43.

The term "nucleic acid" generally refers to at least one molecule or strand of DNA, RNA or a derivative or mimic thereof, containing at least one nucleobase, for example, a naturally occurring purine or pyrimidine base found in DNA or RNA. Generally, the term "nucleic acid" refers to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule.

The working examples describe the use of several exemplary yeast expression constructs. The following are several additional exemplary yeast expression constructs.

Matα-Aβ42_4X_NC (Not Cleaved, Prepro and 4 copies of Aβ are linked) Nucleotide Sequence
(SEQ ID NO: 2)
GTCGACTGGATCCACAAGTTTGTACAAAAAAGCAGGCTGGTACCAAAAGA

ATGAGATTCCCATCTATTTTCACCGCTGTTTTGTTTGCTGCTTCTTCTGC

TTTGGCTGCTCCAGTTAACACTACTACTGAAGATGAAACTGCTCAAATTC

CAGCTGAAGCTGTTATTGGTTACTTGGATTTGGAAGGTGATTTCGATGTT

GCTGTTTTGCCATTCTCTAACTCTACCAACAATGGTTTGTTGTTCATCAA

CACCACCATTGCTTCTATTGCTGCTAAAGAAGAAGGTGTTTCTTTGGACG

GTTCTGCTGGTTCTGGTGATGCAGAATTCAGACATGATTCTGGTTACGAA

GTTCACCACCAAAAGTTGGTTTTTTCGCTGAAGATGTCGGTTCTAACAA

GGGTGCTATTATTGGTTTGATGGTTGGTGGTGTAGTTATTGCTGGTTCAG

CAGGTTCAGCTGGTAGTGACGCCGAATTCAGACACGATAGTGGTTATGAA

GTCCATCATCAAAAATTAGTTTTCTTTGCCGAAGATGTTGGTAGTAACAA

AGGTGCAATCATCGGTTTAATGGTCGGTGGTGTCGTAATAGCAGGTAGTG

CAGGTTCCGCCGGTTCTGATGCCGAATTCAGACACGACTCCGGTTATGAA

GTACATCACCAAAAGTTGGTATTCTTCGCAGAAGATGTAGGTTCAAACAA

AGGTGCCATAATAGGTTTAATGGTTGGTGGTGTCGTTATCGCAGGTTCTG

CCGGTAGTGCTGGTTCAGACGCAGAATTCAGACATGACAGTGGTTACGAA

GTACACCATCAAAAATTAGTCTTTTCGCAGAAGATGTTGGTAGTAACAA

GGGTGCTATAATAGGTTTGATGGTCGGTGGTGTAGTCATAGCTTAAACCC

AGCTTTCTTGTACAAAGTGGTGCGGCCGCACTCGAG

Matα-Aβ42_4X_NC (Not Cleaved, Prepro and 4 copies of Aβ are linked) Amino Acid Sequence
(SEQ ID NO: 3)
MRFPSIFTAVLFAASSALAAPVNTTTEDETAQIPAEAVIGYLDLEGDFDV

AVLPFSNSTNNGLLFINTTIASIAAKEEGVSLDGSAGSGDAEFRHDSGYE

VHHQKLVFFAEDVGSNKGAIIGLMVGGVVIAGSAGSAGSDAEFRHDSGYE

VHHQKLVFFAEDVGSNKGAIIGLMVGGVVIAGSAGSAGSDAEFRHDSGYE

VHHQKLVFFAEDVGSNKGAIIGLMVGGVVIAGSAGSAGSDAEFRHDSGYE

VHHQKLVFFAEDVGSNKGAIIGLMVGGVVIA

Matα-Aβ42_4X_Clinked (prepro cleaved, Aβ linked) Nucleotide Sequence
(SEQ ID NO: 4)
GTCGACTGGATCCACAAGTTTGTACAAAAAAGCAGGCTGGTACCAAAAGA

ATGAGATTCCCATCTATTTTCACCGCTGTTTTGTTTGCTGCTTCTTCTGC

TTTGGCTGCTCCAGTTAACACTACTACTGAAGATGAAACTGCTCAAATTC

CAGCTGAAGCTGTTATTGGTTACTTGGATTTGGAAGGTGATTTCGATGTT

GCTGTTTTGCCATTCTCTAACTCTACCAACAATGGTTTGTTGTTCATCAA

CACCACCATTGCTTCTATTGCTGCTAAAGAAGAAGGTGTCTCTTTGGATA

AGAGAGAAGCTGAAGCAGACGCAGAATTCAGACATGATTCTGGTTATGAA

GTTCACCACCAAAAGTTGGTTTTCTTCGCTGAAGATGTTGGTTCTAACAA

GGGTGCTATTATCGGTTTGATGGTTGGTGGTGTAGTTATTGCTGGTTCTG

CAGGTTCAGCTGGTTCAGATGCCGAATTCAGACACGATAGTGGTTACGAA

GTACATCATCAAAAATTAGTCTTTTTTGCCGAAGATGTCGGTAGTAACAA

AGGTGCAATCATTGGTTTAATGGTCGGTGGTGTCGTAATAGCAGGTAGTG

CCGGTTCTGCTGGTAGTGATGCAGAATTCAGACACGACTCCGGTTACGAA

GTCCATCACCAAAAGTTGGTATTCTTTGCCGAAGATGTCGGTTCAAACAA

GGGTGCCATAATAGGTTTAATGGTTGGTGGTGTCGTTATCGCCGGTAGTG

CTGGTAGTGCAGGTTCCGACGCCGAATTCAGACATGACTCAGGTTACGAA

GTACACCATCAAAAGTTGGTATTTTTCGCAGAAGATGTAGGTTCCAACAA

AGGTGCAATCATAGGTTTGATGGTTGGTGGTGTCGTAATTGCCTAAACCC

AGCTTTCTTGTACAAAGTGGTGCGGCCGCACTCGAG

Matα-Aβ42_4X_Clinked (prepro cleaved, Aβ linked) Amino Acid Sequence
(SEQ ID NO: 5)
MRFPSIFTAVLFAASSALAAPVNTTTEDETAQIPAEAVIGYLDLEGDFDV

AVLPFSNSTNNGLLFINTTIASIAAKEEGVSLDKREAEADAEFRHDSGYE

VHHQKLVFFAEDVGSNKGAIIGLMVGGVVIAGSAGSAGSDAEFRHDSGYE

VHHQKLVFFAEDVGSNKGAIIGLMVGGVVIAGSAGSAGSDAEFRHDSGYE

VHHQKLVFFAEDVGSNKGAIIGLMVGGVVIAGSAGSAGSDAEFRHDSGYE

VHHQKLVFFAEDVGSNKGAIIGLMVGGVVIA

Matα-Aβ42_4X_Clinked2 Nucleotide Sequence
(SEQ ID NO: 6)
GTCGACTGGATCCACAAGTTTGTACAAAAAAGCAGGCTGGTACCAAAAGA

ATGAGATTCCCATCTATTTTCACCGCTGTTTTGTTTGCTGCTTCTTCTGC

TTTGGCTGCTCCAGTTAACACTACTACTGAAGATGAAACTGCTCAAATTC

CAGCTGAAGCTGTTATTGGTTACTTGGATTTGGAAGGTGATTTCGATGTT

GCTGTTTTGCCATTCTCTAACTCTACCAACAATGGTTTGTTGTTCATCAA

CACCACCATTGCTTCTATTGCTGCTAAAGAAGAAGGTGTCTCTTTGGATA

AGAGAGAAGCTGAAGCAGACGCAGAATTCAGACATGATTCTGGTTATGAA

GTTCACCACCAAAAGTTGGTTTTCTTCGCTGAAGATGTTGGTTCTAACAA

GGGTGCTATTATCGGTTTGATGGTTGGTGGTGTAGTTATTGCTGGTTCTG

CAGGTTCAGCTGGTTCAGATGCCGAATTCAGACACGATAGTGGTTACGAA

GTACATCATCAAAAATTAGTCTTTTTTGCCGAAGATGTCGGTAGTAACAA

```
AGGTGCAATCATTGGTTTAATGGTCGGTGGTGTCGTAATCGCTAAAAGAG
AAGCCGACGCTGAAGCTGATGCCGAATTCAGACATGACTCAGGTTACGAA
GTCCATCACCAAAAGTTGGTATTCTTTGCCGAAGATGTCGGTTCAAACAA
GGGTGCCATAATAGGTTTAATGGTTGGTGGTGTCGTTATAGCAGGTAGTG
CTGGTTCCGCTGGTAGTGATGCAGAATTCAGACATGACAGTGGTTATGAA
GTCCACCATCAAAAATTGGTCTTTTTCGCAGAAGATGTAGGTTCCAACAA
AGGTGCAATCATAGGTTTGATGGTTGGTGGTGTCGTAATTGCCTAAACCC
AGCTTTCTTGTACAAAGTGGTGCGGCCGCACTCGAG
```

Matα-Aβ42_4X_Clinked2 Amino Acid Sequence
(SEQ ID NO: 7)
```
MRFPSIFTAVLFAASSALAAPVNTTTEDETAQIPAEAVIGYLDLEGDFDV
AVLPFSNSTNNGLLFINTTIASIAAKEEGVSLDKREAEADAEFRHDSGYE
VHHQKLVFFAEDVGSNKGAIIGLMVGGVVIAGSAGSAGSDAEFRHDSGYE
VHHQKLVFFAEDVGSNKGAIIGLMVGGVVIAKREADAEAEFRHDSGYE
VHHQKLVFFAEDVGSNKGAIIGLMVGGVVIAGSAGSAGSDAEFRHDSGYE
VHHQKLVFFAEDVGSNKGAIIGLMVGGVVIA
```

Matα-Aβ40_1X Nucleotide Sequence
(SEQ ID NO: 8)
```
GTCGACTGGATCCACAAGTTTGTACAAAAAAGCAGGCTGGTACCAAAGA
ATGAGATTTCCTTCAATTTTTACTGCAGTTTTATTCGCAGCATCCTCCGC
ATTAGCTGCTCCAGTCAACACTACAACAGAAGATGAAACGGCACAAATTC
CGGCTGAAGCTGTCATCGGTTACTTAGATTTAGAAGGGGATTTCGATGTT
GCTGTTTTGCCATTTTCCAACAGCACAAATAACGGGTTATTGTTTATAAA
TACTACTATTGCCAGCATTGCTGCTAAAGAAGAAGGGGTATCTTTGGATA
AAAGAGAGGCTGAAGCTGATGCTGAATTTAGACATGATTCTGGTTATGAA
GTTCATCATCAAAAATTGGTTTTTTTTGCTGAAGATGTTGGTTCTAATAA
AGGTGCTATTATTGGTTTGATGGTTGGTGGTGTTGTCTAAACCCAGCTTT
CTTGTACAAAGTGGTGCGGCCGCACTCGAG
```

Matα-Aβ40_1X Amino Acid Sequence
(SEQ ID NO: 9)
```
MRFPSIFTAVLFAASSALAAPVNTTTEDETAQIPAEAVIGYLDLEGDFDV
AVLPFSNSTNNGLLFINTTIASIAAKEEGVSLDKREAEADAEFRHDSGYE
VHHQKLVFFAEDVGSNKGAIIGLMVGGVV
```

Matα-Aβ40_2X Nucleotide Sequence
(SEQ ID NO: 10)
```
GTCGACTGGATCCACAAGTTTGTACAAAAAAGCAGGCTGGTACCAAAGA
ATGAGATTCCCATCTATTTTCACCGCTGTTTTGTTTGCTGCTTCTTCTGC
TTTGGCTGCTCCAGTTAACACTACTACTGAAGATGAAACTGCTCAAATTC
CAGCTGAAGCTGTTATTGGTTACTTGGATTTGGAAGGTGATTTCGATGTT
GCTGTTTTGCCATTCTCTAACTCTACCAACAATGGTTTGTTGTTCATCAA
CACCACCATTGCTTCTATTGCTGCTAAAGAAGAAGGTGTCTCTTTGGATA
AGAGAGAAGCTGAAGCAGACGCAGAATTCAGACATGATTCTGGTTATGAA
GTTCACCACCAAAAGTTGGTTTTCTTCGCTGAAGATGTTGGTTCTAACAA
GGGTGCTATTATCGGTTTGATGGTTGGTGGTGTAGTAAAAAGAGAAGCCG
AAGCTGAAGCTGATGCCGAATTCAGACATGACACGATAGTGGTTACGAAGTACAT
CATCAAAAATTAGTCTTTTTTGCCGAAGATGTCGGTAGTAACAAAGGTGC
AATCATTGGTTTAATGGTCGGTGGTGTCGTTTGAACCCAGCTTTCTTGTA
CAAAGTGGTGCGGCCGCACTCGAG
```

Matα-Aβ40_2X Amino Acid Sequence
(SEQ ID NO: 11)
```
MRFPSIFTAVLFAASSALAAPVNTTTEDETAQIPAEAVIGYLDLEGDFDV
AVLPFSNSTNNGLLFINTTIASIAAKEEGVSLDKREAEADAEFRHDSGYE
VHHQKLVFFAEDVGSNKGAIIGLMVGGVVKREAEAEADAEFRHDSGYEVH
HQKLVFFAEDVGSNKGAIIGLMVGGVV
```

Matα-Aβ42_2X-Aβ40_2X Nucleotide Sequence
(SEQ ID NO: 12)
```
GTCGACTGGATCCACAAGTTTGTACAAAAAAGCAGGCTGGTACCAAAGA
ATGAGATTCCCATCTATTTTCACCGCTGTTTTGTTTGCTGCTTCTTCTGC
TTTGGCTGCTCCAGTTAACACTACTACTGAAGATGAAACTGCTCAAATTC
CAGCTGAAGCTGTTATTGGTTACTTGGATTTGGAAGGTGATTTCGATGTT
GCTGTTTTGCCATTCTCTAACTCTACCAACAATGGTTTGTTGTTCATCAA
CACCACCATTGCTTCTATTGCTGCTAAAGAAGAAGGTGTCTCTTTGGATA
AGAGAGAAGCTGAAGCAGACGCAGAATTCAGACATGATTCTGGTTATGAA
GTTCACCACCAAAAGTTGGTTTTCTTCGCTGAAGATGTTGGTTCTAACAA
GGGTGCTATTATCGGTTTGATGGTTGGTGGTGTAGTTATTGCTAAAAGAG
AAGCCGAAGCTGAAGCTGATGCCGAATTCAGACACGATAGTGGTTACGAA
GTACATCATCAAAAATTAGTCTTTTTTGCCGAAGATGTCGGTAGTAACAA
AGGTGCAATCATTGGTTTAATGGTCGGTGGTGTCGTAATAGCCAAGAGAG
AAGCAGACGCCGAAGCCGATGCAGAATTCAGACACGACTCCGGTTACGAA
GTCCATCACCAAAAGTTGGTATTCTTTGCCGAAGATGTCGGTTCAAACAA
GGGTGCCATAATAGGTTTAATGGTTGGTGGTGTCGTTAAGAGAAGCTG
ACGCTGAAGCAGACGCCGAATTCAGACACGACTCAGGTTATGAAGTACAC
CATCAAAAATTGGTATTTTTCGCAGAAGATGTTGGTTCCAACAAAGGTGC
CATTATTGGTTTGATGGTTGGTGGTGTCGTTTAAACCCAGCTTTCTTGTA
CAAAGTGGTGCGGCCGCACTCGAG
```

Matα-Aβ42_2X-Aβ40_2X Amino Acid Sequence
(SEQ ID NO: 13)
```
MRFPSIFTAVLFAASSALAAPVNTTTEDETAQIPAEAVIGYLDLEGDFDV
AVLPFSNSTNNGLLFINTTIASIAAKEEGVSLDKREAEADAEFRHDSGYE
VHHQKLVFFAEDVGSNKGAIIGLMVGGVVIAKREAEAEADAEFRHDSGYE
VHHQKLVFFAEDVGSNKGAIIGLMVGGVVIAKREADAEAEFRHDSGYE
VHHQKLVFFAEDVGSNKGAIIGLMVGGVVKREADAEAEFRHDSGYEVH
HQKLVFFAEDVGSNKGAIIGLMVGGVV
```

Matα-Aβ42_2X-Aβ40scr_2X, Nucleotide Sequence
(SEQ ID NO: 14)
```
GTCGACTGGATCCACAAGTTTGTACAAAAAAGCAGGCTGGTACCAAAGA
ATGAGATTCCCATCTATTTTCACCGCTGTTTTGTTTGCTGCTTCTTCTGC
TTTGGCTGCTCCAGTTAACACTACTACTGAAGATGAAACTGCTCAAATTC
CAGCTGAAGCTGTTATTGGTTACTTGGATTTGGAAGGTGATTTCGATGTT
```

```
GCTGTTTTGCCATTCTCTAACTCTACCAACAATGGTTTGTTGTTCATCAA

CACCACCATTGCTTCTATTGCTGCTAAAGAAGAAGGTGTCTCTTTGGATA

AGAGAGAAGCTGAAGCAGACGCAGAATTCAGACATGATTCTGGTTATGAA

GTTCACCACCAAAAGTTGGTTTTCTTCGCTGAAGATGTTGGTTCTAACAA

GGGTGCTATTATCGGTTTGATGGTTGGTGGTGTAGTTATTGCTAAAAGAG

AAGCCGAAGCTGAAGCTGATGCCGAATTCAGACACGATAGTGGTTACGAA

GTACATCATCAAAAATTAGTCTTTTTTGCCGAAGATGTCGGTAGTAACAA

AGGTGCAATCATTGGTTTAATGGTCGGTGGTGTCGTAATAGCCAAGAGAG

AAGCAGACGCCGAAGCTGCTATTGCTGAAGGTGATTCACATGTTTTGAAA

GAAGGTGCCTACATGGAAATCTTCGATGTTCAAGGTCATGTTTTCGGTGG

TAAGATCTTCAGAGTTGTTGATTTGGGTTCCCACAACAAAAGAGAAGCTG

ACGCAGAAGCCGCAATAGCCGAAGGTGACTCTCACGTCTTAAAAGAAGGT

GCTTATATGGAAATTTTTGACGTCCAAGGTCACGTCTTTGGTGGTAAGAT

TTTTAGAGTAGTCGACTTGGGTAGTCATAACTAAACCCAGCTTTCTTGTA

CAAAGTGGTGCGGCCGCACTCGAG
```

Matα-Aβ42_2X-Aβ40scr_2X, Amino Acid Sequence
(SEQ ID NO: 15)
MRFPSIFTAVLFAASSALAAPVNTTTEDETAQIPAEAVIGYLDLEGDFDV

AVLPFSNSTNNGLLFINTTIASIAAKEEGVSLDKREAEADAEFRHDSGYE

VHHQKLVFFAEDVGSNKGAIIGLMVGGVVIAKREAEAEADAEFRHDSGYE

VHHQKLVFFAEDVGSNKGAIIGLMVGGVVIAKREADAEAAIAEGDSHVLK

EGAYMEIFDVQGHVFGGKIFRVVDLGSHNKREADAEAAIAEGDSHVLKEG

AYMEIFDVQGHVFGGKIFRVVDLGSHN

The working examples describe the use of several exemplary mammalian expression constructs. The following are several additional exemplary mammalian expression constructs.

Ins-Aβ42_Arc_1X Nucleotide Sequence
(SEQ ID NO: 16)
```
CACCATGGCCCTGTGGATGCGCCTCCTGCCCCTGCTGGCGCTGCTGGCCC

TCTGGGGACCTGACCCAGCCGCAGCCGATGCGGAATTTCGCCATGATTCT

GGCTATGAAGTGCATCATCAGAAACTGGTGTTTTTTGCGGGAGATGTGGG

CTCTAACAAAGGCGCGATTATTGGCCTGATGGTGGGCGGCGTGGTGATTG

CGTAA
```

Ins-Aβ42_Arc_1X Amino Acid Sequence
(SEQ ID NO: 17)
MALWMRLLPLLALLALWGPDPAAADAEFRHDSGYEVHHQKLVFFAGDV

GSNKGAIIGLMVGGVVIA

Ins-Aβ42_F20E_1X Nucleotide Sequence
(SEQ ID NO: 18)
```
CACCATGGCCCTGTGGATGCGCCTCCTGCCCCTGCTGGCGCTGCTGGCCC

TCTGGGGACCTGACCCAGCCGCAGCCGATGCGGAATTTCGCCATGATTCT

GGCTATGAAGTGCATCATCAGAAACTGGTGTTTGAGGCGGAAGATGTGGG

CTCTAACAAAGGCGCGATTATTGGCCTGATGGTGGGCGGCGTGGTGATTG

CGTAA
```

Ins-Aβ42_F20E_1X Amino Acid Sequence
(SEQ ID NO: 19)
MALWMRLLPLLALLALWGPDPAAADAEFRHDSGYEVHHQKLVFEAEDV

GSNKGAIIGLMVGGVVIA

Ins-Aβ42_I31E_1X Nucleotide Sequence
(SEQ ID NO: 20)
```
CACCATGGCCCTGTGGATGCGCCTCCTGCCCCTGCTGGCGCTGCTGGCCC

TCTGGGGACCTGACCCAGCCGCAGCCGATGCGGAATTTCGCCATGATTCT

GGCTATGAAGTGCATCATCAGAAACTGGTGTTTTTTGCGGAAGATGTGGG

CTCTAACAAAGGCGCGGAGATTGGCCTGATGGTGGGCGGCGTGGTGATTG

CGTAA
```

Ins-Aβ42_I31E_1X Amino Acid Sequence
(SEQ ID NO: 21)
MALWMRLLPLLALLALWGPDPAAADAEFRHDSGYEVHHQKLVFFAEDVG

SNKGAEIGLMVGGVVIA

Ins-Aβ42_Arc_I31E_1X Nucleotide Sequence
(SEQ ID NO: 22)
```
CACCATGGCCCTGTGGATGCGCCTCCTGCCCCTGCTGGCGCTGCTGGCCC

TCTGGGGACCTGACCCAGCCGCAGCCGATGCGGAATTTCGCCATGATTCT

GGCTATGAAGTGCATCATCAGAAACTGGTGTTTTTTGCGGGAGATGTGGG

CTCTAACAAAGGCGCGGAGATTGGCCTGATGGTGGGCGGCGTGGTGATTG

CGTAA
```

Ins-Aβ42_Arc_I31E_1X Amino Acid Sequence
(SEQ ID NO: 23)
MALWMRLLPLLALLALWGPDPAAADAEFRHDSGYEVHHQKLVFFAGDV

GSNKGAEIGLMVGGVVIA

Tryp-Aβ40_1X Nucleotide Sequence
(SEQ ID NO: 24)
```
CACCATGTCTGCACTTCTGATCCTAGCTCTTGTTGGAGCTGCAGTTGCTG

ATGCGGAATTTCGCCATGATTCTGGCTATGAAGTGCATCATCAGAAACTG

GTGTTTTTTGCGGAAGATGTGGGCTCTAACAAAGGCGCGATTATTGGCCT

GATGGTGGGCGGCGTGGTGTAA
```

Tryp-Aβ40_1X Amino Acid Sequence
(SEQ ID NO: 25)
MSALLILALVGAAVADAEFRHDSGYEVHHQKLVFFAEDVGSNKGAIIGLM

VGGVV

SEAP-Aβ40_1X Nucleotide Sequence
(SEQ ID NO: 26)
```
CACCATGCTGCTGCTGCTGCTGCTGCTGGGCCTGAGGCTACAGCTCTCCC

TGGGCGATGCGGAATTTCGCCATGATTCTGGCTATGAAGTGCATCATCAG

AAACTGGTGTTTTTTGCGGAAGATGTGGGCTCTAACAAAGGCGCGATTAT

TGGCCTGATGGTGGGCGGCGTGGTGTAA
```

SEAP-Aβ40_1X Amino Acid Sequence
(SEQ ID NO: 27)
MLLLLLLLGLRLQLSLGDAEFRHDSGYEVHHQKLVFFAEDVGSNKGAIIG

LMVGGVV mLuc-Aβ40_1X Amino Acid Sequence
(SEQ ID NO: 28)
```
CACCATGGACATCAAGGTGGTGTTCACCCTGGTGTTCAGCGCCCTGGTGC

AGGCCGATGCGGAATTTCGCCATGATTCTGGCTATGAAGTGCATCATCAG
``` mLuc-Aβ40_1X Amino Acid Sequence
(SEQ ID NO: 29)
MDIKVVFTLVFSALVQADAEFRHDSGYEVHHQKLVFFAEDVGSNKGAIIG
LMVGGVV APP-Aβ40_1X Nucleotide Sequence
(SEQ ID NO: 30)
CACCATGCTGCCCGGTTTGGCACTGCTCCTGCTGGCCGCCTGGACGGCTC
GGGCGGATGCGGAATTTCGCCATGATTCTGGCTATGAAGTGCATCATCAG
AAACTGGTGTTTTTTGCGGAAGATGTGGGCTCTAACAAAGGCGCGATTAT
TGGCCTGATGGTGGGCGGCGTGGTGTAA APP-Aβ40_1X Amino Acid Sequence
(SEQ ID NO: 31)
MLPGLALLLLAAWTARADAEFRHDSGYEVHHQKLVFFAEDVGSNKGAIIG
LMVGGVV NSP-Aβ40_1X Nucleotide Sequence
(SEQ ID NO: 32)
CACCATGGATGCGGAATTTCGCCATGATTCTGGCTATGAAGTGCATCATC
AGAAACTGGTGTTTTTTGCGGAAGATGTGGGCTCTAACAAAGGCGCGATT
ATTGGCCTGATGGTGGGCGGCGTGGTGTAA NSP-Aβ40_1X Amino Acid Sequence
(SEQ ID NO: 33)
MDAEFRHDSGYEVHHQKLVFFAEDVGSNKGAIIGLMVGGVV Ins-Aβ42_4X Nucleotide Sequence
(SEQ ID NO: 34)
CACCATGGCCCTGTGGATGAGACTGCTGCCCCTGCTGGCTCTGCTGGCAC
TGTGGGGACCTGATCCTGCCGCCGCTGATGCCGAGTTCAGACACGATAGC
GGCTACGAGGTGCACCACCAGAAACTGGTGTTCTTCGCCGAGGACGTGGG
CAGCAACAAGGGCGCCATCATCGGCCTGATGGTGGGAGGCGTCGTGATCG
CCAGAAGGGACGCCGAGTTTAGGCACGACTCTGGATATGAAGTGCATCAT
CAGAAACTGGTGTTTTTTGCTGAAGATGTGGGGTCCAACAAAGGGGCCAT
TATTGGACTGATGGTGGGCGGAGTCGTGATTGCTAAGCGCGACGCCGAAT
TCCGGCACGATTCCGGCTACGAAGTGCACCATCAGAAACTGGTGTTTTTC
GCAGAGGATGTGGGCTCTAACAAGGGGCTATCATCGGACTGATGGTGGG
CGGGGTCGTGATCGCTCGGAGAGATGCCGAGTTCCGGCATGACAGCGGAT
ATGAAGTGCACCACCAGAAACTGGTGTTTTTTGCCGAGGATGTGGGAAGT
AACAAAGGGCAATCATTGGCCTGATGGTGGGAGGGGTCGTGATTGCCTG
A Ins-Aβ42_4X Amino Acid Sequence
(SEQ ID NO: 35)
MALWMRLLPLLALLALWGPDPAAADAEFRHDSGYEVHHQKLVFFAEDVGS
NKGAIIGLMVGGVVIARRDAEFRHDSGYEVHHQKLVFFAEDVGSNKGAII
GLMVGGVVIAKRDAEFRHDSGYEVHHQKLVFFAEDVGSNKGAIIGLMVGG
VVIARRDAEFRHDSGYEVHHQKLVFFAGDVGSNKGAIIGLMVGGVVIA Ins-Aβ42_Arc_4X Nucleotide Sequence
(SEQ ID NO: 36)
CACCATGGCCCTGTGGATGAGACTGCTGCCCCTGCTGGCTCTGCTGGCAC
TGTGGGGACCTGATCCTGCCGCCGCTGATGCCGAGTTCAGACACGATAGC
GGCTACGAGGTGCACCACCAGAAACTGGTGTTCTTTGCCGGCGACGTGGG
CAGCAACAAGGGCGCCATCATCGGCCTGATGGTGGGAGGCGTCGTGATCG
CCAGAAGGGACGCCGAGTTTAGGCACGACTCTGGATATGAAGTGCATCAT
CAGAAACTGGTGTTTTTCGCTGGGGATGTGGGGTCCAACAAAGGGGCCAT
TATTGGACTGATGGTGGGCGGAGTCGTGATTGCTAAGCGCGACGCCGAAT
TCCGGCACGATTCCGGCTACGAAGTGCACCATCAGAAACTGGTGTTCTTC
GCCGGGGACGTGGGATCTAACAAGGGGGCTATCATTGGGCTGATGGTGGG
AGGGGTCGTGATTGCTCGGCGGGATGCTGAGTTCCGGCATGACAGCGGAT
ATGAGGTGCACCATCAGAAACTGGTGTTTTTTGCCGGGGACGTGGGCTCA
AACAAAGGCGCAATTATCGGGCTGATGGTGGGCGGGGTCGTGATCGCTTA
A Ins-Aβ42_Arc_4X Amino Acid Sequence
(SEQ ID NO: 37)
MALWMRLLPLLALLALWGPDPAAADAEFRHDSGYEVHHQKLVFFAGDVGS
NKGAIIGLMVGGVVIARRDAEFRHDSGYEVHHQKLVFFAGDVGSNKGAII
GLMVGGVVIAKRDAEFRHDSGYEVHHQKLVFFAGDVGSNKGAIIGLMVGG
VVIARRDAEFRHDSGYEVHHQKLVFFAGDVGSNKGAIIGLMVGGVVIA Ins-Aβ42_6X Nucleotide Sequence
(SEQ ID NO: 38)
CACCATGGCCCTGTGGATGAGACTGCTGCCCCTGCTGGCTCTGCTGGCAC
TGTGGGGACCTGATCCTGCCGCCGCTGATGCCGAGTTCAGACACGATAGC
GGCTACGAGGTGCACCACCAGAAACTGGTGTTCTTCGCCGAGGACGTGGG
CAGCAACAAGGGCGCCATCATCGGCCTGATGGTGGGAGGCGTCGTGATCG
CCAGAAGGGACGCCGAGTTTAGGCACGACTCTGGATATGAAGTGCATCAT
CAGAAACTGGTGTTTTTTGCTGAAGATGTGGGGTCCAACAAAGGGGCCAT
TATTGGACTGATGGTGGGCGGAGTCGTGATTGCTAAGCGCGACGCCGAAT
TCCGGCACGATTCCGGCTACGAAGTGCACCATCAGAAACTGGTGTTTTTC
GCAGAGGATGTGGGCTCTAACAAGGGGCTATCATCGGACTGATGGTGGG
CGGGGTCGTGATCGCTCGGAGAGATGCCGAGTTCCGGCATGACAGCGGAT
ATGAAGTGCACCACCAGAAACTGGTGTTTTTTGCCGAGGATGTGGGAAGT
AACAAAGGGCAATCATTGGCCTGATGGTGGGAGGGGTCGTGATTGCTAA
ACGGGATGCTGAGTTCCGCCACGACTCAGGCTATGAGGTGCACCATCAGA
AACTGGTGTTCTTTGCCGAAGATGTGGGATCTAACAAGGGCGCAATTATT
GGGCTGATGGTGGGCGGCGTCGTGATCGCAAGACGGGATGCAGAATTCAG
ACATGACTCCGGATACGAGGTGCACCATCAGAAACTGGTGTTTTTTGCTG
AGGACGTGGGGAGCAACAAAGGGCTATTATCGGGCTGATGGTGGGAGGC
GTCGTGATTGCCTGA -continued Ins-Aβ42_6X Amino Acid Sequence
(SEQ ID NO: 39)
MALWMRLLPLLALLALWGPDPAAADAEFRHDSGYEVHHQKLVFFAEDVGS

NKGAIIGLMVGGVVIARRDAEFRHDSGYEVHHQKLVFFAEDVGSNKGAII

GLMVGGVVIAKRDAEFRHDSGYEVHHQKLVFFAEDVGSNKGAIIGLMVGG

VVIARRDAEFRHDSGYEVHHQKLVFFAEDVGSNKGAIIGLMVGGVVIAKR

DAEFRHDSGYEVHHQKLVFFAEDVGSNKGAIIGLMVGGVVIARRDAEFRH

DSGYEVHHQKLVFFAEDVGSNKGAIIGLMVGGVVIA

Ins-Aβ40_4X Nucleotide Sequence
(SEQ ID NO: 40)
CACCATGGCCCTGTGGATGAGACTGCTGCCCCTGCTGGCTCTGCTGGCAC

TGTGGGGACCTGATCCTGCCGCCGCTGATGCCGAGTTCAGACACGATAGC

GGCTACGAGGTGCACCACCAGAAACTGGTGTTCTTCGCCGAGGACGTGGG

CAGCAACAAGGGCGCCATCATCGGCCTGATGGTGGGAGGCGTCGTGCGGA

GAGATGCCGAATTCCGGCACGACTCCGGATATGAAGTGCATCATCAGAAA

CTGGTGTTTTTTGCTGAAGATGTGGGGTCCAACAAAGGGGCCATTATTGG

ACTGATGGTGGGCGGAGTCGTGAAGCGGGACGCCGAGTTTAGGCATGACT

CTGGCTACGAAGTGCACCATCAGAAACTGGTGTTTTTCGCAGAGGATGTG

GGCTCTAACAAGGGGGCTATCATCGGACTGATGGTGGGCGGGGTCGTGCG

CAGAGATGCTGAGTTTAGACACGATTCTGGATATGAAGTGCACCACCAGA

AACTGGTGTTTTTTGCCGAGGATGTGGGAAGTAACAAAGGGGCAATCATT

GGCCTGATGGTGGGAGGGGTGGTGTAA

Ins-Aβ40_4X Amino Acid Sequence
(SEQ ID NO: 41)
MALWMRLLPLLALLALWGPDPAAADAEFRHDSGYEVHHQKLVFFAEDVGS

NKGAIIGLMVGGVVRRDAEFRHDSGYEVHHQKLVFFAEDVGSNKGAIIGL

MVGGVVKRDAEFRHDSGYEVHHQKLVFFAEDVGSNKGAIIGLMVGGVVRR

DAEFRHDSGYEVHHQKLVFFAEDVGSNKGAIIGLMVGGVV

Ins-Aβ40_6X Nucleotide Sequence
(SEQ ID NO: 42)
CACCATGGCCCTGTGGATGAGACTGCTGCCCCTGCTGGCTCTGCTGGCAC

TGTGGGGACCTGATCCTGCCGCCGCTGATGCCGAGTTCAGACACGATAGC

GGCTACGAGGTGCACCACCAGAAACTGGTGTTCTTCGCCGAGGACGTGGG

CAGCAACAAGGGCGCCATCATCGGCCTGATGGTGGGAGGCGTCGTGCGGA

GAGATGCCGAATTCCGGCACGACTCCGGATATGAAGTGCATCATCAGAAA

CTGGTGTTTTTTGCTGAAGATGTGGGGTCCAACAAAGGGGCCATTATTGG

ACTGATGGTGGGCGGAGTCGTGAAGCGGGACGCCGAGTTTAGGCATGACT

CTGGCTACGAAGTGCACCATCAGAAACTGGTGTTTTTCGCAGAGGATGTG

GGCTCTAACAAGGGGGCTATCATCGGACTGATGGTGGGCGGGGTCGTGCG

CAGAGATGCTGAGTTTAGACACGATTCTGGATATGAAGTGCACCACCAGA

AACTGGTGTTTTTTGCCGAGGATGTGGGAAGTAACAAAGGGGCAATCATT

GGCCTGATGGTGGGAGGGGTCGTGAAAAGGGATGCAGAGTTTCGGCACGA

CAGTGGCTATGAAGTGCATCACCAGAAACTGGTGTTCTTCGCAGAAGATG

TGGGGAGTAACAAGGGCGCTATTATCGGGCTGATGGTGGGCGGAGTCGTG

CGGAGGGACGCTGAGTTCCGCCATGACAGCGGATATGAGGTGCACCATCA

GAAACTGGTGTTCTTTGCCGAAGATGTGGGATCAAACAAGGGCGCAATCA

TTGGGCTGATGGTGGGCGGCGTGGTGTAA

Ins-Aβ40_6X Amino Acid Sequence
(SEQ ID NO: 43)
MALWMRLLPLLALLALWGPDPAAADAEFRHDSGYEVHHQKLVFFAEDVGS

NKGAIIGLMVGGVVRRDAEFRHDSGYEVHHQKLVFFAEDVGSNKGAIIGL

MVGGVVKRDAEFRHDSGYEVHHQKLVFFAEDVGSNKGAIIGLMVGGVVRR

DAEFRHDSGYEVHHQKLVFFAEDVGSNKGAIIGLMVGGVVKRDAEFRHDS

GYEVHHQKLVFFAEDVGSNKGAIIGLMVGGVVRRDAEFRHDSGYEVHHQK

LVFFAEDVGSNKGAIIGLMVGGVV

Yeast Expression Constructs, Cells, and Screening Assays

Yeast strains that can be used in the compositions and methods described herein include, but are not limited to, *Saccharomyces cerevisiae, Saccharomyces uvae, Saccharomyces kluyveri, Schizosaccharomyces pombe, Kluyveromyces lactis, Hansenula polymorpha, Pichia pastoris, Pichia methanolica, Pichia kluyveri, Yarrowia lipolytica, Candida* sp., *Candida utilis, Candida cacaoi, Geotrichum* sp., and *Geotrichum fermentans*. Although much of the discussion herein relates to *Saccharomyces cerevisiae* which ectopically expresses an abnormally processed protein, this is merely for illustrative purposes. Other yeast strains can be substituted for *S. cerevisiae*.

Certain aspects of the disclosure relate to screening methods for identifying candidate therapeutic agents (e.g., pharmaceutical, chemical, or genetic agents). The methods described herein can optionally be carried out in yeast strains bearing mutations in the ERG6 gene, the PDR1 gene, the PDR3 gene, the PDR5 gene, the SNQ2 gene, and/or any other gene which affects membrane efflux pumps and/or increases permeability for drugs.

A nucleic acid encoding a polypeptide described herein may be transfected into a yeast cell using nucleic acid vectors that include, but are not limited to, plasmids, linear nucleic acid molecules, artificial chromosomes, and episomal vectors.

Three well known systems used for recombinant plasmid expression and replication in yeast cells include integrative plasmids, low-copy-number ARS-CEN plasmids, and high-copy-number 2μ plasmids. See Sikorski, "Extrachromosomal cloning vectors of *Saccharomyces cerevisiae*," in Plasmid, A Practical Approach, Ed. K. G. Hardy, IRL Press, 1993; and Yeast Cloning Vectors and Genes, Current Protocols in Molecular Biology, Section II, Unit 13.4, Eds., Ausubel et al., 1994.

An example of the integrative plasmids is YIp, which is maintained at one copy per haploid genome, and is inherited in Mendelian fashion. Such a plasmid, containing a gene of interest, a bacterial origin of replication and a selectable gene (typically an antibiotic-resistance marker), is produced in bacteria. The purified vector is linearized within the selectable gene and used to transform competent yeast cells.

An example of the low-copy-number ARS-CEN plasmids is YCp, which contains the autonomous replicating sequence (ARS1) and a centromeric sequence (CEN4). These plasmids are usually present at 1-2 copies per cell. Removal of the CEN sequence yields a YRp plasmid, which is typically present in 100-200 copies per cell. However, this plasmid is both mitotically and meiotically unstable.

An example of the high-copy-number 2μ plasmids is YEp, which contains a sequence approximately 1 kb in length (named the 2μ sequence). The 2μ sequence acts as a yeast replicon giving rise to higher plasmid copy number. However, these plasmids are unstable and require selection for maintenance. Copy number is increased by having on the plasmid a selection gene operatively linked to a crippled promoter.

A wide variety of plasmids can be used in the compositions and methods described herein. In one embodiment, the plasmid is an integrative plasmid (e.g., pAG303, pAG304, pAG305, pAG306, pRS303, pRS304, pRS305, pRS306, or a derivative thereof). See, e.g., Alberti et al. (2007) "A suite of Gateway cloning vectors for high-throughput genetic analysis in *Saccharomyces cerevisiae*" Yeast 24(10):913-19. In further embodiments, the plasmid is an episomal plasmid (e.g., p426GPD, p416GPD, p426TEF, p423GPD, p425GPD, p424GPD or p426GAL).

Regardless of the type of plasmid used, yeast cells are typically transformed by chemical methods (e.g., as described by Rose et al., 1990, Methods in Yeast Genetics, Cold Spring Harbor Laboratory Press, Cold Spring Harbor, N.Y.). The cells are typically treated with lithium acetate to achieve transformation efficiencies of approximately $10^4$ colony-forming units (transformed cells)/μg of DNA. Yeast perform homologous recombination such that the cut, selectable marker recombines with the mutated (usually a point mutation or a small deletion) host gene to restore function. Transformed cells are then isolated on selective media. Of course, any suitable means of introducing nucleic acids into yeast cells can be used.

The yeast vectors (plasmids) described herein typically contain a yeast origin of replication, an antibiotic resistance gene, a bacterial origin of replication (for propagation in bacterial cells), multiple cloning sites, and a yeast nutritional gene for maintenance in yeast cells. The nutritional gene (or "auxotrophic marker") is most often one of the following: 1) TRP1 (Phosphoribosylanthranilate isomerase); 2) URA3 (Orotidine-5'-phosphate decarboxylase); 3) LEU2 (3-Isopropylmalate dehydrogenase); 4) HIS3 (Imidazoleglycerol-phosphate dehydratase or IGP dehydratase); or 5) LYS2 (α-aminoadipate-semialdehyde dehydrogenase).

The yeast vectors (plasmids) described herein may also contain promoter sequences. A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively linked" and "operatively positioned" mean that a promoter is in a correct functional location and/or orientation in relation to a nucleic acid sequence to control transcriptional initiation and/or expression of that sequence.

A promoter may be one naturally associated with a nucleic acid sequence, as may be obtained by isolating the 5' non-coding sequences located upstream of the coding segment and/or exon. Such a promoter can be referred to as "endogenous." Alternatively, a promoter may be a recombinant or heterologous promoter, which refers to a promoter that is not normally associated with a nucleic acid sequence in its natural environment. Such promoters may include promoters of other genes and promoters not "naturally occurring." The promoters employed may be either constitutive or inducible.

For example, various yeast-specific promoters (elements) may be employed to regulate the expression of a RNA in yeast cells. Examples of inducible yeast promoters include GAL1-10, GAL1, GALL, GALS, TET, VP16 and VP16-ER. Examples of repressible yeast promoters include Met25. Examples of constitutive yeast promoters include glyceraldehyde 3-phosphate dehydrogenase promoter (GPD), alcohol dehydrogenase promoter (ADH), translation-elongation factor-1-alpha promoter (TEF), cytochrome c-oxidase promoter (CYC1), and MRP7. Autonomously replicating expression vectors of yeast containing promoters inducible by glucocorticoid hormones have also been described (Picard et al., 1990), including the glucocorticoid responsive element (GRE). These and other examples are described in Mumber et al., 1995; Ronicke et al., 1997; Gao, 2000, all incorporated herein by reference. Yet other yeast vectors containing constitutive or inducible promoters such as alpha factor, alcohol oxidase, and PGH may be used. For reviews, see Ausubel et al. and Grant et al., 1987.

In some embodiments, a yeast strain is used that allows for expression, e.g., inducible expression, from GAL promoters on carbon sources other than galactose. In some embodiments, the strain carries an integrated or episomal (e.g., plasmid-borne) gene encoding a fusion protein, wherein the Gal4 DNA binding domain is fused to a transcriptional activation domain and a regulatory domain. The fusion protein is characterized in that its ability to activate transcription is regulated by binding of a small molecule to the regulatory domain. For example, in some embodiments, the fusion protein does not activate transcription in the absence of the small molecule, whereas in the presence of the small molecule, the fusion protein activates transcription. Exemplary small molecules include, e.g., steroid hormones, wherein the corresponding regulatory domain comprises at least a portion of a receptor for the small molecule. For example, the small molecule may be an estrogen (e.g., estradiol), or analog thereof (e.g., tamoxifen), and the corresponding regulatory domain comprises at least a portion of the estrogen receptor (ER). Exemplary activation domains include, e.g., viral protein activation domains such as the herpes simplex virus protein VP16 activation domain. In some embodiments, the strain carries an integrated or episomal (e.g., plasmid-borne) gene encoding a Gal4-ER-VP16 fusion protein. The presence of an estrogen receptor ligand, e.g., estradiol, in the medium, allows for expression from GAL promoters on carbon sources other than galactose. Numerous ways exist to render expression of a molecule of interest, e.g., an amyloid beta peptide, conditional, e.g., on culture media containing galactose or other carbon sources.

Certain aspects of the present disclosure provide methods of screening for a candidate drug (agent or compound) or a genetic factor that modulates amyloid beta-induced toxicity. Various types of candidate drugs may be screened by the methods described herein, including nucleic acids, polypeptides, small molecule compounds, and peptidomimetics. In some cases, genetic agents can be screened by contacting the yeast cell with a nucleic acid construct coding for a gene. For example, one may screen cDNA libraries expressing a variety of genes, to identify genes that modulate amyloid beta-induced toxicity.

For example, the identified drugs may modulate amyloid beta-induced toxicity. Accordingly, irrespective of the exact mechanism of action, drugs identified by the screening methods described herein are expected to provide therapeutic benefit to Alzheimer's disease.

Certain aspects of the present disclosure provide methods of identifying compounds or genes that modulate amyloid beta-induced toxicity. One of the strongest aspects of yeast is the possibility of performing high throughput screens that may identify genes, peptides and other compounds with the potential to ameliorate toxicity. A large number of compounds can be screened under a variety of growth conditions and in a variety of genetic backgrounds. The toxicity screen has the advantage of not only selecting for compounds that interact with amyloid beta, but also upstream or downstream targets that are not themselves cytotoxic and that are not yet identified.

In certain embodiments, candidate drugs can be screened from large libraries of synthetic or natural compounds. One example is an FDA approved library of compounds that can be used by humans. In addition, compound libraries are commercially available from a number of companies including but not limited to Maybridge Chemical Co. (Trevillet, Cornwall, UK), Comgenex (Princeton, N.J.), Microsource (New Milford, Conn.), Aldrich (Milwaukee, Wis.), AKos Consulting and Solutions GmbH (Basel, Switzerland), Ambinter (Paris, France), Asinex (Moscow, Russia), Aurora (Graz, Austria), BioFocus DPI, Switzerland, Bionet (Camelford, UK), ChemBridge, (San Diego, Calif.), ChemDiv, (San Diego, Calif.), Chemical Block Lt, (Moscow, Russia), ChemStar (Moscow, Russia), Exclusive Chemistry, Ltd (Obninsk, Russia), Enamine (Kiev, Ukraine), Evotec (Hamburg, Germany), Indofine (Hillsborough, N.J.), Interbioscreen (Moscow, Russia), Interchim (Montlucon, France), Life Chemicals, Inc. (Orange, Conn.), Microchemistry Ltd. (Moscow, Russia), Otava, (Toronto, ON), PharmEx Ltd (Moscow, Russia), Princeton Biomolecular (Monmouth Junction, N.J.), Scientific Exchange (Center Ossipee, N.H.), Specs (Delft, Netherlands), TimTec (Newark, Del.), Toronto Research Corp. (North York ON), UkrOrgSynthesis (Kiev, Ukraine), Vitas-M, (Moscow, Russia), Zelinsky Institute, (Moscow, Russia), and Bicoll (Shanghai, China). Combinatorial libraries are available and can be prepared. Libraries of natural compounds in the form of bacterial, fungal, plant and animal extracts are commercially available or can be readily prepared by methods well known in the art. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Several commercial libraries can be used in the screens.

Another embodiment relates to genetic screens. For example, genomic libraries and disruption libraries can be screened to find extragenic suppressors or enhancers of amyloid beta-induced toxicity. Because the yeast genome is small, 10,000 transformants of each type should be sufficient for good coverage.

Another embodiment contemplates screening assays using fluorescent resonance energy transfer (FRET). FRET occurs when a donor fluorophore is in close proximity (10-60 A) to an acceptor fluorophore, and when the emission wavelength of the first overlaps the excitation wavelength of the second (Kenworthy A K et al., 2001. Methods. 24:289-96). FRET should occur when cyan fluorescent protein (CFP) and yellow fluorescent protein (YFP) fusion proteins are actually part of the same complex.

For example, an amyloid beta protein can be fused to CFP and to YFP respectively, and integrated in the yeast genome under the regulation of a GAL1-10 promoter. Cells are grown in galactose to induce expression. Upon induction, cells produce the fusion proteins, which aggregate and bring the CFP and YFP close together. Because proteins in the aggregates are tightly packed, the distance between the CFP and YFP is less than the critical value of 100 A that is necessary for FRET to occur. In this case, the energy released by the emission of CFP will excite the YFP, which in turn will emit at its characteristic wavelength. FRET based screening can be used to identify candidate compounds including, drugs, genes or other factors that can disrupt the interaction of CFP and YFP by maintaining the proteins in a state that does not allow aggregation to occur.

One embodiment contemplates screening assays using fluorescence activated cell sorting (FACS) analysis. FACS provides the means of scanning individual cells for the presence of fluorescently labeled/tagged moiety. The method is unique in its ability to provide a rapid, reliable, quantitative, and multiparameter analysis on either living or fixed cells. For example, an amyloid beta protein can be suitably labeled, and provide a useful tool for the analysis and quantitation of protein aggregation as a result of other genetic or growth conditions of individual yeast cells as described above.

Screens (e.g., for compounds and/or for genetic suppressors or enhancers) can be carried out under a variety of different conditions. For example, a variety of different culture media can be used. Culture media can contain different carbon sources, e.g., different sugars such as glucose, glycerol, galactose, raffinose, etc. In some embodiments, multiple screens are performed using two, three, or more different culture conditions (e.g., culture media containing different carbon sources), and compounds or genes identified as "hits" under at least two different culture conditions are identified. In some embodiments, screens are performed under two or more different culture conditions (e.g., using culture media containing different carbon sources), wherein the different culture conditions (e.g., different carbon sources) result in different levels of mitochondrial respiration. For example, growth using culture media containing glucose, glycerol, or galactose result in different levels of mitochondrial respiration. In glucose, yeast cells ferment and respiration remains low until all glucose is converted to ethanol. In galactose, respiration is moderately active. In glycerol, yeast cells are completely dependent on respiration for growth. In some embodiments, a screen is performed in parallel using media containing glucose, galactose, or glycerol as a carbon source.

Certain embodiments provide methods of further testing those potential drugs that have been identified in the yeast system, in other model systems. The model systems include, but are not limited to, worms, flies, mammalian cells, and in vivo animal models.

Mammalian Expression Constructs, Cells, and Screening Assays

An amyloid beta nucleic acid can be transfected into a mammalian cell using nucleic acid vectors that include, but are not limited to, plasmids, linear nucleic acid molecules, artificial chromosomes, and viral vectors. The vectors can contain as a transgene any of the amyloid beta nucleic acids described herein.

Once the vector or nucleic acid molecule containing the construct(s) has been prepared for expression, the DNA construct(s) can be introduced into an appropriate host cell by any of a variety of suitable means, i.e., transformation, transfection, conjugation, protoplast fusion, electroporation, particle gun technology, calcium phosphate-precipitation, direct microinjection, and the like. Where the vector is a viral vector (e.g., a lentiviral vector), the vector can be delivered to the cell by direct infection. Preferably the vector is stably integrated into the host genome. Methods of producing a cell line containing a stably integrated nucleic acid (e.g., a vector) are well known in the art (see, for example, Sambrook et al. in Molecular Cloning: A Laboratory Manual. Cold Spring Harbor Laboratory Press, NY, Vol. 1, 2, 3 (1989)). Briefly, a cell transfected with a nucleic acid can be selected for using a host of antibiotics including, for example, G418, neomycin, or hygromycin B. Generally, the transfected nucleic acid contains a suitable antibiotic resistance gene or is co-transfected with a vector containing a suitable antibiotic resistance gene. Thus, only cells and their progeny which contain a stably integrated nucleic acid encoding the antibiotic resistance gene will survive when grown in antibiotic.

Amyloid beta can be expressed under the control of an inducible promoter. Methods for assessing the induction of amyloid beta following administration of an inducer include western blotting using an antibody specific for amyloid beta or RT-PCR or northern blotting techniques to detect mRNA expression of amyloid beta. Such methods are well known to those in the art and are described in detail in Sambrook et al. (in Molecular Cloning: A Laboratory Manual. Cold Spring Harbor Laboratory Press, NY, Vol. 1, 2, 3 (1989)). Expression of amyloid beta can be detected, e.g., at about one hour (e.g., about 30 minutes, about 90 minutes, about two hours, about three hours, about 4 hours, about 6 hours, about 8 hours, about 12 hours, about 12 hours, about 16 hours, about 20 hours, about 24 hours, about 36 hours, about 48 hours or more) post-induction. In some embodiments, one can assess (evaluate) a change in expression over time post-induction. For example, the amount of expression of amyloid beta before induction (i.e., before the inducer is added) can be compared to the expression of amyloid beta by the cells at various time points (e.g., 1, 4, 8, and 12 hours; 4, 8, 12 and 16 hours; 8, 12, 16, and 20 hours; 12, 24, 36, and 48 hours) post-induction.

A suitable starting concentration of an inducing agent is about 0.001 µM (e.g., about 0.01 µM, about 0.1 µM, about 1.0 µM, about 10.0 µM, about 100 µM). It is understood that the concentration of the inducing agent can be optimized for the particular experiment and can depend on, for example, the cell line, the transgene, or the culture conditions the cells are grown in (e.g., low serum conditions).

In some embodiments, a mammalian cell (e.g., a mammalian neuronal cell) containing a nucleic acid vector encoding amyloid beta under control of an inducible promoter is in a non-human mammal (e.g., mouse, rat, or guinea pig). The vector can be introduced to the mammalian cell (e.g., a neuronal cell) ex vivo, i.e., the cell can be transfected in vitro and then implanted or otherwise delivered to the mammal (e.g., surgically implanted). Alternatively, a non-human transgenic animal can be established wherein the nucleic acid vector using any of a variety of techniques known in the art (see, for example, Manson et al. (2001) Exp. Rev. Mol. Med. 11; and Hofker et al. Transgenic Mouse: Methods and Protocols (Methods in Molecular Biology) Humana Press, Clifton, N.J., Vol. 29 (2002)).

In those embodiments where an inducible promoter is used, induction of expression of amyloid beta in an animal can be accomplished by administering to the animal an appropriate amount of the inducer. The inducer can be delivered to the mammal as part of food or water (i.e., in the food or water) or can be administered intravenously or parenterally (e.g., subcutaneous injection). Suitable dosages of inducing agent and methods for detecting induction of a transgene in an animal model are described in, for example, Teng et al. (2002) Physiol. Genomics 11:99-107; Kim et al. (2003) Am. J. Pathol. 162(5):1693-1707; and Zabala et al. (2004) Cancer Res. 64:2799-2804.

It is understood that any of the in vitro or in vivo embodiments of the mammalian cell described above can be used in the following screening methods.

Certain aspects of the present disclosure provide methods of screening for and identifying a "candidate agent" (e.g., a compound or a drug) that prevents or suppresses cytotoxicity resulting from overexpression of amyloid beta in a mammalian neuronal cell. Thus, a "candidate agent," as referred to herein, is any substance with a potential to reduce, interfere with or curtail (i.e., prevent or suppress) cytotoxicity resulting from overexpression of amyloid beta in a mammalian neuronal cell.

Various types of candidate agents can be screened by the methods described herein, including, but not limited to, nucleic acids, polypeptides, small molecule compounds, large molecule compounds, peptidomimetics or any other compounds described herein (e.g., see "Compounds" below). In some instances, the candidate agents are genetic agents that reduce, interfere with, or curtail cytotoxicity resulting from overexpression of amyloid beta in a mammalian neuronal cell. For example, a cDNA library containing coding sequences for a variety of genes can be screened to identify potential therapeutic genes for the diseases described herein. Alternatively, a screen can be performed to identify genetic elements that contribute to cytotoxicity resulting from amyloid beta expression in a mammalian cell. For example, a library of siRNAs or antisense oligonucleotides can be screened such that the level or amount of cytotoxicity in the absence of one or more genes could be determined. In another example, a mammalian neuronal cell could be mutagenized to inactivate one or more genes prior to performing the screening assay. In these examples, a reduced level of amyloid beta-induced cytotoxicity in a cell in the absence of a gene (through mutational inactivation or silencing) indicates that the gene contributes to amyloid beta-induced cytotoxicity. Accordingly, siRNAs or antisense oligonucleotides that target that gene, for example, can be useful in treating Alzheimer's disease.

Screening methods to identify an agent capable of preventing or suppressing cytotoxicity resulting from overexpression of amyloid beta can involve the steps of: (i) culturing the cell in the presence of a candidate agent and under conditions that allow for expression of the nucleic acid encoding amyloid beta at a level that, in the absence of the candidate agent, is sufficient to induce toxicity in the cell; (ii) measuring cell viability in the presence of the candidate agent; and (iii) comparing cell viability measured in the presence of the candidate agent to cell viability in the absence of the candidate agent, where if cell viability is greater in the presence of the candidate agent as compared to in the absence of the candidate agent, then the candidate agent is identified as a compound that prevents or suppresses amyloid beta-induced toxicity.

The screening assays can involve a mammalian cell containing a stably integrated nucleic acid encoding amyloid beta (optionally under the control of an inducible promoter). Although the cell can be any mammalian cell, preferably the cell is a neuronal cell (e.g., primary neuronal cells or a neural cell line such as PC12, H4, SK-N-SH, SH-SY5Y, Neuro-2a, SVG p12, CCF-STTG1, SW 1088, SW 1783, LN-18, A172, U-138 MG, T98G, U-87 MG, U-118 MG, Hs 683, M059K, M059J, H4, LN-229, Daoy, or PFSK-1). Additional cell lines are available at the American Type Culture Collection (ATCC), Manassass, Va.

The cells can be treated with two or more concentrations of a compound, where, for example, a concentration-dependence or EC50 is to be determined. Suitable concentrations of a candidate compound for the assay include, for example, about 0.01 µM to 1 mM of the agent (e.g., about 0.01 µM to 0.1 µM, about 0.1 µM to 1 µM, about 1 µM to 10 µM, about 10 to 1 mM, or about 100 µM to 1 mM).

Methods of assessing the efficacy of an agent to prevent or suppress amyloid beta-induced cytotoxicity can be quantitative, semi-quantitative, or qualitative. Thus, for example, the activity of an agent can be determined as a discrete value. An example of a quantitative determination of an agent's is a 50% Effective Concentration, or EC50 value, which is the molar concentration of an agent (e.g., a compound) that gives one-half the maximal response of that agent. Alternatively, the efficacy of an agent can be assessed using a variety of semi-quantitative/qualitative systems known in the art. Thus, the efficacy of an agent to prevent or suppress amyloid beta-induced cytotoxicity in a mammalian cell can be expressed as, for example, (a) one or more of "excellent", "good", "satisfactory", "unsatisfactory", and/or "poor"; (b) one or more of "very high", "high", "average", "low", and/or "very low"; or (c) one or more of "+++++", "++++", "+++", "++", "+", "+/−", and/or "−".

Methods include determining the efficacy of agents in preventing or suppressing amyloid beta-induced cytotoxicity in a mammalian cell (e.g., a compound such as any of those described herein). Cells are generally plated on solid support matrix (e.g., a plastic tissue culture plate, or a multi-well (96 or 386-well) tissue culture plate) and grown in appropriate medium. Cells are then contacted with serial dilutions of a candidate agent generally ranging, for example, from 10 µM to 0.1 µM concentration. Often, a control compound (e.g., a known inhibitor of known concentration) is also added to a set of cells as an internal standard. Often, a set of cells are grown in the presence of a carrier, buffer, or solvent, in which the compound is delivered. Cells are grown in the presence or absence of test compounds for varying times, for example, from 1 to three days (1 day, 2 days, 3 days, 4 days, 1 week, 2 weeks), followed by a test for the number of cells remaining on the plate or the viability of the cells remaining on the plate. Methods of detecting (e.g., determining or measuring) the extent of amyloid beta-induced cytotoxicity in the presence or absence of an agent are myriad and well known to those of ordinary skill in the art. These methods can include, for example, measuring ATP concentration in a cell. The amount of ATP present in a cell or population of cells is proportional to the number of viable cells in that population. In one example, ATP concentration can be determined enzymatically, for example, by using luciferase/luciferin. These enzymes produce a light signal in a reaction requiring ATP hydrolysis. Thus, the more ATP present in a sample, the more light produced. In this method, cells are first harvested and lysed. Cell lysates are then incubated with luciferase/luciferin and the amount of ATP-dependent light produced from the sample can be detected and/or quantitated using a luminometer (e.g., Turner BioSystems TD-20/20 Luminometer, Turner Biosystems, Sunnyvale, Calif.). In this case, to determine the efficacy of a given agent in preventing or suppressing amyloid beta-induced cytotoxicity, the amount of light signal produced from induced cells in the presence of the compound can be compared to the light signal produced from induced cells in the absence of the agent. Where more light signal is produced from lysates of cells cultured in the presence of the agent as compared to cells cultured in the absence of the agent, this indicates that the compound prevents or suppresses cytotoxicity. Further examples of this method are set forth in the Examples.

Other suitable methods for determining the efficacy of agents in preventing or suppressing amyloid beta-induced cytotoxicity include, for example, counting the number of cells remaining after the period of induction in the absence or presence of the agent. In this method, cells can be trypsinized from the plate, washed, stained with a dye (e.g., trypan blue), and counted using a microscope or mechanical cell counter (Beckman-Coulter Z1™ Series COULTER COUNTER® Cell and Particle Counter). Since dyes like trypan blue are only taken up by dead or dying cells, this method allows for discrimination (i.e., blue or white cell) between viable and non-viable cells in a population. Another method for determining prevention or suppression of amyloid beta-induced cytotoxicity by an agent (e.g., any one of the compositions described herein) following treatment is a metabolic assay, for example, an MTT-metabolic assay (Invitrogen, USA). MTT Diphenyltetrazolium Bromide, is a tetrazolium salt (yellowish) that is cleaved to formazan crystals by the succinate dehydrogenase system which belongs to the mitochondrial respiratory chain, and is only active in viable cells. The mitochondrial succinate dehydrogenase reduces the MTT crystals into purple formazan in the presence of an electron coupling reagent. Following the treatment of the cells with a compound, the cells are exposed to the MTT reagent and the more viable cells are present in a well, the more formazan dye is produced. The amount of formazan dye can be measured, for example, using a spectrophotometer.

Other commonly used methods of testing for prevention or suppression of cytotoxicity in a cell (e.g., cytotoxicity resulting from overexpression of amyloid beta in a mammalian cell) by an agent (e.g., a compound or a composition described herein) include the monitoring of DNA synthesis in the cell. For example, induced cells grown in the presence or absence of an agent are also treated with a nucleotide analog that can incorporate into the DNA of the cell upon cell division. Examples of such nucleotide analogs include, for example, BrdU or $^3$H-Thymidine. In each case, the amount of label incorporated into the induced cells (grown in the presence and absence of a given agent) is quantitated, and the amount of label incorporation is directly proportional to the amount of cell growth in the population of cells. The amount of label incorporated in the induced cells in the presence and absence of an agent can be normalized to the amount of label incorporated into uninduced cells. More signal (i.e., more DNA synthesis) in an induced cell set treated with the agent as compared to induced cells not treated with the agent indicates that the agent prevents or suppresses amyloid beta-induced cytotoxicity.

Other suitable methods for assessing suppression or prevention of amyloid beta-induced cytotoxicity by an agent include the detection of apoptosis in a cell. Such methods of detecting or measuring apoptosis include, for example, monitoring DNA fragmentation, caspase activation, or annexin V expression.

It should be understood that the screening methods described herein can also be used as secondary, or cell-based screens to identify compounds useful in treating a Alzheimer's disease. For example, the screening methods can be used following a primary screen where, for example, a compound is first selected based on an ability to inhibit amyloid beta-induced toxicity in another system (e.g., yeast).

Screening assays can be performed in any format that allows for rapid preparation, processing, and analysis of multiple reactions. This can be, for example, in multi-well assay plates (e.g., 96 wells or 386 wells). Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting the signal generated from the assay. Examples of such detectors include, but are not limited to, spectrophotometers, luminometers, fluorimeters, and devices that measure radioisotope decay.

Compounds

Compounds to be screened or identified using any of the methods described herein can include various chemical classes, though typically small organic molecules having a molecular weight in the range of 50 to 2,500 daltons. These compounds can comprise functional groups necessary for structural interaction with proteins (e.g., hydrogen bonding), and typically include at least an amine, carbonyl, hydroxyl, or carboxyl group, and preferably at least two of the functional chemical groups. These compounds often comprise cyclical carbon or heterocyclic structures and/or aromatic or polyaromatic structures (e.g., purine core) substituted with one or more of the above functional groups.

In alternative embodiments, compounds can also include biomolecules including, but not limited to, peptides, polypeptides, peptidomimetics (e.g., peptoids), amino acids, amino acid analogs, saccharides, fatty acids, steroids, purines, pyrimidines, derivatives or structural analogues thereof, polynucleotides, nucleic acid aptamers, and polynucleotide analogs.

Compounds can be identified from a number of potential sources, including: chemical libraries, natural product libraries, and combinatorial libraries comprised of random peptides, oligonucleotides, or organic molecules. Chemical libraries consist of diverse chemical structures, some of which are analogs of known compounds or analogs or compounds that have been identified as "hits" or "leads" in other drug discovery screens, while others are derived from natural products, and still others arise from non-directed synthetic organic chemistry. Natural product libraries are collections of microorganisms, animals, plants, or marine organisms which are used to create mixtures for screening by: (1) fermentation and extraction of broths from soil, plant or marine microorganisms, or (2) extraction of plants or marine organisms. Natural product libraries include polypeptides, non-ribosomal peptides, and variants (non-naturally occurring) thereof. For a review, see Science 282:63-68 (1998). Combinatorial libraries are composed or large numbers of peptides, oligonucleotides, or organic compounds as a mixture. These libraries are relatively easy to prepare by traditional automated synthesis methods, PCR, cloning, or proprietary synthetic methods. Of particular interest are non-peptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, Curr. Opin. Biotechnol. 8:701-707 (1997).

Identification of test compounds through the use of the various libraries herein permits subsequent modification of the test compound "hit" or "lead" to optimize the capacity of the "hit" or "lead" to prevent or suppress amyloid beta-induced toxicity and/or amyloid beta-induced aggregation.

The compounds identified above can be synthesized by any chemical or biological method. The compounds identified above can also be pure, or may be in a composition (e.g., a pharmaceutical composition) that contains one or more additional component(s), and can be prepared in an assay-, physiologic-, or pharmaceutically-acceptable diluent or carrier (see below).

Pharmaceutical Compositions and Methods of Treatment

A compound that is found to prevent or suppress amyloid beta-induced toxicity or the formation of amyloid beta aggregates in a cell can be formulated as a pharmaceutical composition, e.g., for administration to a subject to treat a neurodegenerative disease such as Alzheimer's disease.

A pharmaceutical composition typically includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (see e.g., Berge et al., J. Pharm. Sci. 66:1-19, 1977).

The compound can be formulated according to standard methods. Pharmaceutical formulation is a well-established art, and is further described, e.g., in Gennaro (ed.), Remington: The Science and Practice of Pharmacy, 20th ed., Lippincott, Williams & Wilkins (2000) (ISBN: 0683306472); Ansel et al., Pharmaceutical Dosage Forms and Drug Delivery Systems, 7th Ed., Lippincott Williams & Wilkins Publishers (1999) (ISBN: 0683305727); and Kibbe (ed.), Handbook of Pharmaceutical Excipients American Pharmaceutical Association, 3rd ed. (2000) (ISBN: 091733096X).

In one embodiment, a compound that prevents or suppresses amyloid beta-induced toxicity and/or amyloid beta aggregate formation in a cell can be formulated with excipient materials, such as sodium chloride, sodium dibasic phosphate heptahydrate, sodium monobasic phosphate, and a stabilizer. It can be provided, for example, in a buffered solution at a suitable concentration and can be stored at 2-8° C.

The pharmaceutical compositions may be in a variety of forms. These include, for example, liquid, semi-solid and solid dosage forms, such as liquid solutions (e.g., injectable and infusible solutions), dispersions or suspensions, tablets, capsules, pills, powders, liposomes and suppositories. The preferred form can depend on the intended mode of administration and therapeutic application. In some embodiments, compositions for the agents described herein are in the form of injectable or infusible solutions.

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating a compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of a compound plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the compound can be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Sustained and Controlled Release Drug Delivery Systems, J. R. Robinson, ed., Marcel Dekker, Inc., New York, 1978.

A compound identified as one that prevents or suppresses amyloid beta-induced toxicity and/or amyloid beta aggregate formation in a cell can be modified, e.g., with a moiety that improves its stabilization and/or retention in circulation, e.g., in blood, serum, or other tissues, e.g., by at least 1.5, 2, 5, 10, or 50 fold. The modified compound can be evaluated to assess whether it can reach treatment sites of interest (e.g., locations of aggregate amyloid beta) such as can occur in a cell in a subject with a neurodegenerative disease such as Alzheimer's disease (e.g., by using a labeled form of the compound).

For example, the compound can be associated with a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used. For example, a compound can be conjugated to a water soluble polymer, e.g., a hydrophilic polyvinyl polymer, e.g., polyvinylalcohol or polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; and branched or unbranched polysaccharides.

When the compound is used in combination with a second agent (e.g., any additional therapies for Alzheimer's disease), the two agents can be formulated separately or together. For example, the respective pharmaceutical compositions can be mixed, e.g., just prior to administration, and administered together or can be administered separately, e.g., at the same or different times.

Compounds identified as described herein can be used to treat a subject (e.g., a human subject) that is at risk for or has a disorder associated with amyloid beta mediated toxicity and/or the formation, deposition, accumulation, or persistence of amyloid beta aggregates, e.g., amyloid beta oligomers and/or dimers. In certain embodiments, the disorder is Alzheimer's disease, Down Syndrome, Fragile X syndrome, or systemic amyloidosis. Methods of identifying an individual at risk for or having such disorders are known in the art. For example, Alzheimer's disease can be diagnosed based on, e.g., patient history (e.g., memory loss), clinical observations, the presence of characteristic neurological and neuropsychological features, and the absence of other conditions that might be responsible for the foregoing. Imaging techniques such as computed tomography (CT), magnetic resonance imaging (MRI), single photon emission computed tomography (SPECT), or positron emission tomography (PET) can be of use. Diagnosis can be confirmed by post-mortem examination of brain material. Exemplary criteria for diagnosis of Alzheimer's disease are found in the Diagnostic and Statistical Manual of Mental Disorders (DSM)-IV (text revision, 2000) or DSM-V and the National Institute of Neurological and Communicative Disorders and Stroke (NINCDS)-Alzheimer's Disease and Related Disorders Association (ADRDA) criteria (McKhann G, et al. (1984) Neurology 34 (7): 939-44), e.g., as updated (Dubois B, et al. (2007) Lancet Neurol 6 (8): 734-46). Analysis of cerebrospinal fluid (CSF) for various biomarkers, e.g., amyloid beta or tau proteins (e.g., total tau protein and phosphorylated tau) and/or imaging (e.g., PET imaging) with labeled compounds that bind to amyloid beta deposits (e.g., 11C-labeled Pittsburgh Compound-B (11C-PIB) or 18F-AV-45 (flobetapir F18)) can be used to predict the onset of AD, e.g., to identify individuals who have a significant likelihood of progressing to Alzheimer's disease in the future (e.g., within the next two years). Such imaging methods may also be of use in the instant invention to assess the in vivo effect of compounds identified herein. In some embodiments, a subject has a mutation in a gene encoding amyloid precursor protein (APP), presenilin 1, or presenilin 2. In some embodiments, the mutation increases the production of Aβ42 or alters the ratio of Aβ42 to Aβ40. In some embodiments the subject has at least one copy of the ε4 allele of the apolipoprotein E (APOE) gene.

Down Syndrome can be diagnosed based on presence of trisomy 21.

Fragile X Syndrome is caused by expansion of a trinucleotide gene sequence (CGG) on the X chromosome that results in a failure to express the protein coded by the FMR1 gene, which encodes FMRP. It may be suspected based on the presence of characteristic signs and symptoms, with diagnostic confirmation from genetic testing.

Thus, methods and compositions for treating a subject at risk of (or susceptible to) an amyloid beta mediated disease are described herein. For example, an individual who is at risk of developing Alzheimer's disease and/or has signs suggesting that he or she will develop Alzheimer's disease can be treated with the compounds and methods described herein.

As used herein, the term "treatment" is defined as the application or administration of a therapeutic compound to a patient, or application or administration of a therapeutic compound to a subject (e.g., a human subject, who may be referred to as a "patient") who has a disease (or other medically recognized disorder or syndrome), a symptom of disease or a predisposition toward a disease (e.g., one or more risk factors associated with the disease), with the purpose to cure, heal, alleviate, relieve, alter, remedy, ameliorate, improve, or affect (in a manner beneficial to the subject) the disease, the symptoms of disease or the predisposition toward disease. In some embodiments, treatment is prophylactic, i.e., it is administered to a subject who has not developed the disease (and who may or may not have a predisposition to develop the disease) with an intent to delay, prevent, or reduce the likelihood that the subject will develop the disease or reduce the severity should the subject develop the disease. Compounds may also or alternately be administered to a subject for purposes of testing, research, or diagnosis and/or may be contacted with an isolated tissue, cells, or cell line from a patient, e.g., for purposes of testing, research, diagnosis, or with an intent to subsequently administer the isolated tissue, cells, or cell line to the subject for treatment.

The following are examples of the practice of the invention. They are not to be construed as limiting the scope of the invention in any way.

EXAMPLES

Example 1: Amyloid Beta Expression Constructs for Yeast Cells

The mating factor alpha 1 gene in yeast encodes a precursor protein of 165 amino acids, called the prepro-alpha-factor. This prepro-alpha-factor consists of a 19-amino acid signal peptide, a 64-amino acid pro region and 4 tandem repeats of alpha-factor sequence, each preceded by a spacer peptide with signature proteolytic cleavage sites. The precursor protein undergoes a series of sequential and defined posttranslational enzymatic modification and proteolytic processing steps in the secretory pathway of the cell to generate the mature 13-amino acid long peptide pheromone, alpha-factor. The nascent prepro-alpha polypeptide is translocated into the lumen of ER, where the signal sequence is cleaved by a signal peptidase to produce the pro-alpha-factor. In the ER lumen, N-linked carbohydrates are added to three specific glycosylation sites within the pro region, a step that is necessary for the transport of the pro-alpha-factor from the ER to Golgi. Further carbohydrate modification takes place in the Golgi before the final proteolytic processing steps. The first of these three proteolytic processing steps is by the KEX2 endopeptidase that cleaves on the carboxyl side of Lys-Arg (KR) residues at the N terminus of each of the spacer repeats (KREAEA (SEQ ID NO:44) or KREAEAEA (SEQ ID NO:45) or KREADAEA (SEQ ID NO:46)). The second proteolytic processing occurs when the dibasic KR residues are removed from the C terminus of alpha-factor by KEX1 carboxypeptidase B (CoxyPdaseB). Finally, the remaining amino acids of the spacer (EAEA (SEQ ID NO:47) or EAEAEA (SEQ ID NO:48) or EADAEA (SEQ ID NO:49)) are cleaved from the N terminus of alpha-factor by STEB3 encoded dipeptidyl aminopeptidase (DAPdaseA). Mature alpha-factor is then secreted into the extracellular medium.

The human Aβ42 coding sequence was inserted into the mating factor alpha 1 prepro sequence, wherein the 13-amino acid long alpha-factor peptide sequence was replaced by the Aβ42 sequence, leaving all the other sequence components of the prepro-alpha factor intact (FIG. 1A). Constructs were prepared based upon the mating factor alpha 1 prepro sequence backbone and containing (i) one (1X), two (2X), four (4X), six (6X), or eight (8X) copies of Aβ42, (ii) four (4X) or six (6X) copies of Aβ40, or four (4X) copies of scrambled Aβ42 (FIG. 1B). The nucleotide and amino acid sequences of the fusion polypeptides encoded by the expression constructs are as follows.

Matα-Aβ42_1X Nucleotide Sequence
(SEQ ID NO: 50)
GTCGACTGGATCCACAAGTTTGTACAAAAAAGCAGGCTGGTACCAAAAGA

ATGAGATTTCCTTCAATTTTTACTGCAGTTTTATTCGCAGCATCCTCCGC

ATTAGCTGCTCCAGTCAACACTACAACAGAAGATGAAACGGCACAAATTC

CGGCTGAAGCTGTCATCGGTTACTTAGATTTAGAAGGGGATTTCGATGTT

GCTGTTTTGCCATTTTCCAACAGCACAAATAACGGGTTATTGTTTATAAA

TACTACTATTGCCAGCATTGCTGCTAAAGAAGAAGGGGTATCTTTGGATA

AAAGAGAGGCTGAAGCTGATGCTGAATTTAGACATGATTCTGGTTATGAA

GTTCATCATCAAAAATTGGTTTTTTTTGCTGAAGATGTTGGTTCTAATAA

AGGTGCTATTATTGGTTTGATGGTTGGTGGTGTTGTCATTGCTAAGAGAG

AAGCCGAAGCTGAAGCTGATGCTGAATTTAGACATGATTCTGGTTATGAA

GTTCATCATCAAAAATTGGTTTTTTTTGCTGAAGATGTTGGTTCTAATAA

AGGTGCTATTATTGGTTTGATGGTTGGTGGTGTTGTCATTGCTTAAACCC

AGCTTTCTTGTACAAAGTGGTGCGGCCGCACTCGAG

Matα-Aβ42_1X Amino Acid Sequence
(SEQ ID NO: 51)
MRFPSIFTAVLFAASSALAAPVNTTTEDETAQIPAEAVIGYLDLEGDFDV

AVLPFSNSTNNGLLFINTTIASIAAKEEGVSLDKREAEADAEFRHDSGYE

VHHQKLVFFAEDVGSNKGAIIGLMVGGVVIA

Matα-Aβ42_2X Nucleotide Sequence
(SEQ ID NO: 52)
GTCGACTGGATCCACAAGTTTGTACAAAAAAGCAGGCTGGTACCAAAAGA

ATGAGATTCCCATCTATTTTCACCGCTGTTTTGTTTGCTGCTTCTTCTGC

TTTGGCTGCTCCAGTTAACACTACTACTGAAGATGAAACTGCTCAAATTC

CAGCTGAAGCTGTTATTGGTTACTTGGATTTGGAAGGTGATTTCGATGTT

GCTGTTTTGCCATTCTCTAACTCTACCAACAATGGTTTGTTGTTCATCAA

CACCACCATTGCTTCTATTGCTGCTAAAGAAGAAGGTGTCTCTTTGGATA

AGAGAGAAGCTGAAGCAGACGCAGAATTCAGACATGATTCTGGTTATGAA

GTTCACCACCAAAAGTTGGTTTTCTTCGCTGAAGATGTTGGTTCTAACAA

GGGTGCTATTATCGGTTTGATGGTTGGTGGTGTAGTTATTGCTAAAAGAG

AAGCCGAAGCTGAAGCTGATGCCGAATTCAGACACGATAGTGGTTACGAA

GTACATCATCAAAAATTAGTCTTTTTTGCCGAAGATGTCGGTAGTAACAA

AGGTGCAATCATTGGTTTAATGGTCGGTGGTGTCGTAATCGCTTAAACCC

AGCTTTCTTGTACAAAGTGGTGCGGCCGCACTCGAG

Matα-Aβ42_2X Amino Acid Sequence
(SEQ ID NO: 53)
MRFPSIFTAVLFAASSALAAPVNTTTEDETAQIPAEAVIGYLDLEGDFDV

AVLPFSNSTNNGLLFINTTIASIAAKEEGVSLDKREAEADAEFRHDSGYE

VHHQKLVFFAEDVGSNKGAIIGLMVGGVVIAKREAEAEADAEFRHDSGYE

VHHQKLVFFAEDVGSNKGAIIGLMVGGVVIA

Matα-Aβ42_4X Nucleotide Sequence
(SEQ ID NO: 54)
GTCGACTGGATCCACAAGTTTGTACAAAAAAGCAGGCTGGTACCAAAAGA

ATGAGATTTCCTTCAATTTTTACTGCAGTTTTATTCGCAGCATCCTCCGC

ATTAGCTGCTCCAGTCAACACTACAACAGAAGATGAAACGGCACAAATTC

-continued

CGGCTGAAGCTGTCATCGGTTACTTAGATTTAGAAGGGGATTTCGATGTT

GCTGTTTTGCCATTTTCCAACAGCACAAATAACGGGTTATTGTTTATAAA

TACTACTATTGCCAGCATTGCTGCTAAAGAAGAAGGGGTATCTTTGGATA

AAAGAGAGGCTGAAGCTGATGCTGAATTTAGACATGATTCTGGTTATGAA

GTTCATCATCAAAAATTGGTTTTTTTGCTGAAGATGTTGGTTCTAATAA

AGGTGCTATTATTGGTTTGATGGTTGGTGGTGTTGTCATTGCTAAGAGAG

AAGCCGAAGCTGAAGCTGATGCTGAATTTAGACATGATTCTGGTTATGAA

GTTCATCATCAAAAATTGGTTTTTTTGCTGAAGATGTTGGTTCTAATAA

AGGTGCTATTATTGGTTTGATGGTTGGTGGTGTTGTCATTGCTAAAGAG

AAGCCGACGCTGAAGCTGATGCTGAATTTAGACATGATTCTGGTTATGAA

GTTCATCATCAAAAATTGGTTTTTTTGCTGAAGATGTTGGTTCTAATAA

AGGTGCTATTATTGGTTTGATGGTTGGTGGTGTTGTCATTGCTAAAGAG

AAGCCGACGCTGAAGCTGATGCTGAATTTAGACATGATTCTGGTTATGAA

GTTCATCATCAAAAATTGGTTTTTTTGCTGAAGATGTTGGTTCTAATAA

AGGTGCTATTATTGGTTTGATGGTTGGTGGTGTTGTCATTGCTTAAACCC

AGCTTTCTTGTACAAAGTGGTGCGGCCGCACTCGAG

Matα-Aβ42_4X Amino Acid Sequence
(SEQ ID NO: 55)
MRFPSIFTAVLFAASSALAAPVNTTTEDETAQIPAEAVIGYLDLEGDFDV

AVLPFSNSTNNGLLFINTTIASIAAKEEGVSLDKREAEADAEFRHDSGYE

VHHQKLVFFAEDVGSNKGAIIGLMVGGVVIAKREAEAEADAEFRHDSGYE

VHHQKLVFFAEDVGSNKGAIIGLMVGGVVIAKREADAEADAEFRHDSGYE

VHHQKLVFFAEDVGSNKGAIIGLMVGGVVIAKREADAEADAEFRHDSGYE

VHHQKLVFFAEDVGSNKGAIIGLMVGGVVIA

Matα-Aβ42_6X Nucleotide Sequence
(SEQ ID NO: 56)
GTCGACTGGATCCACAAGTTTGTACAAAAAAGCAGGCTGGTACCAAAGA

ATGAGATTCCCATCTATTTTCACCGCTGTTTTGTTTGCTGCTTCTTCTGC

TTTGGCTGCTCCAGTTAACACTACTACTGAAGATGAAACTGCTCAAATTC

CAGCTGAAGCTGTTATTGGTTACTTGGATTTGGAAGGTGATTTCGATGTT

GCTGTTTTGCCATTCTCTAACTCTACCAACAATGGTTTGTTGTTCATCAA

CACCACCATTGCTTCTATTGCTGCTAAAGAAGAAGGTGTCTCTTTGGATA

GAGAGAAGCTGAAGCAGACGCAGAATTCAGACATGATTCTGGTTATGAA

GTTCACCACCAAAAGTTGGTTTTCTTCGCTGAAGATGTTGGTTCTAACAA

GGGTGCTATTATCGGTTTGATGGTTGGTGGTGTAGTTATTGCTAAAGAG

AAGCCGAAGCTGAAGCTGATGCCGAATTCAGACACGATAGTGGTTACGAA

GTACATCATCAAAAATTAGTCTTTTTTGCCGAAGATGTCGGTAGTAACAA

AGGTGCAATCATTGGTTTAATGGTCGGTGGTGTCGTAATAGCCAAGAG

AAGCAGACGCCGAAGCCGATGCAGAATTCAGACACGACTCCGGTTACGAA

GTCCATCACCAAAAGTTGGTATTCTTTGCCGAAGATGTCGGTTCAAACAA

GGGTGCCATAATAGGTTTAATGGTTGGTGGTGTCGTTATCGCAAAAAGAG

AAGCTGACGCAGAAGCAGACGCCGAATTCAGACACGATTCAGGTTACGAA

GTTCACCATCAAAAATTGGTATTTTTCGCAGAAGATGTTGGTTCCAACAA

AGGTGCCATTATTGGTTTGATGGTTGGTGGTGTCGTCATTGCCAAGAGAG

AAGCTGAAGCTGAAGCCGACGCAGAATTCAGACACGACAGTGGTTATGAA

GTCCACCATCAAAAGTTGGTCTTTTTTGCTGAAGATGTTGGTTCTAACAA

AGGTGCAATCATAGGTTTGATGGTTGGTGGTGTAGTCATAGCAAAAGAG

AAGCAGACGCTGAAGCAGATGCCGAATTCAGACATGACAGTGGTTATGAA

GTTCATCACCAAAAATTAGTATTCTTCGCTGAAGATGTAGGTAGTAACAA

AGGTGCCATAATCGGTTTGATGGTCGGTGGTGTCGTTATAGCTTAAACCC

AGCTTTCTTGTACAAAGTGGTGCGGCCGCACTCGAG

Matα-Aβ42_6X Amino Acid Sequence
(SEQ ID NO: 57)
MRFPSIFTAVLFAASSALAAPVNTTTEDETAQIPAEAVIGYLDLEGDFDV

AVLPFSNSTNNGLLFINTTIASIAAKEEGVSLDKREAEADAEFRHDSGYE

VHHQKLVFFAEDVGSNKGAIIGLMVGGVVIAKREAEAEADAEFRHDSGYE

VHHQKLVFFAEDVGSNKGAIIGLMVGGVVIAKREADAEADAEFRHDSGYE

VHHQKLVFFAEDVGSNKGAIIGLMVGGVVIAKREADAEADAEFRHDSGYE

VHHQKLVFFAEDVGSNKGAIIGLMVGGVVIAKREADAEADAEFRHDSGYE

VHHQKLVFFAEDVGSNKGAIIGLMVGGVVIAKREADAEADAEFRHDSGYE

VHHQKLVFFAEDVGSNKGAIIGLMVGGVVIA

Matα-Aβ42_8X Nucleotide Sequence
(SEQ ID NO: 58)
GTCGACTGGATCCACAAGTTTGTACAAAAAAGCAGGCTACGGTACCTACA

AAATGAGATTCCCATCTATTTTCACCGCTGTTTTGTTTGCTGCTTCTTCT

GCTTTGGCTGCTCCAGTTAACACTACTACTGAAGATGAAACTGCTCAAAT

TCCAGCTGAAGCTGTTATTGGTTACTTGGATTTGGAAGGTGATTTCGATG

TTGCTGTTTTGCCATTCTCTAACTCTACCAACAATGGTTTGTTGTTCATC

AACACCACCATTGCTTCTATTGCTGCTAAAGAAGAAGGTGTCTCTTTGGA

TAAGAGAGAAGCTGAAGCAGACGCAGAATTCAGACATGATTCTGGTTATG

AAGTTCACCACCAAAAGTTGGTTTTCTTCGCTGAAGATGTTGGTTCTAAC

AAGGGTGCTATTATCGGTTTGATGGTTGGTGGTGTAGTTATTGCTAAAAG

AGAAGCCGAAGCTGAAGCTGATGCCGAATTCAGACACGATAGTGGTTACG

AAGTACATCATCAAAAATTAGTCTTTTTTGCCGAAGATGTCGGTAGTAAC

AAAGGTGCAATCATTGGTTTAATGGTCGGTGGTGTCGTAATAGCCAAGAG

AGAAGCAGACGCCGAAGCCGATGCAGAATTCAGACACGACTCCGGTTACG

AAGTCCATCACCAAAAGTTGGTATTCTTTGCCGAAGATGTCGGTTCAAAC

AAGGGTGCCATAATAGGTTTAATGGTTGGTGGTGTCGTTATCGCAAAAAG

AGAAGCTGACGCAGAAGCAGACGCCGAATTCAGACACGATTCAGGTTACG

AAGTTCACCATCAAAAATTGGTATTTTTCGCAGAAGATGTTGGTTCCAAC

AAAGGTGCCATTATTGGTTTGATGGTTGGTGGTGTCGTCATTGCCAAGAG

AGAAGCTGAAGCTGAAGCCGACGCAGAATTCAGACACGACAGTGGTTATG

AAGTCCACCATCAAAAGTTGGTCTTTTTTGCTGAAGATGTTGGTTCTAAC

AAAGGTGCAATCATAGGTTTGATGGTTGGTGGTGTAGTCATAGCAAAAGAG

AGAAGCAGACGCTGAAGCAGATGCCGAATTCAGACATGACAGTGGTTATG

```
AAGTTCATCACCAAAAATTAGTATTCTTCGCTGAAGATGTAGGTAGTAAC

AAAGGTGCCATAATCGGTTTGATGGTCGGTGGTGTCGTTATCGCTAAGAG

AGAAGCAGACGCTGAAGCTGACGCAGAATTCAGACATGACTCAGGTTACG

AAGTACACCATCAAAAGTTAGTATTCTTCGCCGAAGATGTAGGTTCAAAC

AAAGGTGCTATCATCGGTTTAATGGTTGGTGGTGTCGTAATTGCTAAAAG

AGAAGCTGAAGCCGAAGCAGATGCAGAATTCAGACATGATTCAGGTTACG

AAGTCCATCACCAAAAATTGGTCTTTTTCGCTGAAGATGTCGGTTCAAAC

AAGGGTGCAATTATTGGTTTGATGGTCGGTGGTGTAGTAATTGCCTAAAC

CCAGCTTTCTTGTACAAAGTGGTGCGGCCGCACTCGAG
```

Matα-Aβ42_8X Amino Acid Sequence
(SEQ ID NO: 59)
MRFPSIFTAVLFAASSALAAPVNTTTEDETAQIPAEAVIGYLDLEGDFDV
AVLPFSNSTNNGLLFINTTIASIAAKEEGVSLDKREAEADAEFRHDSGYE
VHHQKLVFFAEDVGSNKGAIIGLMVGGVVIAKREAEAEADAEFRHDSGYE
VHHQKLVFFAEDVGSNKGAIIGLMVGGVVIAKREADAEADAEFRHDSGYE
VHHQKLVFFAEDVGSNKGAIIGLMVGGVVIAKREAEAEADAEFRHDSGYE
VHHQKLVFFAEDVGSNKGAIIGLMVGGVVIAKREAEAEADAEFRHDSGYE
VHHQKLVFFAEDVGSNKGAIIGLMVGGVVIAKREAEAEADAEFRHDSGYE
VHHQKLVFFAEDVGSNKGAIIGLMVGGVVIAKREADAEADAEFRHDSGYE
VHHQKLVFFAEDVGSNKGAIIGLMVGGVVIA Matα-Aβ40_4X Nucleotide Sequence
(SEQ ID NO: 60)
```
GTCGACTGGATCCACAAGTTTGTACAAAAAAGCAGGCTGGTACCAAAGA

ATGAGATTCCCATCTATTTTCACCGCTGTTTTGTTTGCTGCTTCTTCTGC

TTTGGCTGCTCCAGTTAACACTACTACTGAAGATGAAACTGCTCAAATTC

CAGCTGAAGCTGTTATTGGTTACTTGGATTTGGAAGGTGATTTCGATGTT

GCTGTTTTGCCATTCTCTAACTCTACCAACAATGGTTTGTTGTTCATCAA

CACCACCATTGCTTCTATTGCTGCTAAAGAAGAAGGTGTCTCTTTGGATA

AGAGAGAAGCTGAAGCAGACGCAGAATTCAGACATGATTCTGGTTATGAA

GTTCACCACCAAAAGTTGGTTTTCTTCGCTGAAGATGTTGGTTCTAACAA

GGGTGCTATTATCGGTTTGATGGTTGGTGGTGTAGTAAAAAGAGAAGCCG

AAGCTGAAGCTGATGCCGAATTCAGACACGATAGTGGTTACGAAGTACAT

CATCAAAAATTAGTCTTTTTTGCCGAAGATGTCGGTAGTAACAAAGGTGC

AATCATTGGTTTAATGGTCGGTGGTGTCGTTAAGAGAAGCAGACGCCG

AAGCCGATGCAGAATTCAGACACGACTCCGGTTACGAAGTCCATCACCAA

AAGTTGGTATTCTTTGCCGAAGATGTCGGTTCAAACAAGGGTGCCATAAT

AGGTTTAATGGTTGGTGGTGTCGTCAAAGAGAAGCTGACGCTGAAGCAG

ACGCCGAATTCAGACACGACTCAGGTTATGAAGTACACCATCAAAAATTG

GTATTTTTCGCAGAAGATGTTGGTTCCAACAAAGGTGCCATTATTGGTTT

GATGGTTGGTGGTGTCGTTAAACCCAGCTTTCTTGTACAAAGTGGTGCG

GCCGCACTCGAG
```

Matα-Aβ40_6X Nucleotide Sequence
(SEQ ID NO: 62)
```
GTCGACTGGATCCACAAGTTTGTACAAAAAAGCAGGCTGGTACCAAAGA

ATGAGATTCCCATCTATTTTCACCGCTGTTTTGTTTGCTGCTTCTTCTGC

TTTGGCTGCTCCAGTTAACACTACTACTGAAGATGAAACTGCTCAAATTC

CAGCTGAAGCTGTTATTGGTTACTTGGATTTGGAAGGTGATTTCGATGTT

GCTGTTTTGCCATTCTCTAACTCTACCAACAATGGTTTGTTGTTCATCAA

CACCACCATTGCTTCTATTGCTGCTAAAGAAGAAGGTGTCTCTTTGGATA

AGAGAGAAGCTGAAGCAGACGCAGAATTCAGACATGATTCTGGTTATGAA

GTTCACCACCAAAAGTTGGTTTTCTTCGCTGAAGATGTTGGTTCTAACAA

GGGTGCTATTATCGGTTTGATGGTTGGTGGTGTAGTAAAAAGAGAAGCCG

AAGCTGAAGCTGATGCCGAATTCAGACACGATAGTGGTTACGAAGTACAT

CATCAAAAATTAGTCTTTTTTGCCGAAGATGTCGGTAGTAACAAAGGTGC

AATCATTGGTTTAATGGTCGGTGGTGTCGTTAAGAGAGAAGCAGACGCCG

AAGCCGATGCAGAATTCAGACACGACTCCGGTTACGAAGTCCATCACCAA

AAGTTGGTATTCTTTGCCGAAGATGTCGGTTCAAACAAGGGTGCCATAAT

AGGTTTAATGGTTGGTGGTGTCGTCAAAGAGAAGCTGACGCTGAAGCAG

ACGCCGAATTCAGACACGACTCAGGTTATGAAGTACACCATCAAAAATTG

GTATTTTTCGCAGAAGATGTTGGTTCCAACAAAGGTGCCATTATTGGTTT

GATGGTTGGTGGTGTCGTCAAGAGAGAAGCCGAAGCCGAAGCTGACGCAG

AATTCAGACATGACAGTGGTTACGAAGTCCACCATCAAAAGTTGGTCTTT

TTTGCTGAAGATGTTGGTTCTAACAAAGGTGCAATCATAGGTTTGATGGT

TGGTGGTGTAGTTAAGAGAGAAGCTGACGCTGAAGCTGATGCAGAATTCA

GACATGATTCAGGTTACGAAGTCCATCATCAAAAATTGGTTTTCTTCGCC

GAAGATGTAGGTTCAAACAAAGGTGCTATCATCGGTTTAATGGTTGGTGG

TGTCGTTTGAACCCAGCTTTCTTGTACAAAGTGGTGCGGCCGCACTCGAG
```

Matα-Aβ40_6X Amino Acid Sequence
(SEQ ID NO: 63)
MRFPSIFTAVLFAASSALAAPVNTTTEDETAQIPAEAVIGYLDLEGDFDV
AVLPFSNSTNNGLLFINTTIASIAAKEEGVSLDKREAEADAEFRHDSGYE
VHHQKLVFFAEDVGSNKGAIIGLMVGGVVKREAEAEADAEFRHDSGYEVH
HQKLVFFAEDVGSNKGAIIGLMVGGVVKREADAEADAEFRHDSGYEVHHQ
KLVFFAEDVGSNKGAIIGLMVGGVVKREADAEADAEFRHDSGYEVHHQKL
VFFAEDVGSNKGAIIGLMVGGVVKREAEAEADAEFRHDSGYEVHHQKLVF
FAEDVGSNKGAIIGLMVGGVVKREADAEADAEFRHDSGYEVHHQKLVFFA
EDVGSNKGAIIGLMVGGVV The following yeast expression constructs containing four copies (4X) of various Aβ42 mutants were also prepared.

Matα-Aβ42_4X_English Nucleotide Sequence
(SEQ ID NO: 64)
GTCGACTGGATCCACAAGTTTGTACAAAAAAGCAGGCTGGTACCAAAGA

ATGAGATTCCCATCTATTTTCACCGCTGTTTTGTTTGCTGCTTCTTCTGC

TTTGGCTGCTCCAGTTAACACTACTACTGAAGATGAAACTGCTCAAATTC

CAGCTGAAGCTGTTATTGGTTACTTGGATTTGGAAGGTGATTTCGATGTT

GCTGTTTTGCCATTCTCTAACTCTACCAACAATGGTTTGTTGTTCATCAA

CACCACCATTGCTTCTATTGCTGCTAAAGAAGAAGGTGTCTCTTTGGATA

AGAGAGAAGCTGAAGCAGACGCAGAATTTAGAAGAGATTCTGGTTACGAA

GTTCACCACCAAAAGTTGGTTTTTTTCGCTGAAGATGTCGGTTCTAACAA

GGGTGCTATTATTGGTTTGATGGTTGGTGGTGTCGTTATTGCTAAAAGAG

AAGCCGAAGCTGAAGCTGATGCCGAATTCAGAAGAGACTCAGGTTACGAA

GTACATCATCAAAAATTAGTATTCTTTGCCGAAGATGTTGGTAGTAACAA

AGGTGCAATCATCGGTTTAATGGTCGGTGGTGTAGTAATAGCCAAGAGAG

AAGCAGACGCCGAAGCCGACGCAGAATTCAGAAGAGATTCAGGTTACGAA

GTCCATCACCAAAAGTTAGTTTTCTTCGCAGAAGATGTCGGTTCAAACAA

AGGTGCCATAATAGGTTTAATGGTTGGTGGTGTAGTTATCGCTAAGAGAG

AAGCTGACGCTGAAGCAGATGCAGAATTCAGAAGAGACTCCGGTTACGAA

GTTCACCATCAAAAATTAGTCTTTTTCGCAGAAGATGTTGGTAGTAACAA

GGGTGCTATAATAGGTTTGATGGTCGGTGGTGTCGTCATAGCTTAAACCC

AGCTTTCTTGTACAAAGTGGTGCGGCCGCACTCGAG

Matα-Aβ42_4X_English Amino Acid Sequence
(SEQ ID NO: 65)
MRFPSIFTAVLFAASSALAAPVNTTTEDETAQIPAEAVIGYLDLEGDFDV

AVLPFSNSTNNGLLFINTTIASIAAKEEGVSLDKREAEADAEFRRDSGYE

VHHQKLVFFAEDVGSNKGAIIGLMVGGVVIAKREAEAEADAEFRRDSGYE

VHHQKLVFFAEDVGSNKGAIIGLMVGGVVIAKREADAEADAEFRRDSGYE

VHHQKLVFFAEDVGSNKGAIIGLMVGGVVIAKREADAEADAEFRRDSGYE

VHHQKLVFFAEDVGSNKGAIIGLMVGGVVIA

Matα-Aβ42_4X_F20E Nucleotide Sequence
(SEQ ID NO: 66)
GTCGACTGGATCCACAAGTTTGTACAAAAAAGCAGGCTGGTACCAAAGA

ATGAGATTCCCATCTATTTTCACCGCTGTTTTGTTTGCTGCTTCTTCTGC

TTTGGCTGCTCCAGTTAACACTACTACTGAAGATGAAACTGCTCAAATTC

CAGCTGAAGCTGTTATTGGTTACTTGGATTTGGAAGGTGATTTCGATGTT

GCTGTTTTGCCATTCTCTAACTCTACCAACAATGGTTTGTTGTTCATCAA

CACCACCATTGCTTCTATTGCTGCTAAAGAAGAAGGTGTCTCTTTGGATA

AGAGAGAAGCTGAAGCAGACGCAGAATTCAGACATGATTCTGGTTATGAA

GTTCACCACCAAAAGTTGGTTTTTGAAGCCGAAGATGTTGGTTCTAACAA

GGGTGCTATTATCGGTTTGATGGTTGGTGGTGTAGTTATTGCTAAAAGAG

AAGCCGAAGCTGAAGCTGATGCCGAATTCAGACACGATAGTGGTTACGAA

GTACATCATCAAAAATTAGTATTCGAAGCTGAAGATGTCGGTAGTAACAA

AGGTGCAATCATTGGTTTAATGGTCGGTGGTGTCGTAATAGCCAAGAGAG

AAGCAGACGCCGAAGCCGATGCAGAATTCAGACACGACTCCGGTTACGAA

GTCCATCACCAAAAGTTAGTCTTTGAAGCTGAAGATGTCGGTTCAAACAA

AGGTGCCATAATAGGTTTAATGGTTGGTGGTGTCGTTATCGCAAAAAGAG

AAGCTGACGCAGAAGCAGACGCCGAATTCAGACACGATTCAGGTTACGAA

GTTCACCATCAAAAATTGGTCTTTGAAGCTGAAGATGTTGGTAGTAACAA

GGGTGCCATAATAGGTTTGATGGTCGGTGGTGTAGTCATAGCTTAAACCC

AGCTTTCTTGTACAAAGTGGTGCGGCCGCACTCGAG

Matα-Aβ42_4X_F20E Amino Acid Sequence
(SEQ ID NO: 67)
MRFPSIFTAVLFAASSALAAPVNTTTEDETAQIPAEAVIGYLDLEGDFDV

AVLPFSNSTNNGLLFINTTIASIAAKEEGVSLDKREAEADAEFRHDSGYE

VHHQKLVFEAEDVGSNKGAIIGLMVGGVVIAKREAEAEADAEFRHDSGYE

VHHQKLVFEAEDVGSNKGAIIGLMVGGVVIAKREADAEADAEFRHDSGYE

VHHQKLVFEAEDVGSNKGAIIGLMVGGVVIAKREADAEADAEFRHDSGYE

VHHQKLVFEAEDVGSNKGAIIGLMVGGVVIA

Matα-Aβ42_4X_Flemish Nucleotide Sequence
(SEQ ID NO: 68)
GTCGACTGGATCCACAAGTTTGTACAAAAAAGCAGGCTGGTACCAAAGA

ATGAGATTCCCATCTATTTTCACCGCTGTTTTGTTTGCTGCTTCTTCTGC

TTTGGCTGCTCCAGTTAACACTACTACTGAAGATGAAACTGCTCAAATTC

CAGCTGAAGCTGTTATTGGTTACTTGGATTTGGAAGGTGATTTCGATGTT

GCTGTTTTGCCATTCTCTAACTCTACCAACAATGGTTTGTTGTTCATCAA

CACCACCATTGCTTCTATTGCTGCTAAAGAAGAAGGTGTCTCTTTGGATA

AGAGAGAAGCTGAAGCAGACGCAGAATTCAGACATGATTCTGGTTATGAA

GTTCACCACCAAAAGTTGGTTTTCTTCGGTGAAGATGTTGGTTCTAACAA

GGGTGCTATTATCGGTTTGATGGTTGGTGGTGTAGTTATTGCTAAAAGAG

AAGCCGAAGCTGAAGCTGATGCCGAATTCAGACACGATAGTGGTTACGAA

GTACATCATCAAAAATTAGTCTTTTTTGGTGAAGATGTCGGTAGTAACAA

AGGTGCCATAATTGGTTTAATGGTCGGTGGTGTCGTAATAGCCAAGAGAG

AAGCAGACGCCGAAGCCGATGCAGAATTCAGACACGACTCCGGTTACGAA

GTCCATCACCAAAAGTTGGTTTTTTTTGGTGAAGATGTCGGTTCCAACAA

GGGTGCAATCATAGGTTTAATGGTTGGTGGTGTCGTTATCGCAAAAAGAG

AAGCTGACGCAGAAGCAGACGCCGAATTCAGACACGATTCAGGTTACGAA

GTTCACCATCAAAAATTGGTATTCTTTGGTGAAGATGTAGGTTCAAACAA

AGGTGCCATCATTGGTTTGATGGTTGGTGGTGTCGTAATTGCCTAAACCC

AGCTTTCTTGTACAAAGTGGTGCGGCCGCACTCGAG

Matα-Aβ42_4X_Flemish Amino Acid Sequence
(SEQ ID NO: 69)
MRFPSIFTAVLFAASSALAAPVNTTTEDETAQIPAEAVIGYLDLEGDFDV

AVLPFSNSTNNGLLFINTTIASIAAKEEGVSLDKREAEADAEFRHDSGYE

VHHQKLVFFGEDVGSNKGAIIGLMVGGVVIAKREAEAEADAEFRHDSGYE

VHHQKLVFFGEDVGSNKGAIIGLMVGGVVIAKREADAEADAEFRHDSGYE

VHHQKLVFFGEDVGSNKGAIIGLMVGGVVIAKREADAEADAEFRHDSGYE

VHHQKLVFFGEDVGSNKGAIIGLMVGGVVIA

Matα-Aβ42_4X_Dutch Nucleotide Sequence
(SEQ ID NO: 70)
GTCGACTGGATCCACAAGTTTGTACAAAAAAGCAGGCTGGTACCAAAGA

ATGAGATTCCCATCTATTTTCACCGCTGTTTTGTTTGCTGCTTCTTCTGC

TTTGGCTGCTCCAGTTAACACTACTACTGAAGATGAAACTGCTCAAATTC

CAGCTGAAGCTGTTATTGGTTACTTGGATTTGGAAGGTGATTTCGATGTT

GCTGTTTTGCCATTCTCTAACTCTACCAACAATGGTTTGTTGTTCATCAA

CACCACCATTGCTTCTATTGCTGCTAAAGAAGAAGGTGTCTCTTTGGATA

AGAGAGAAGCTGAAGCAGACGCAGAATTCAGACATGATTCTGGTTATGAA

GTTCACCACCAAAGTTGGTTTTCTTCGCTCAAGATGTTGGTTCTAACAA

GGGTGCTATTATCGGTTTGATGGTTGGTGGTGTAGTTATTGCTAAAAGAG

AAGCCGAAGCTGAAGCTGATGCCGAATTCAGACACGATAGTGGTTACGAA

GTACATCATCAAAAATTAGTCTTTTTCGCCCAAGACGTCGGTAGTAACAA

AGGTGCAATCATTGGTTTAATGGTCGGTGGTGTCGTAATAGCCAAGAGAG

AAGCAGACGCCGAAGCCGATGCAGAATTCAGACACGACTCCGGTTACGAA

GTCCATCACCAAAAGTTGGTATTTTTTGCCCAAGACGTAGGTTCAAACAA

GGGTGCCATAATAGGTTTAATGGTTGGTGGTGTCGTTATCGCAAAAAGAG

AAGCTGACGCAGAAGCAGACGCCGAATTCAGACACGATTCAGGTTACGAA

GTTCACCATCAAAAATTGGTATTCTTTGCCCAAGATGTTGGTTCCAACAA

AGGTGCCATTATTGGTTTGATGGTTGGTGGTGTCGTCATAGCTTAAACCC

AGCTTTCTTGTACAAAGTGGTGCGGCCGCACTCGAG

Matα-Aβ42_4X_Dutch Amino Acid Sequence
(SEQ ID NO: 71)
MRFPSIFTAVLFAASSALAAPVNTTTEDETAQIPAEAVIGYLDLEGDFDV

AVLPFSNSTNNGLLFINTTIASIAAKEEGVSLDKREAEADAEFRHDSGYE

VHHQKLVFFAQDVGSNKGAIIGLMVGGVVIAKREAEADAEFRHDSGYE

VHHQKLVFFAQDVGSNKGAIIGLMVGGVVIAKREADAEADAEFRHDSGYE

VHHQKLVFFAQDVGSNKGAIIGLMVGGVVIAKREADAEADAEFRHDSGYE

VHHQKLVFFAQDVGSNKGAIIGLMVGGVVIA

Matα-Aβ42_4X_Italian Nucleotide Sequence
(SEQ ID NO: 72)
GTCGACTGGATCCACAAGTTTGTACAAAAAAGCAGGCTGGTACCAAAGA

ATGAGATTCCCATCTATTTTCACCGCTGTTTTGTTTGCTGCTTCTTCTGC

TTTGGCTGCTCCAGTTAACACTACTACTGAAGATGAAACTGCTCAAATTC

CAGCTGAAGCTGTTATTGGTTACTTGGATTTGGAAGGTGATTTCGATGTT

GCTGTTTTGCCATTCTCTAACTCTACCAACAATGGTTTGTTGTTCATCAA

CACCACCATTGCTTCTATTGCTGCTAAAGAAGAAGGTGTCTCTTTGGATA

AGAGAGAAGCTGAAGCAGACGCAGAATTCAGACATGATTCTGGTTATGAA

GTTCACCACCAAAAGTTGGTTTTCTTCGCTAAAGATGTCGGTTCTAACAA

GGGTGCTATTATCGGTTTGATGGTTGGTGGTGTAGTTATTGCTAAAAGAG

AAGCCGAAGCTGAAGCTGATGCCGAATTCAGACACGATAGTGGTTACGAA

GTACATCATCAAAAATTAGTCTTTTTCGCCAAGGACGTCGGTAGTAACAA

AGGTGCAATCATTGGTTTAATGGTCGGTGGTGTCGTAATAGCCAAGAGAG

AAGCAGACGCCGAAGCCGATGCAGAATTCAGACACGACTCCGGTTACGAA

GTCCATCACCAAAAGTTGGTATTTTTTGCCAAGGACGTTGGTTCAAACAA

GGGTGCCATAATAGGTTTAATGGTTGGTGGTGTCGTTATCGCAAAAAGAG

AAGCTGACGCAGAAGCAGACGCCGAATTCAGACACGATTCAGGTTACGAA

GTTCACCATCAAAAATTGGTATTCTTTGCCAAAGATGTAGGTAGTAACAA

GGGTGCCATAATTGGTTTGATGGTCGGTGGTGTAGTCATAGCTTAAACCC

AGCTTTCTTGTACAAAGTGGTGCGGCCGCACTCGAG

Matα-Aβ42_4X_Italian Amino Acid Sequence
(SEQ ID NO: 73)
MRFPSIFTAVLFAASSALAAPVNTTTEDETAQIPAEAVIGYLDLEGDFDV

AVLPFSNSTNNGLLFINTTIASIAAKEEGVSLDKREAEADAEFRHDSGYE

VHHQKLVFFAKDVGSNKGAIIGLMVGGVVIAKREAEADAEFRHDSGYE

VHHQKLVFFAKDVGSNKGAIIGLMVGGVVIAKREADAEADAEFRHDSGYE

VHHQKLVFFAKDVGSNKGAIIGLMVGGVVIAKREADAEADAEFRHDSGYE

VHHQKLVFFAKDVGSNKGAIIGLMVGGVVIA

Matα-Aβ42_4X_Arctic Nucleotide Sequence
(SEQ ID NO: 74)
GTCGACTGGATCCACAAGTTTGTACAAAAAAGCAGGCTGGTACCAAAGA

ATGAGATTCCCATCTATTTTCACCGCTGTTTTGTTTGCTGCTTCTTCTGC

TTTGGCTGCTCCAGTTAACACTACTACTGAAGATGAAACTGCTCAAATTC

CAGCTGAAGCTGTTATTGGTTACTTGGATTTGGAAGGTGATTTCGATGTT

GCTGTTTTGCCATTCTCTAACTCTACCAACAATGGTTTGTTGTTCATCAA

CACCACCATTGCTTCTATTGCTGCTAAAGAAGAAGGTGTCTCTTTGGATA

AGAGAGAAGCTGAAGCAGACGCAGAATTCAGACATGATTCTGGTTATGAA

GTTCACCACCAAAGTTGGTTTTTTTCGCTGGTGATGTTGGTTCTAACAA

GGGTGCTATTATTGGTTTGATGGTTGGTGGTGTCGTTATTGCTAAAAGAG

AAGCCGAAGCTGAAGCTGATGCCGAATTCAGACACGATAGTGGTTACGAA

GTACATCATCAAAAATTAGTTTTCTTTGCCGGTGACGTCGGTAGTAACAA

AGGTGCAATCATAGGTTTAATGGTCGGTGGTGTAGTCATAGCCAAGAGAG

AAGCAGACGCCGAAGCCGATGCAGAATTCAGACACGACTCCGGTTACGAA

GTCCATCACCAAAAGTTGGTATTCTTTGCCGGTGACGTAGGTTCAAACAA

GGGTGCCATAATCGGTTTAATGGTTGGTGGTGTAGTAATCGCAAAAAGAG

AAGCTGACGCTGAAGCAGACGCCGAATTCAGACACGACTCAGGTTATGAA

GTACACCATCAAAAATTGGTCTTTTTCGCCGGTGATGTAGGTAGTAACAA

GGGTGCAATTATCGGTTTGATGGTCGGTGGTGTAGTTATCGCTTAAACCC

AGCTTTCTTGTACAAAGTGGTGCGGCCGCACTCGAG

Matα-Aβ42_4X_Arctic Amino Acid Sequence
(SEQ ID NO: 75)
MRFPSIFTAVLFAASSALAAPVNTTTEDETAQIPAEAVIGYLDLEGDFDV

AVLPFSNSTNNGLLFINTTIASIAAKEEGVSLDKREAEADAEFRHDSGYE

VHHQKLVFFAGDVGSNKGAIIGLMVGGVVIAKREAEADAEFRHDSGYE

VHHQKLVFFAGDVGSNKGAIIGLMVGGVVIAKREADAEADAEFRHDSGYE

VHHQKLVFFAGDVGSNKGAIIGLMVGGVVIAKREADAEADAEFRHDSGYE

VHHQKLVFFAGDVGSNKGAIIGLMVGGVVIA

Matα-Aβ42_4X_E22G(Arctic)/I31E Nucleotide Sequence
(SEQ ID NO: 76)
GTCGACTGGATCCACAAGTTTGTACAAAAAAGCAGGCTGGTACCAAAGA

ATGAGATTCCCATCTATTTTCACCGCTGTTTTGTTTGCTGCTTCTTCTGC

TTTGGCTGCTCCAGTTAACACTACTACTGAAGATGAAACTGCTCAAATTC

CAGCTGAAGCTGTTATTGGTTACTTGGATTTGGAAGGTGATTTCGATGTT

GCTGTTTTGCCATTCTCTAACTCTACCAACAATGGTTTGTTGTTCATCAA

CACCACCATTGCTTCTATTGCTGCTAAAGAAGAAGGTGTCTCTTTGGATA

GAGAGAAGCTGAAGCAGACGCAGAATTCAGACATGATTCTGGTTATGAA

GTTCACCACCAAAGTTGGTTTTTTTCGCTGGTGATGTTGGTTCTAACAA

GGGTGCTGAAATTGGTTTGATGGTTGGTGGTGTAGTTATTGCTAAAAGAG

AAGCCGAAGCTGAAGCTGATGCCGAATTCAGACACGATAGTGGTTACGAA

GTACATCATCAAAAATTAGTTTTCTTTGCCGGTGACGTCGGTAGTAACAA

AGGTGCAGAAATAGGTTTAATGGTCGGTGGTGTCGTAATAGCCAAGAGAG

AAGCAGACGCCGAAGCCGATGCAGAATTCAGACACGACTCCGGTTACGAA

GTCCATCACCAAAGTTGGTATTCTTTGCCGGTGACGTAGGTTCAAACAA

GGGTGCAGAAATCGGTTTAATGGTTGGTGGTGTAGTCATAGCAAAGAGAG

AAGCTGACGCTGAAGCAGACGCCGAATTCAGACACGACTCAGGTTATGAA

GTACACCATCAAAAATTGGTCTTTTTCGCCGGTGATGTAGGTAGTAACAA

GGGTGCCGAAATCGGTTTGATGGTCGGTGGTGTCGTTATCGCTTAAACCC

AGCTTTCTTGTACAAAGTGGTGCGGCCGCACTCGAG

Matα-Aβ42_4X_E22G/I31E Amino Acid Sequence
(SEQ ID NO: 77)
MRFPSIFTAVLFAASSALAAPVNTTTEDETAQIPAEAVIGYLDLEGDFDV

AVLPFSNSTNNGLLFINTTIASIAAKEEGVSLDKREAEADAEFRHDSGYE

VHHQKLVFFAGDVGSNKGAEIGLMVGGVVIAKREAEADAEFRHDSGYE

VHHQKLVFFAGDVGSNKGAEIGLMVGGVVIAKREADAEADAEFRHDSGYE

VHHQKLVFFAGDVGSNKGAEIGLMVGGVVIAKREADAEADAEFRHDSGYE

VHHQKLVFFAGDVGSNKGAEIGLMVGGVVIA

Matα-Aβ42_4X_E22del Nucleotide Sequence
(SEQ ID NO: 78)
GTCGACTGGATCCACAAGTTTGTACAAAAAAGCAGGCTGGTACCAAAGA

ATGAGATTCCCATCTATTTTCACCGCTGTTTTGTTTGCTGCTTCTTCTGC

TTTGGCTGCTCCAGTTAACACTACTACTGAAGATGAAACTGCTCAAATTC

CAGCTGAAGCTGTTATTGGTTACTTGGATTTGGAAGGTGATTTCGATGTT

GCTGTTTTGCCATTCTCTAACTCTACCAACAATGGTTTGTTGTTCATCAA

CACCACCATTGCTTCTATTGCTGCTAAAGAAGAAGGTGTCTCTTTGGATA

GAGAGAAGCTGAAGCAGACGCAGAATTCAGACATGATTCTGGTTATGAA

GTTCACCACCAAAGTTGGTTTTCTTCGCTGATGTTGGTTCTAACAAGGGT

GCTATTATCGGTTTGATGGTTGGTGGTGTAGTTATTGCTAAAAGAGAAG

CCGAAGCTGAAGCTGATGCCGAATTCAGACACGATAGTGGTTACGAAGTA

CATCATCAAAAATTAGTCTTTTTCGCCGATGTCGGTAGTAACAAAGGTGC

AATCATAGGTTTAATGGTCGGTGGTGTAGTCATAGCCAAGAGAGAAGCAG

ACGCCGAAGCCGATGCAGAATTCAGACACGACTCCGGTTACGAAGTCCAT

CACCAAAGTTGGTATTTTTGCCGACGTAGGTTCAAACAAAGGTGCCAT

AATCGGTTTAATGGTTGGTGGTGTAGTAATCGCAAAAAGAGAAGCTGACG

CTGAAGCAGACGCCGAATTCAGACACGACTCAGGTTATGAAGTACACCAT

CAAAAATTGGTATTCTTTGCTGACGTTGGTAGTAACAAGGGTGCCATAAT

AGGTTTGATGGTCGGTGGTGTCGTAATCGCTTAAACCCAGCTTTCTTGTA

CAAAGTGGTGCGGCCGCACTCGAG

Matα-Aβ42_4X_E22del Amino Acid Sequence
(SEQ ID NO: 79)
MRFPSIFTAVLFAASSALAAPVNTTTEDETAQIPAEAVIGYLDLEGDFDV

AVLPFSNSTNNGLLFINTTIASIAAKEEGVSLDKREAEADAEFRHDSGYE

VHHQKLVFFADVGSNKGAIIGLMVGGVVIAKREAEADAEFRHDSGYEV

HHQKLVFFADVGSNKGAIIGLMVGGVVIAKREADAEADAEFRHDSGYEVH

HQKLVFFADVGSNKGAIIGLMVGGVVIAKREADAEADAEFRHDSGYEVHH

QKLVFFADVGSNKGAIIGLMVGGVVIA

Matα-Aβ42_4X_Iowa Nucleotide Sequence
(SEQ ID NO: 80)
GTCGACTGGATCCACAAGTTTGTACAAAAAAGCAGGCTGGTACCAAAGA

ATGAGATTCCCATCTATTTTCACCGCTGTTTTGTTTGCTGCTTCTTCTGC

TTTGGCTGCTCCAGTTAACACTACTACTGAAGATGAAACTGCTCAAATTC

CAGCTGAAGCTGTTATTGGTTACTTGGATTTGGAAGGTGATTTCGATGTT

GCTGTTTTGCCATTCTCTAACTCTACCAACAATGGTTTGTTGTTCATCAA

CACCACCATTGCTTCTATTGCTGCTAAAGAAGAAGGTGTCTCTTTGGATA

GAGAGAAGCTGAAGCAGACGCAGAATTCAGACATGATTCTGGTTATGAA

GTTCACCACCAAAGTTGGTTTTCTTCGCTGAAAATGTCGGTTCTAACAA

GGGTGCTATTATCGGTTTGATGGTTGGTGGTGTAGTTATTGCTAAAAGAG

AAGCCGAAGCTGAAGCTGATGCCGAATTCAGACACGATAGTGGTTACGAA

GTACATCATCAAAAATTAGTCTTTTTCGCCGAAAACGTTGGTAGTAACAA

AGGTGCAATCATTGGTTTAATGGTCGGTGGTGTCGTAATAGCCAAGAGAG

AAGCAGACGCCGAAGCCGATGCAGAATTCAGACACGACTCCGGTTACGAA

GTCCATCACCAAAGTTGGTATTTTTGCCGAAAACGTTGGTTCAAACAA

GGGTGCCATAATAGGTTTAATGGTTGGTGGTGTCGTTATCGCAAAAAGAG

AAGCTGACGCAGAAGCAGACGCCGAATTCAGACACGATTCAGGTTACGAA

GTTCACCATCAAAAATTGGTATTCTTCGCAGAAAACGTTGGTTCCAACAA

AGGTGCTATTATTGGTTTAATGGTTGGTGGTGTCGTCATTGCTTAAACCC

AGCTTTCTTGTACAAAGTGGTGCGGCCGCACTCGAG

Matα-Aβ42_4X_Iowa Amino Acid Sequence
(SEQ ID NO: 81)
MRFPSIFTAVLFAASSALAAPVNTTTEDETAQIPAEAVIGYLDLEGDFDV

AVLPFSNSTNNGLLFINTTIASIAAKEEGVSLDKREAEADAEFRHDSGYE

VHHQKLVFFAENVGSNKGAIIGLMVGGVVIAKREAEADAEFRHDSGYE

VHHQKLVFFAENVGSNKGAIIGLMVGGVVIAKREADAEADAEFRHDSGYE

-continued
VHHQKLVFFAENVGSNKGAIIGLMVGGVVIAKREADAEADAEFRHDSGYE

VHHQKLVFFAENVGSNKGAIIGLMVGGVVIA

Matα-Aβ42_4X_Tottori Nucleotide Sequence
(SEQ ID NO: 82)
GTCGACTGGATCCACAAGTTTGTACAAAAAAGCAGGCTGGTACCAAAAGA

ATGAGATTCCCATCTATTTTCACCGCTGTTTTGTTTGCTGCTTCTTCTGC

TTTGGCTGCTCCAGTTAACACTACTACTGAAGATGAAACTGCTCAAATTC

CAGCTGAAGCTGTTATTGGTTACTTGGATTTGGAAGGTGATTTCGATGTT

GCTGTTTTGCCATTCTCTAACTCTACCAACAATGGTTTGTTGTTCATCAA

CACCACCATTGCTTCTATTGCTGCTAAAGAAGAAGGTGTCTCTTTGGATA

AGAGAGAAGCTGAAGCAGACGCAGAATTCAGACATAATTCTGGTTACGAA

GTTCACCACCAAAAGTTGGTTTTTTTCGCTGAAGATGTCGGTTCTAACAA

GGGTGCTATTATTGGTTTGATGGTTGGTGGTGTCGTTATTGCTAAAAGAG

AAGCCGAAGCTGAAGCTGATGCCGAATTCAGACACAATAGTGGTTATGAA

GTCCATCATCAAAAATTAGTTTTCTTTGCCGAAGATGTTGGTAGTAACAA

AGGTGCAATCATCGGTTTAATGGTCGGTGGTGTAGTAATAGCCAAGAGAG

AAGCAGACGCCGAAGCCGATGCAGAATTCAGACACAACTCCGGTTATGAA

GTACATCACCAAAAGTTAGTCTTTTTCGCCGAAGATGTTGGTTCAAACAA

AGGTGCCATTATAGGTTTAATGGTTGGTGGTGTAGTTATCGCTAAGAGAG

AAGCTGACGCTGAAGCAGACGCCGAATTCAGACACAACTCAGGTTACGAA

GTCCACCATCAAAAATTGGTATTCTTCGCAGAAGATGTAGGTAGTAACAA

GGGTGCCATAATAGGTTTGATGGTCGGTGGTGTCGTCATAGCTTAAACCC

AGCTTTCTTGTACAAAGTGGTGCGGCCGCACTCGAG

Matα-Aβ42_4X_Tottori Amino Acid Sequence
(SEQ ID NO: 83)
MRFPSIFTAVLFAASSALAAPVNTTTEDETAQIPAEAVIGYLDLEGDFDV

AVLPFSNSTNNGLLFINTTIASIAAKEEGVSLDKREAEADAEFRHNSGYE

VHHQKLVFFAEDVGSNKGAIIGLMVGGVVIAKREAEADAEFRHNSGYE

VHHQKLVFFAEDVGSNKGAIIGLMVGGVVIAKREADAEADAEFRHNSGYE

VHHQKLVFFAEDVGSNKGAIIGLMVGGVVIAKREADAEADAEFRHNSGYE

VHHQKLVFFAEDVGSNKGAIIGLMVGGVVIA

The Aβ sequence was codon optimized for expression in yeast. The Aβ expression construct consists of attB Gateway flanking regions at the 5' and 3' ends (nucleotides ACAAGTTTGTACAAAAAAGCAGGCT (SEQ ID NO:84) and ACCCAGCTTTCTTGTACAAAGTGGT (SEQ ID NO:85), respectively) for Gateway cloning of MatαPrepro-Aβ42 sequence. The entire construct was synthesized into pUC57-Kan plasmid and cloned into the Gateway entry vector pDONR221. These constructs were then transferred into the pAG425Galexpression vector by Gateway LR cloning (Alberti et al., "A suite of Gateway cloning vectors for high throughput genetic analysis in *Saccharomyces cerevisiae*," Yeast 24:913 (2007)). The GAL1 promoter enables expression of Aβ fusion transgenes under galactose-inducible conditions. The vector has an ampicillin resistant gene for amplification of the vector in *E. coli* and leucine auxotrophic marker (LEU2) for selection of transformed yeast cells on media lacking leucine (FIG. 2).

Yeast cells transformed with either an expression vector containing galactose-inducible green fluorescent protein (GFP) or a galactose-inducible expression plasmid encoding a yeast mating factor alpha signal sequence/human amyloid beta 1-42 (Aβ42) or 1-40 (Aβ40) or scrambled Aβ42 fusion polypeptide were grown on glucose or galactose containing synthetic media and growth was assessed. Transformed cells were selected in medium lacking leucine. Individual transformants were grown overnight in complete synthetic medium (CSM) lacking leucine with 2% raffinose as the carbon source. Cell concentrations (OD600) were adjusted in a 96-well plate to OD 0.5 or 1. Cells were then 5-fold serially diluted and spotted on SD media containing glucose (uninduced) and galactose (induced). Plates were incubated at 30° C. for 2 days (glucose) or 3 to 4 days (galactose).

Figure 3:
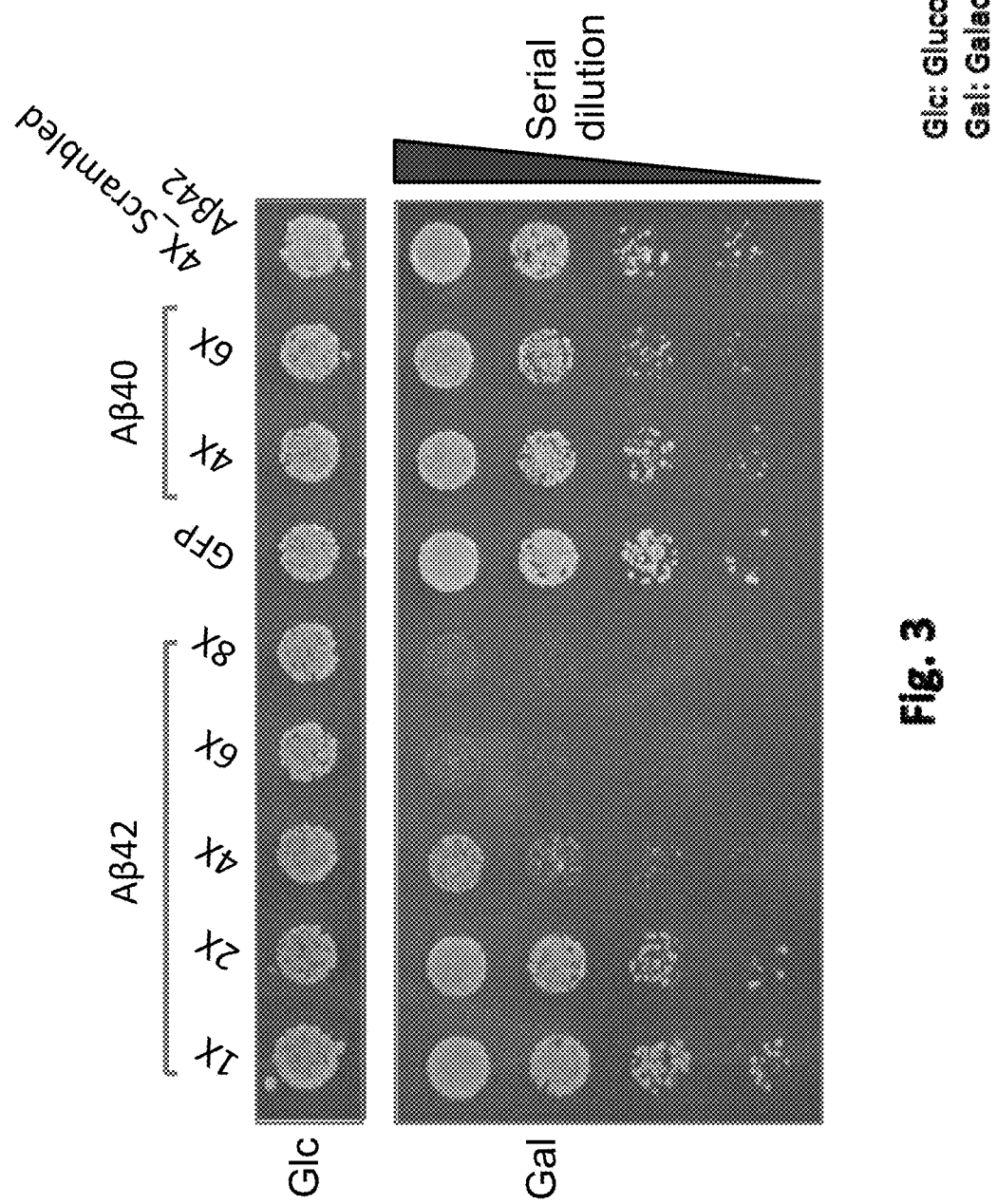
FIG. 3 is a series of photographs depicting yeast toxicity resulting from expression of constructs containing varying numbers of copies of Aβ42 or Aβ40.

The experimental and control transformants grew equally well on glucose containing media (uninduced), whereas amyloid beta expression in galactose containing media (induced) profoundly inhibited cell growth in a dose number-dependent manner (FIG. 3). Expression of a single copy Aβ42 (1X) on a 2μ high-copy expression plasmid was not toxic, whereas increased Aβ42 copy number (2, 4, 6 and 8-copies) on the same expression plasmid yielded toxicity in transformed cells in a dose-dependent manner (FIG. 3). Expression of Aβ40 (4 and 6 copies) did not produce significant toxicity as compared to the similar copy number of Aβ42 (FIG. 3). The control expression construct of scrambled Aβ42 (4 copies), in which the amino acid sequence of Aβ42 was randomly scrambled, did not produce significant toxicity (FIG. 3).

Figure 4:
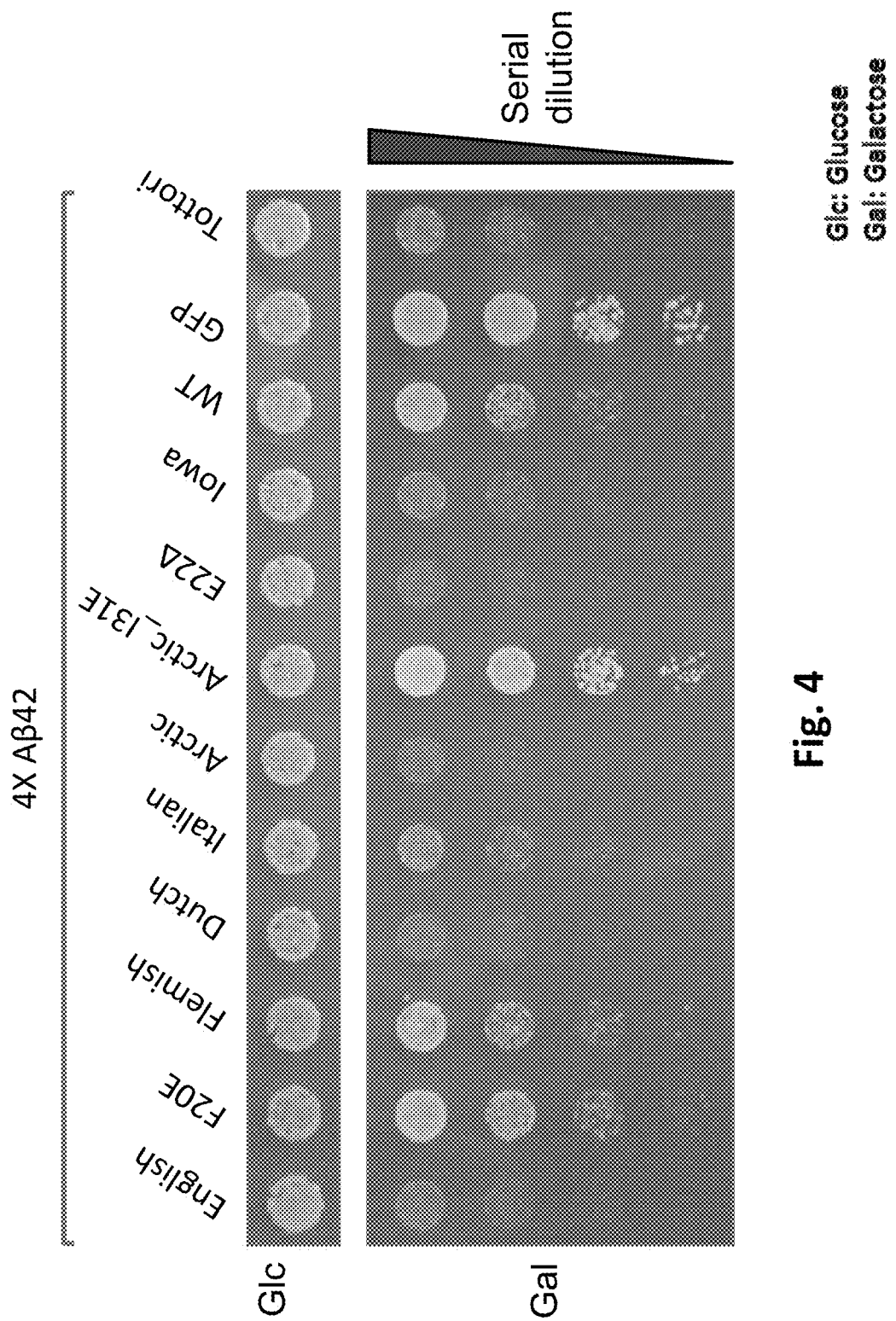
FIG. 4 is a series of photographs depicting yeast toxicity resulting from expression of constructs containing four copies of various Aβ42 mutants.

Yeast cells were transformed with galactose-inducible expression vector (pAG425Gal) harboring different mutations in Aβ (4 copies). Among these were nine disease-related mutations: English (H6R), Tottori (D7N), Flemish (A21G), Dutch (E22Q), Italian (E22K), Arctic (E22G), E22_deletion, Iowa (D23N), and "wild-type" and two detoxifying mutations: F20E and Arctic_I31E. Growth of transformed yeast cells was tested under induced (galactose) and uninduced (glucose) conditions. Different Aβ mutations caused varying degrees of toxicity upon expression under galactose induction (FIG. 4). For example, the Arctic, E22_deletion, and Dutch mutations caused profound toxicity whereas Arctic_I31E and F20E mutations caused significantly lower amount of toxicity (FIG. 4).

Example 2: Amyloid Beta Expression Constructs for Mammalian Cells

Figure 5:
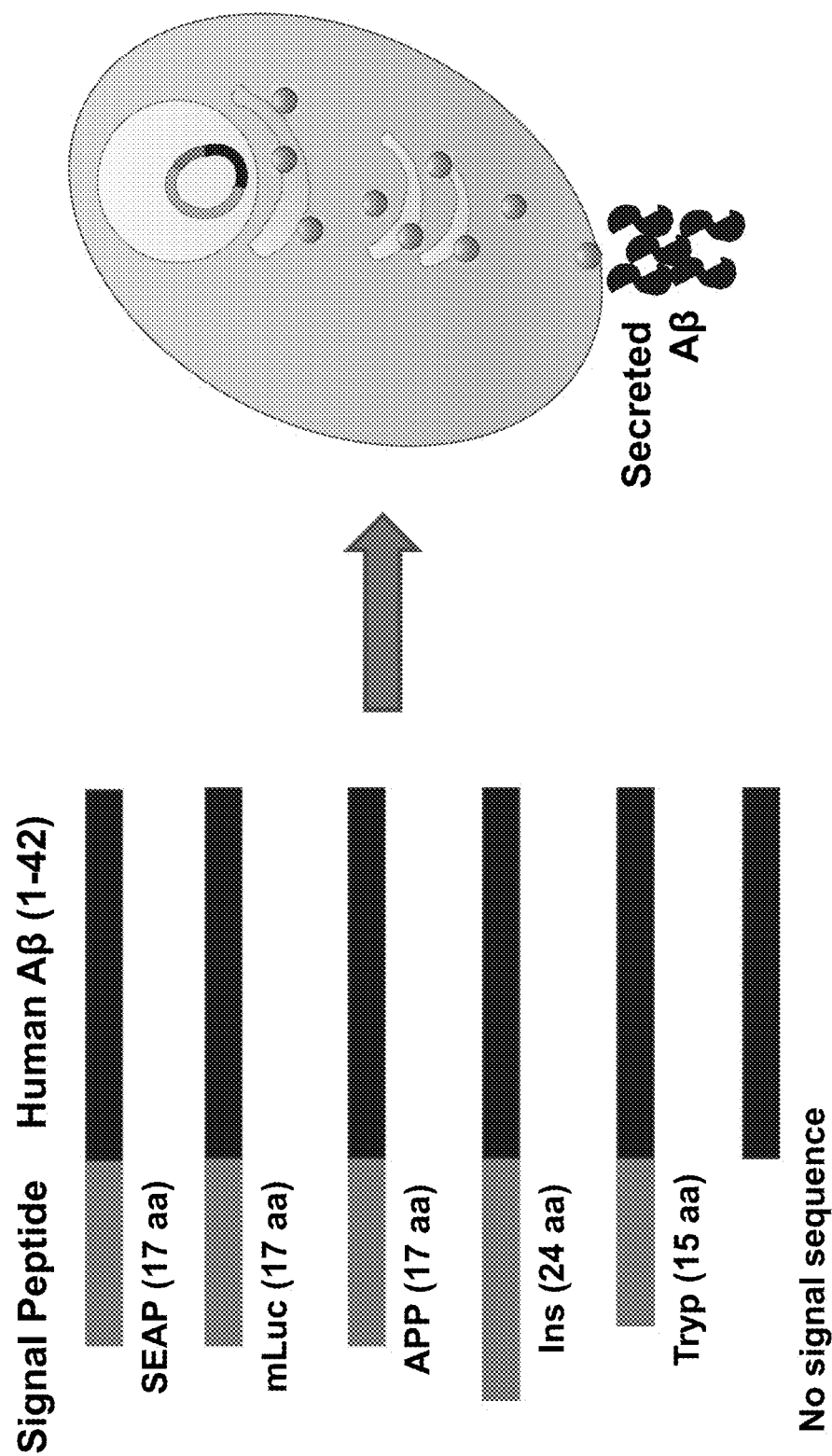
FIG. 5 depicts mammalian Aβ42 expression constructs containing the signal sequences of human insulin (Ins), human trypsin (Tryp), human amyloid precursor protein (APP), human placental secreted alkaline phosphatase (SEAP), or *Metridia* luciferase (mLuc) of the marine copepod *Metridia longa* fused to Aβ42.

A human Aβ sequence was fused at the C-terminus of the signal sequence of several eukaryotic secretory proteins. The signal sequences were human insulin (Ins), human trypsin (Tryp), human amyloid precursor protein (APP), human placental secreted alkaline phosphatase (SEAP) and *Metridia* luciferase (mLuc) of the marine copepod *Metridia longa*. The Aβ peptide was fused to these signal peptides without any linker in between the sequences (FIG. 5). For cytoplasmic expression, human Aβ peptide without any secretory signal was also constructed in similar expression vector (labeled "no signal sequence" in FIG. 5).

The nucleotide and amino acid sequences of the fusion polypeptides encoded by the expression constructs are as follows.

SEAP-Aβ42_1X Nucleotide Sequence
(SEQ ID NO: 86)
CACCATGCTGCTGCTGCTGCTGCTGCTGGGCCTGAGGCTACAGCTCTCCC

TGGGCGATGCGGAATTTCGCCATGATTCTGGCTATGAAGTGCATCATCAG

-continued

AAACTGGTGTTTTTTGCGGAAGATGTGGGCTCTAACAAAGGCGCGATTAT

TGGCCTGATGGTGGGCGGCGTGGTGATTGCGTAA

SEAP-Aβ42_1X Amino Acid Sequence
(SEQ ID NO: 87)
MLLLLLLLGLRLQLSLGDAEFRHDSGYEVHHQKLVFFAEDVGSNKGAIIG

LMVGGVVIA mLuc-Aβ42_1X Amino Acid Sequence
(SEQ ID NO: 88)
CACCATGGACATCAAGGTGGTGTTCACCCTGGTGTTCAGCGCCCTGGTGC

AGGCCGATGCGGAATTTCGCCATGATTCTGGCTATGAAGTGCATCATCAG

AAACTGGTGTTTTTTGCGGAAGATGTGGGCTCTAACAAAGGCGCGATTAT

TGGCCTGATGGTGGGCGGCGTGGTGATTGCGTAA mLuc-Aβ42_1X Amino Acid Sequence
(SEQ ID NO: 89)
MDIKVVFTLVFSALVQADAEFRHDSGYEVHHQKLVFFAEDVGSNKGAIIG

LMVGGVVIA

APP-Aβ42_1X Nucleotide Sequence
(SEQ ID NO: 90)
CACCATGCTGCCCGGTTTGGCACTGCTCCTGCTGGCCGCCTGGACGGCTC

GGGCGGATGCGGAATTTCGCCATGATTCTGGCTATGAAGTGCATCATCAG

AAACTGGTGTTTTTTGCGGAAGATGTGGGCTCTAACAAAGGCGCGATTAT

TGGCCTGATGGTGGGCGGCGTGGTGATTGCGTAA

APP-Aβ42_1X Amino Acid Sequence
(SEQ ID NO: 91)
MLPGLALLLLAAWTARADAEFRHDSGYEVHHQKLVFFAEDVGSNKGAIIG

LMVGGVVIA

Ins-Aβ42_1X Nucleotide Sequence
(SEQ ID NO: 92)
CACCATGGCCCTGTGGATGCGCCTCCTGCCCCTGCTGGCGCTGCTGGCCC

TCTGGGGACCTGACCCAGCCGCAGCCGATGCGGAATTTCGCCATGATTCT

GGCTATGAAGTGCATCATCAGAAACTGGTGTTTTTTGCGGAAGATGTGGG

CTCTAACAAAGGCGCGATTATTGGCCTGATGGTGGGCGGCGTGGTGATTG

CGTAA

Ins-Aβ42_1X Amino Acid Sequence
(SEQ ID NO: 93)
MALWMRLLPLLALLALWGPDPAAADAEFRHDSGYEVHHQKLVFFAEDVG

SNKGAIIGLMVGGVVIA

Tryp-Aβ42_1X Nucleotide Sequence
(SEQ ID NO: 94)
CACCATGTCTGCACTTCTGATCCTAGCTCTTGTTGGAGCTGCAGTTGCTG

ATGCGGAATTTCGCCATGATTCTGGCTATGAAGTGCATCATCAGAAACTG

GTGTTTTTTGCGGAAGATGTGGGCTCTAACAAAGGCGCGATTATTGGCCT

GATGGTGGGCGGCGTGGTGATTGCGTAA

Tryp-Aβ42_1X Amino Acid Sequence
(SEQ ID NO: 95)
MSALLILALVGAAVADAEFRHDSGYEVHHQKLVFFAEDVGSNKGAIIGLM

VGGVVIA

NSP-Aβ42_1X Nucleotide Sequence
(SEQ ID NO: 96)
CACCATGGATGCGGAATTTCGCCATGATTCTGGCTATGAAGTGCATCATC

AGAAACTGGTGTTTTTTGCGGAAGATGTGGGCTCTAACAAAGGCGCGATT

ATTGGCCTGATGGTGGGCGGCGTGGTGATTGCGTAA

NSP-Aβ42_1X Amino Acid Sequence
(SEQ ID NO: 97)
MDAEFRHDSGYEVHHQKLVFFAEDVGSNKGAIIGLMVGGVVIA The following mammalian expression construct encoding Aβ40 was also prepared.

Ins-Aβ40_1X Nucleotide Sequence
(SEQ ID NO: 98)
CACCATGGCCCTGTGGATGCGCCTCCTGCCCCTGCTGGCGCTGCTGGCC

CTCTGGGGACCTGACCCAGCCGCAGCCGATGCGGAATTTCGCCATGATT

CTGGCTATGAAGTGCATCATCAGAAACTGGTGTTTTTTGCGGAAGATGT

GGGCTCTAACAAAGGCGCGATTATTGGCCTGATGGTGGGCGGCGTGGTG

TAA

Ins-Aβ40_1X Amino Acid Sequence
(SEQ ID NO: 99)
MALWMRLLPLLALLALWGPDPAAADAEFRHDSGYEVHHQKLVFFAEDVG

SNKGAIIGLMVGGVV

Figure 6:
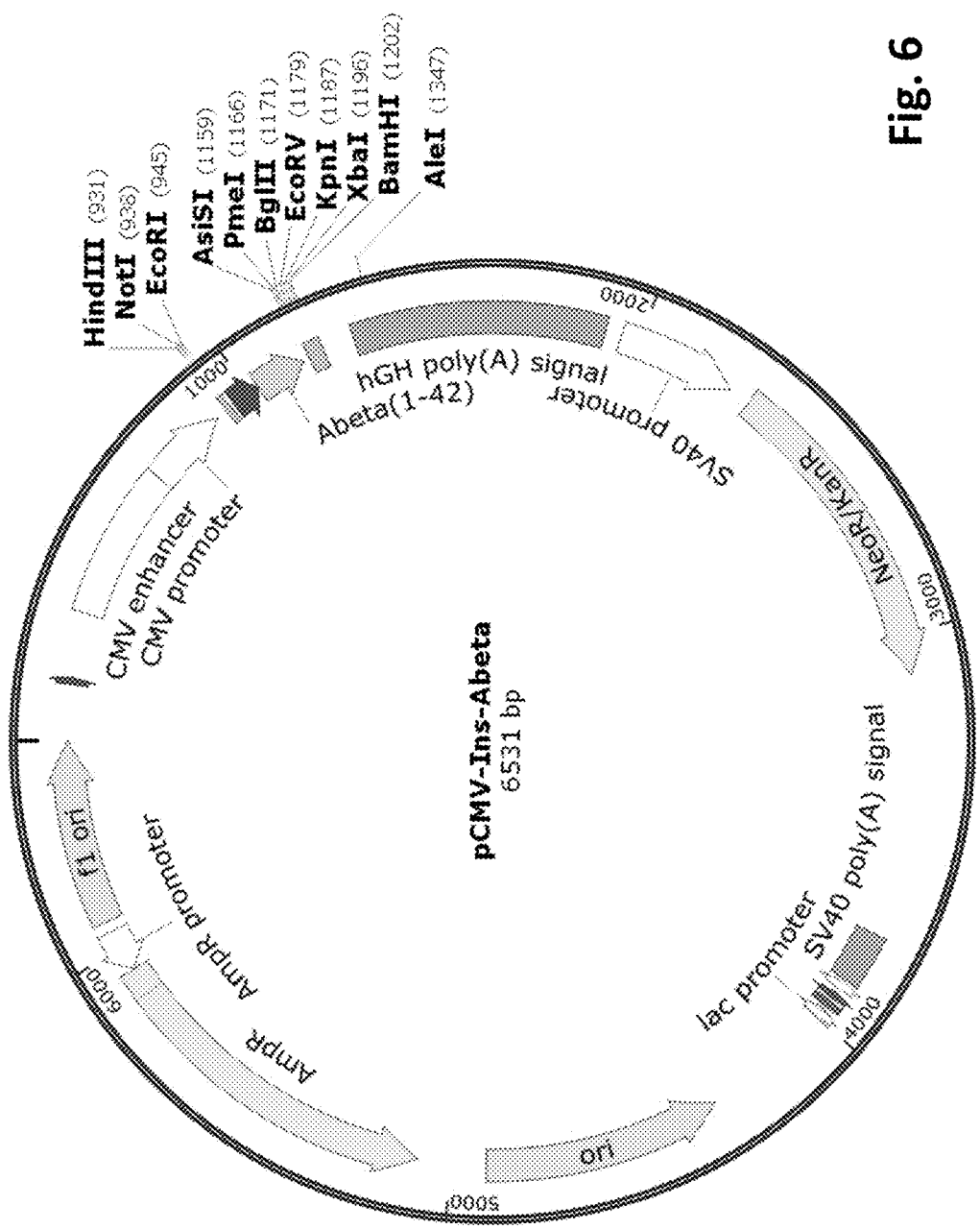
FIG. 6 depicts the map of the "pCMV-Ins-Abeta" expression vector.

The human Aβ sequence fused to different signal peptide sequence was PCR amplified and cloned in the p3XFLAG-CMV-13 vector. The p3XFLAG-CMV-13 expression vector is a 6.3 kb plasmid for transient expression of fusion proteins in mammalian cells. The prepro-trypsin leader signal sequence, which is an integral part of the vector, was deleted by quick change mutagenesis. Deletion of this prepro-trypsin sequence from the 5' of the multiple cloning site enabled use of this vector for cloning of Aβ fused to various signal sequences at the N-terminal of the peptide. The vector encodes three adjacent FLAG epitopes downstream of the multiple cloning region. Aβ sequence with a stop codon at the C-terminal end was inserted using the EcoR1 and BglII restriction sites so that the Flag tags are not fused to Aβ. The human cytomegalovirus (CMV) promoter-regulatory region upstream of the transgene drives transcription of the Aβ construct (FIG. 6). The vector also enabled selection of stable transfectants by virtue of the aminoglycoside phosphotransferase II gene (Neo), which confers resistance to aminoglycosides such as G418. It is a shuttle vector for mammalian cells and *E. coli*, in which the plasmid can be maintained and amplified because of the ampicillin resistant gene (AmpR) in the vector backbone.

The constructs were transiently transfected in 293T cells using FUGENE® 6 transfection reagent following the manufacture's instruction. 293T cells were routinely propagated in adhesion culture in DMEM medium (Invitrogen) supplemented with 10% FBS and incubated at 37° C. with 5% $CO_2$. For transfection of the expression vector, cells were plated to approximately 90% confluency (approximately $1.2 \times 10^5$ cells/ml) in each well of a 6-well tissue culture plate. Before transfection, the spent medium was replaced by 1 ml of serum free or low serum medium (DMEM without FBS or DMEM+1% FBS). For each transfection of cells in a single well of a 6-well plate, 1 μg of the expression construct was used. Upon transfection cells are incubated for up to 96 hours at 37° C. with 5% $CO_2$.

Figures 7A, 7B:
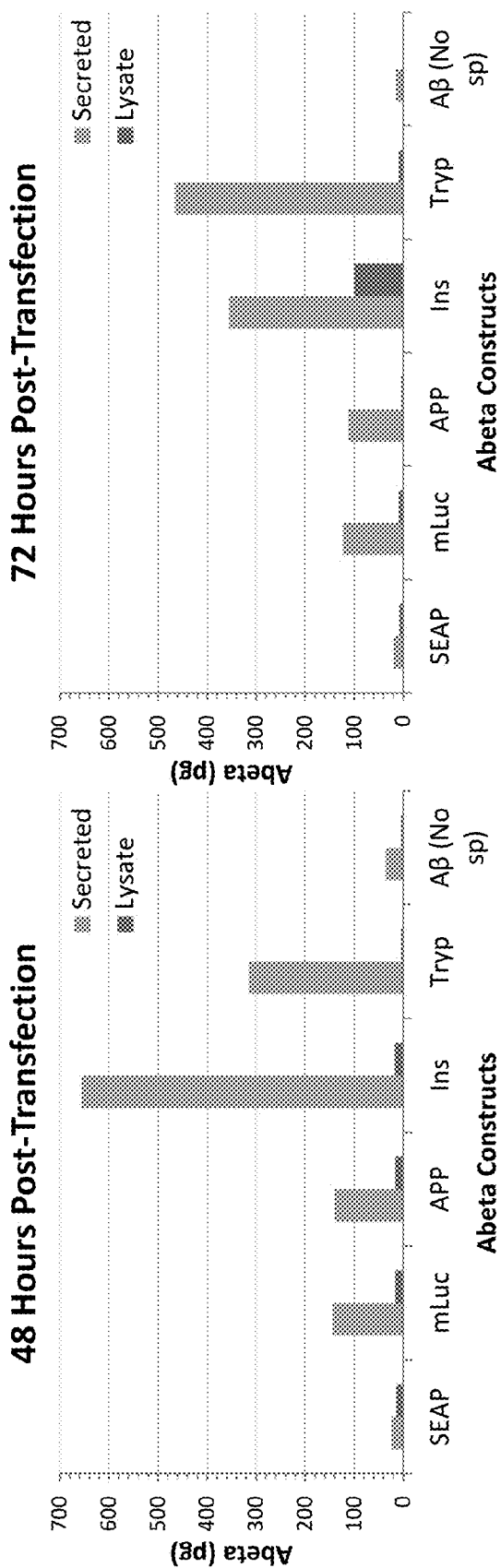
FIG. 7A-7B are graphs depicting the amount of human Aβ42 present in the cell lysate and supernatant of 293T cells 48 hours (FIG. 7A) and 72 hours (FIG. 7B) after transfection with mammalian expression constructs containing the signal sequences of human insulin (Ins), human trypsin (Tryp), human amyloid precursor protein (APP), human placental secreted alkaline phosphatase (SEAP), or *Metridia* luciferase (mLuc) of the marine copepod *Metridia longa* fused to Aβ42.

Supernatants were harvested 48 and 72 hours post transfection and cells were lysed in RIPA buffer (25 mM HEPES, pH 7.5, 150 mM NaCl, 0.25% Deoxycholate, 10% Glycerol, 25 mM NaF, 10 mM $MgCl_2$, 1 mM EDTA, 1% TRITON™ X-100, 0.5 mM PMSF, protease inhibitor cocktail). A solid-phase sandwich enzyme-linked immuno-sorbent assay (ELISA) was used to detect and quantify recombinant Aβ from the supernatant and soluble fractions of the cell lysates using ELISA Kit specific for the detection of human Aβ42 (Life Technologies, Catalogue no. KHB3441). Two of the signal peptides (Ins and Tryp) were efficient in secreting pathobiologically relevant Aβ concentration in the supernatant of 293T cells (FIGS. 7A-7B).

Figure 8:
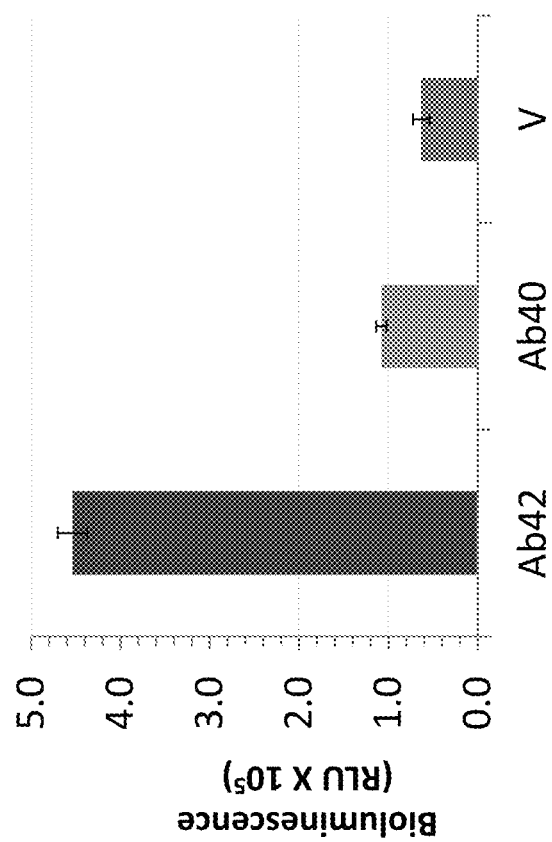
FIG. 8 is a graph depicting the presence of adenylate kinase (an indicator of cell damage/death) in the supernatant of transfected 293T cells 48 hours following transfection with constructs expressing Aβ42 or Aβ40 fused to the insulin signal peptide or a vector control without an inserted transgene.

Cytotoxicity of the transfected cells was measured by TOXILIGHT™ BioAssay Kit (Lonza) following the manufacturer's instruction. TOXILIGHT™ assay is a bioluminescent, non-destructive cytotoxicity assay designed to measure the release of adenylate kinase from damaged or dying cells. Adenylate kinase is ubiquitous in all eukaryotic cells. It is released into the culture medium when cells are damaged or when cells die. The enzyme actively phosphorylates ADP to form ATP and the resultant ATP is measured using the bioluminescent firefly luciferase reaction. The amount of adenylate kinase in the supernatant is quantitatively proportional to cytolysis and is measured by the intensity of the emitted light by the TOXILIGHT™ reagent. Constructs harboring either Aβ42 or Aβ40 fused to the insulin signal peptide or a vector control without any inserted transgene were used for transfecting the cells. Supernatant from the transfected cells was harvested 48, 72, or 96 hours post-transfection to measure Aβ-mediated cytotoxicity. The construct encoding the insulin signal peptide fused to Aβ42 elicited particularly strong cytotoxicity (FIG. 8).

Example 3: Amyloid Beta Expression in Rat Embryonic Cortical Neurons

Figure 9:
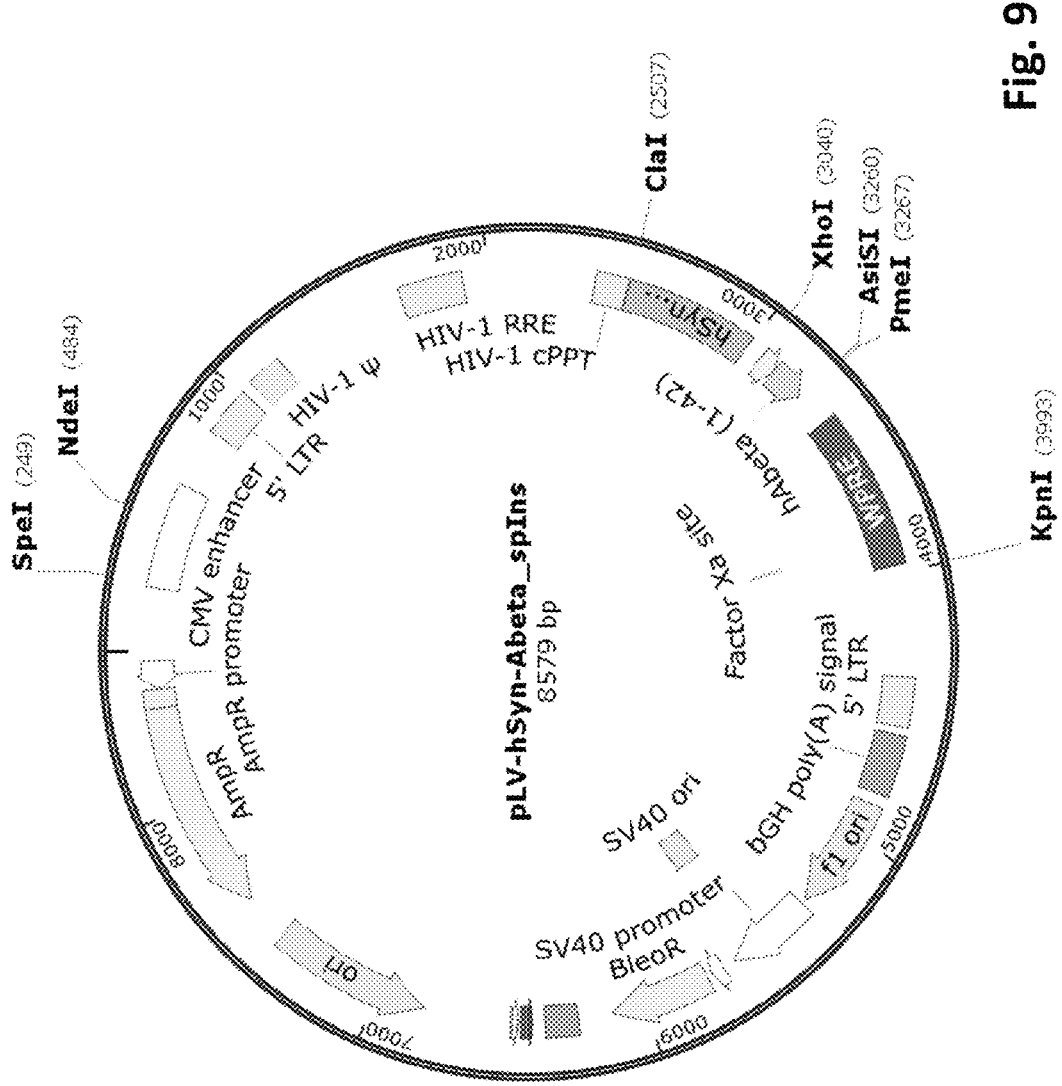
FIG. 9 depicts the map of the "pLV-hSyn-Abeta_spIns" expression vector.

Rat embryonic cortical neurons were used for expressing Aβ. For generating lentiviral constructs, an expression vector was used with the human synapsin 1 promoter upstream of the inserted insulin signal peptide-Aβ fusion polypeptide transgene (FIG. 9). The encoded fusion polypeptide is processed in the secretory pathway of the neuron, releasing Aβ in the extracellular milieu.

The pLV-Aβ constructs along with the psPAX2 packaging vector and pMD2.G envelope vector were transfected in 293T cells using LIPOFECTAMINE® 2000 (Invitrogen) transfection reagent following the manufacture's instruction to generate lentivirus containing the Aβ transgene. The virus was purified using LENTI-X™ Maxi Purification Kit (Clontech) from the supernatant of the transfected 293T cells according to the protocol provided by the manufacturer. Viral titer were determined by using Lentivirus-Associated p24 ELISA Kit (Cell BioLabs).

Figure 10B:
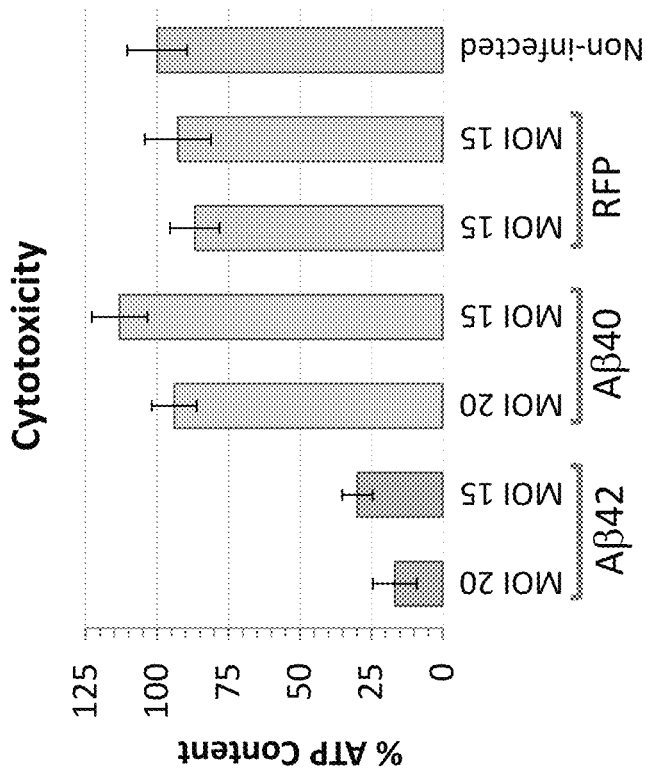
FIG. 10B is a graph depicting the cytotoxicity of rat embryonic cortical neurons, as determined by measuring ATP levels, after infection with lentiviral constructs expressing human Aβ42 or Aβ40.
Figure 10A:
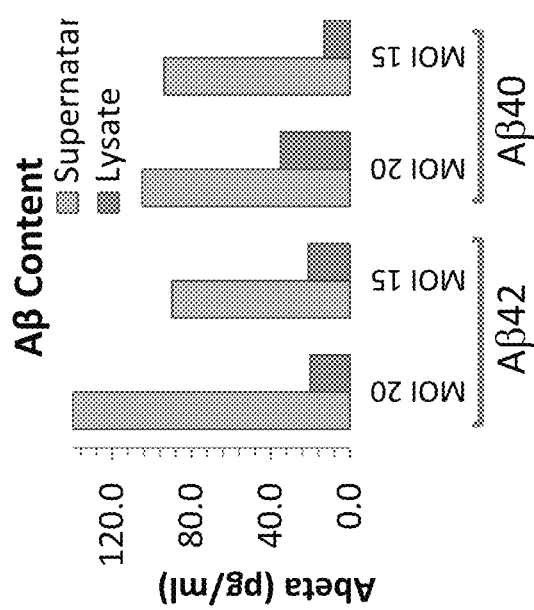
FIG. 10A is a graph depicting the amount of human Aβ42 or Aβ40 present in the cell lysate and supernatant of rat embryonic cortical neurons after infection with lentiviral constructs expressing human Aβ42 or Aβ40.

Rat embryonic cortices were dissected out of embryonic (E18) rat brains, and neurons were enriched in adherent monolayer culture. These cortical neurons were infected with lentiviral preparation harboring an Aβ transgene or a control gene (RFP in the same vector backbone). Infected cultures were harvested to quantify the amount of Aβ in the supernatant and cell lysate by Aβ-specific ELISA 21 days after infection (FIG. 10A). Corresponding cytotoxicity of the infected neurons was measured by quantifying ATP levels using VIALIGHT™ assay for cell viability (Lonza). Expression of human Aβ in the secretory pathway of rat embryonic cortical neurons caused profound cytotoxicity (FIG. 10B).

When rat embryonic cortical neurons were infected with lentiviral constructs (as depicted in FIG. 9) expressing wild-type human Aβ42 or various mutations (i.e., F20E, Arctic (E22G), I31E, and E22G/I31E) in the secretory pathway of these cells, differential toxicity was observed, reminiscent of the differential cytotoxic effects caused by these mutations in yeast (see Example 1). The Arctic mutation (E22G) of human Aβ42 had a more toxic effect compared to the wild-type human Aβ42. Three mutations—F20E, I31E, and E22G/I31E—exerted less cytotoxic effects compared to either the wild-type human Aβ42 or the Arctic variation of human Aβ42.

Example 4: Amyloid Beta-Induced Cytotoxicity in Neuronal Cultures

Figure 11A:
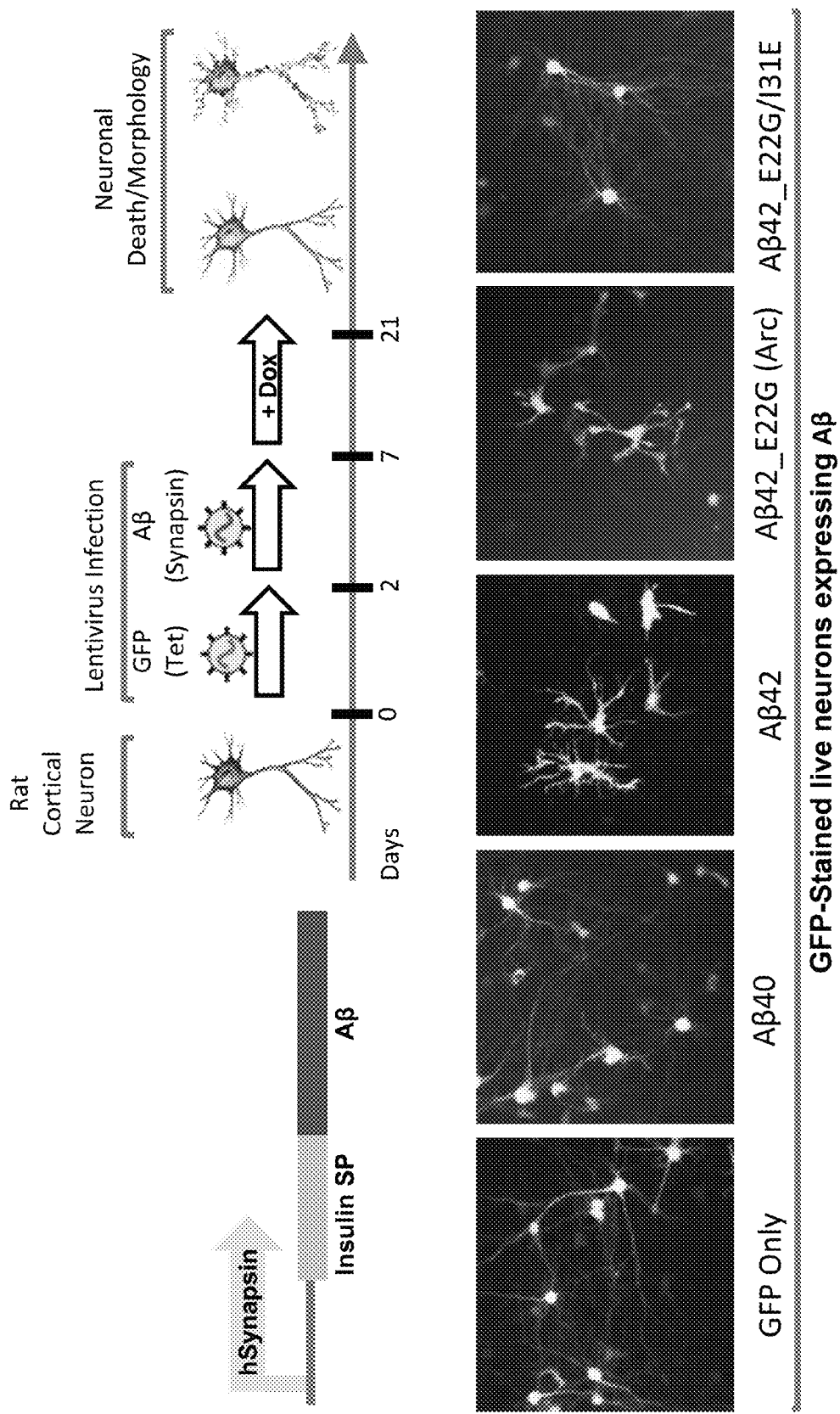
FIG. 11A is a series of images of live rat cortical neurons infected with a GFP expression construct and the indicated lentiviral Aβ construct. Cells infected with only the GFP expression construct served as a control ("GFP only"). The top panel depicts a schematic of the expression constructs and the experimental protocol.

Rat cortical neurons were infected with a doxycycline-inducible lentiviral GFP construct. Two days post-infection, the cells were infected again with neuron-specific (synapsin promoter) lentiviral Aβ constructs (i.e., Aβ40, Aβ42, and various mutations). The doubly-infected cells were treated with doxycycline 7 days post-infection to express GFP. After 21 days of the initial infection, live neurons were visualized using fluorescence microscopy to observe the effect of different Aβ variants on neuronal survival and morphology by visualizing neurons expressing GFP in presence of Aβ expressed from the transgenes. Wild-type human Aβ42 and the Aβ42_Arctic (E22G) mutation caused neuronal death and adversely affected neurite outgrowth and structures, which were detected by microscopic observation of GFP-stained live neurons (FIG. 11A). Both the Aβ42_I31E and the Aβ42_Arc/I31E mutations demonstrated reduced cytotoxicity and no significant morphological distortions of the neurons and neurites in rat cortical neurons infected at multiplicity of infection (MOI) identical to the wild-type Aβ42 and Aβ42_Arctic (E22G) viral constructs.

Figure 11B:
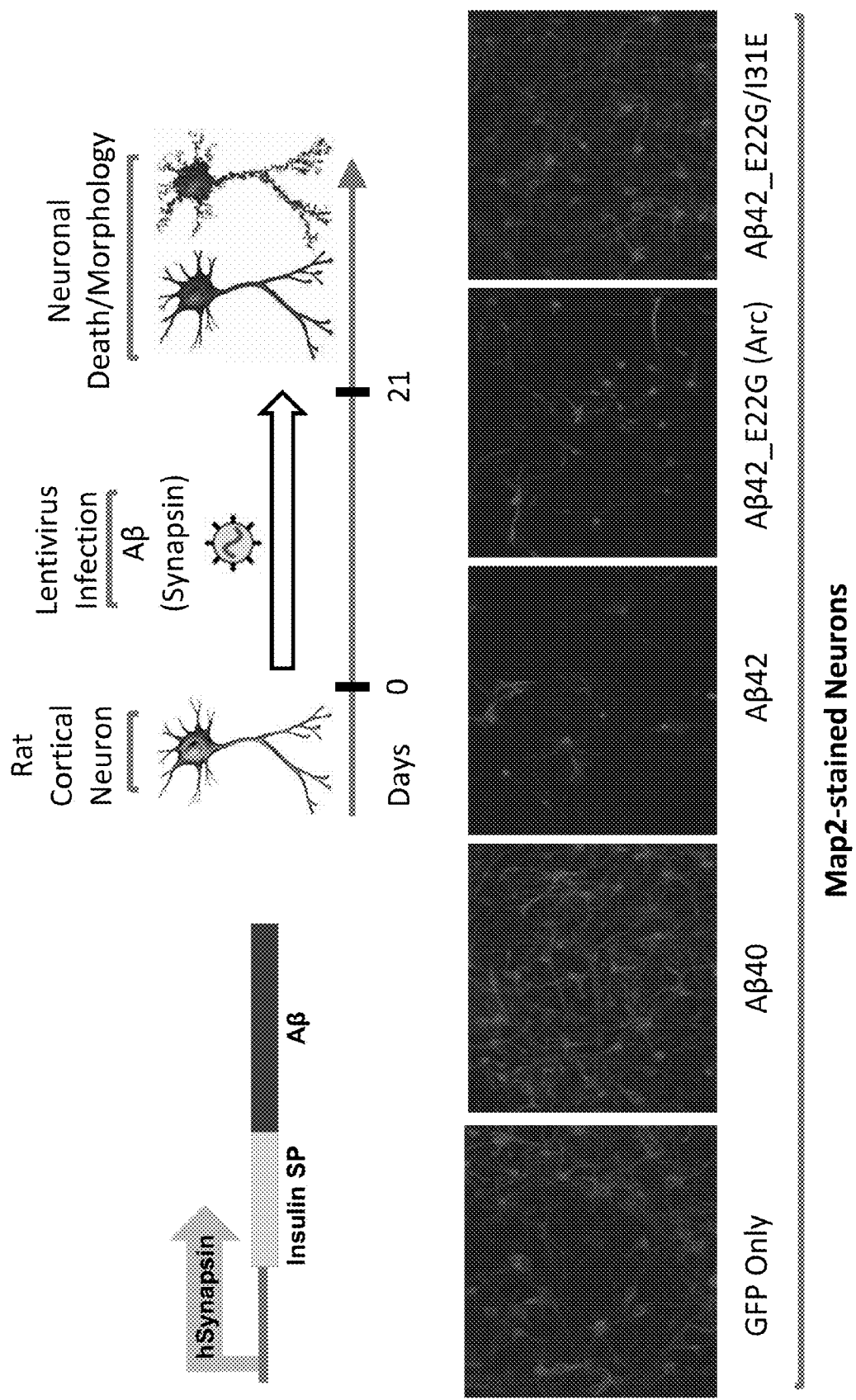
FIG. 11B is a series of images depicting Map2-stained rat cortical neurons infected with the indicated lentiviral Aβ construct or with GFP ("GFP only"). The top panel depicts a schematic of the expression constructs and the experimental protocol.

Similar observations were also made by immunohistochemical analysis of rat cortical neurons infected with neuron-specific (synapsin promoter) lentiviral Aβ constructs. Twenty-one days post-infection, the neurons were stained with a neuron-specific microtubule-associated protein 2 (Map2) primary antibody (rabbit polyclonal, Millipore) and ALEXA FLUOR® (red fluorophore conjugated) secondary antibody (goat anti-rabbit polyclonal, Life Technologies). Neuronal cells and morphology were visualized to observe the effect of different Aβ mutations using fluorescence microscopy. Similar to the results obtained from live neurons described above, wild-type Aβ42 and the Aβ42_Arctic (E22G) mutation caused profound cytotoxicity, resulting in massive neuronal loss and distorted neurite structures and outgrowth (FIG. 11B). Also similar to the observations with live neuronal imaging, the Aβ42_I31E and Aβ42_Arc/I31E mutations demonstrated reduced cytotoxicity and had no significant effects on the neuronal morphology (FIG. 11B).

Example 5: Poly-Aβ Expression in Mammalian Cells

Figure 12:
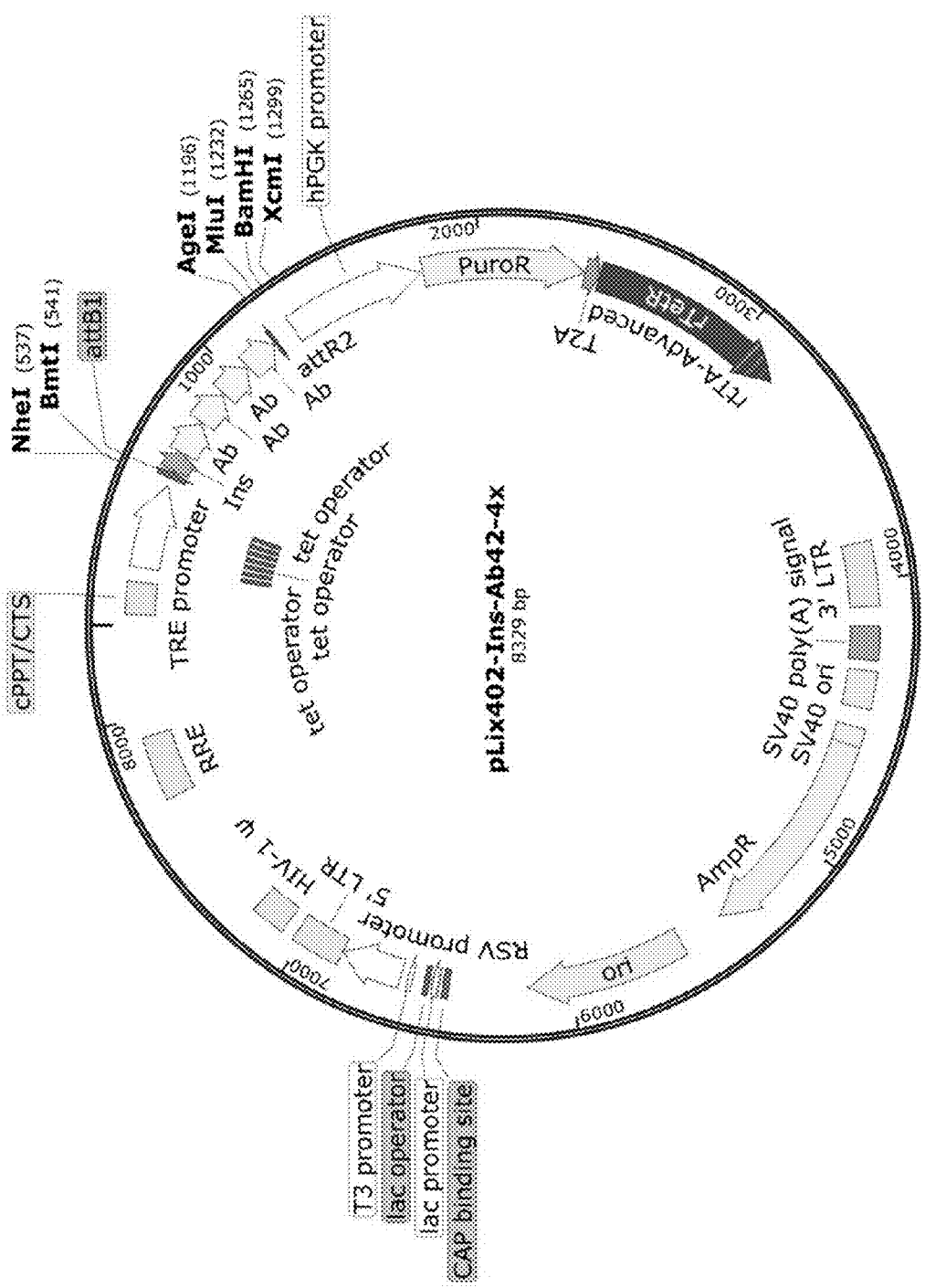
FIG. 12 depicts the map of the poly-Aβ42 "pLIX402-Ins-Aβ42-4X" expression vector, which contains four copies of Aβ42 linked by 2 amino acid linkers. The poly-Aβ is linked at the N-terminus to the insulin signal peptide. Expression of the transgene is driven by a tetracycline (doxycycline)-inducible promoter. Similar expression vectors were generated for Aβ40-4X, Aβ40-6X, Aβ40-8X, Aβ42_Arctic-4X (also referred to as "4X_Arc"), Aβ42-6X, and Aβ42-8X.

Similar to the poly-Aβ (Aβ40 or Aβ42_1X/4X/6X/8X) expression constructs in yeast (see Example 1), a poly-Aβ toxicity model was developed in mammalian cells. Stable cell lines with chromosomally-integrated tetracycline (doxycycline)-inducible poly-A13 transgenes (Aβ42-4X, Aβ42-6X, Aβ40-4X, Aβ40-6X and Aβ42-Arctic-4X) linked to an N-terminal insulin signal peptide were generated (FIGS. 13A-13B). These expression constructs were generated using the pLix402 lentiviral plasmid (FIG. 12). The poly-Aβ constructs were individually transfected into 293T cells along with the lentiviral packaging plasmid psPAX and the viral envelope-expressing plasmid mMD2.G using LIPO-FECTAMINE® 2000 (Invitrogen) transfection reagent to generate lentivirus containing the poly-Aβ transgene. The virus was harvested from the supernatant of transfected 293T cells 2 and 3 days post-transfection and subsequently purified and concentrated using the LENTI-X™ Maxi Purification kit (Clontech) according to the manufacturer's instructions.

To generate stable cells harboring the expression transgene for the poly-Aβ constructs, 293T cells were infected using POLYBRENE® infection reagent (Sigma Aldrich), which is used to introduce retroviral vectors into mammalian cells. Infected cells were then selected using puromycin (2-10 µg/ml). Infected cells harboring the transgene survive this selection pressure whereas the control cells without the transgene die in 2-3 days. Aliquots of the selected cells were frozen in liquid nitrogen or maintained and propagated for further applications.

Expression of Aβ peptide from these stable cell lines was measured in the culture supernatant 72-96 hours following doxycycline induction (FIG. 13D). Toxicity was measured 72-96 hours following doxycycline induction using a TOX-ILIGHT™ cytotoxicity assay (Lonza) as described in Example 2. These stable lines demonstrated an Aβ peptide-mediated cytotoxic effect (Aβ42-6X≥Aβ42-Arctic-4X≥Aβ42-4X≥AB40-6X≥Aβ40-4X), as determined by adenylate kinase release in the cell culture supernatant from damaged cells upon doxycycline-induction of the transgenes (FIG. 13C).

Example 6: Poly-Aβ Expression in Neuronal Cells

Rat embryonic cortical neurons were infected with lentiviral poly-Aβ expression constructs to model poly-Aβ toxicity. Tetracycline (doxycycline)-inducible poly-Aβ (Aβ42-4X, Aβ42-6X, Aβ40-4X, Aβ40-6X, and Aβ42-Arctic-4X) viral constructs described in Example 5 were used to express poly-Aβ constructs in rat cortical neurons. In each expression construct, the poly-Aβ coding sequence is linked to an N-terminal insulin signal peptide. The poly-Aβ expression plasmids were packaged in lentiviral particles, which were generated by 293T cells as described in Example 3.

Figure 14:
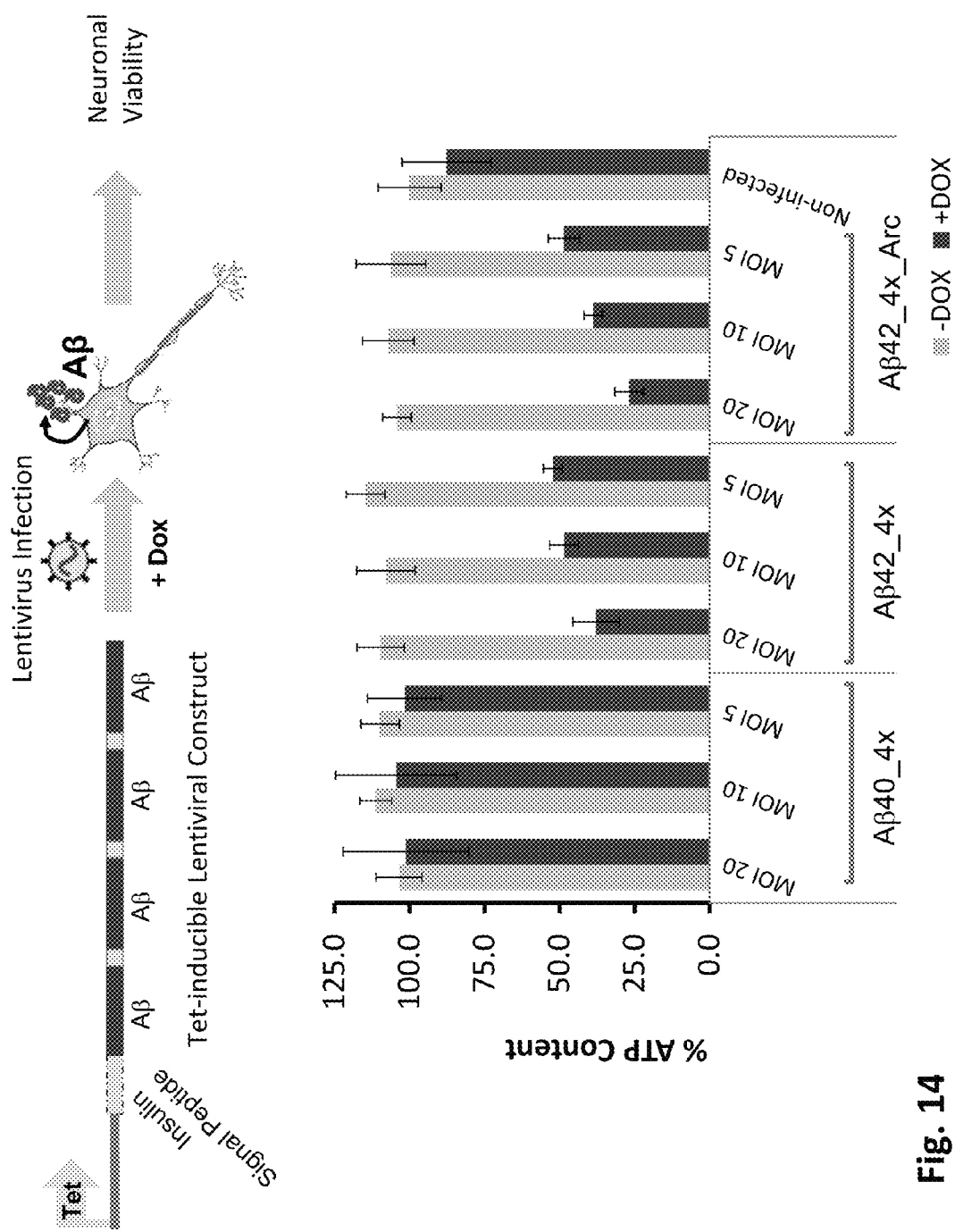
FIG. 14 shows that poly-Aβ expression is toxic in rat cortical neurons. The top panel shows a schematic of the experimental protocol. The bottom panel is a graph depicting the cytotoxicity of rat embryonic cortical neurons, as determined by measuring ATP levels, following infection with lentiviral constructs expressing the indicated poly-A1342 or poly-Aβ40 expression construct.

Rat cortical neurons were enriched from cortices dissected out of embryonic (E18) rat brains and enriched in adherent monolayer culture as described in Example 3. Purified lentiviral preparations at different MOI were used to infect these cortical neurons to express poly-Aβ transgenes. Three days post-infection, expression of poly-Aβ was induced by adding doxycycline (2 µg/ml) to the infected cultures. The viability of the infected neurons was measured three weeks post doxycycline-induction by quantifying ATP levels using VIALIGHT™ assay for cell viability (Lonza) to determine the cytotoxicity of the poly-Aβ expression constructs. Expression of human Aβ42-4X-WT or Aβ42-4X-Arctic in the secretory pathway of rat embryonic cortical neurons caused profound cytotoxicity compared to Aβ40-4X (FIG. 14).

Example 7: Rescue of Aβ-Toxicity by Small Molecule Compounds in Mammalian Cells

Figure 15:
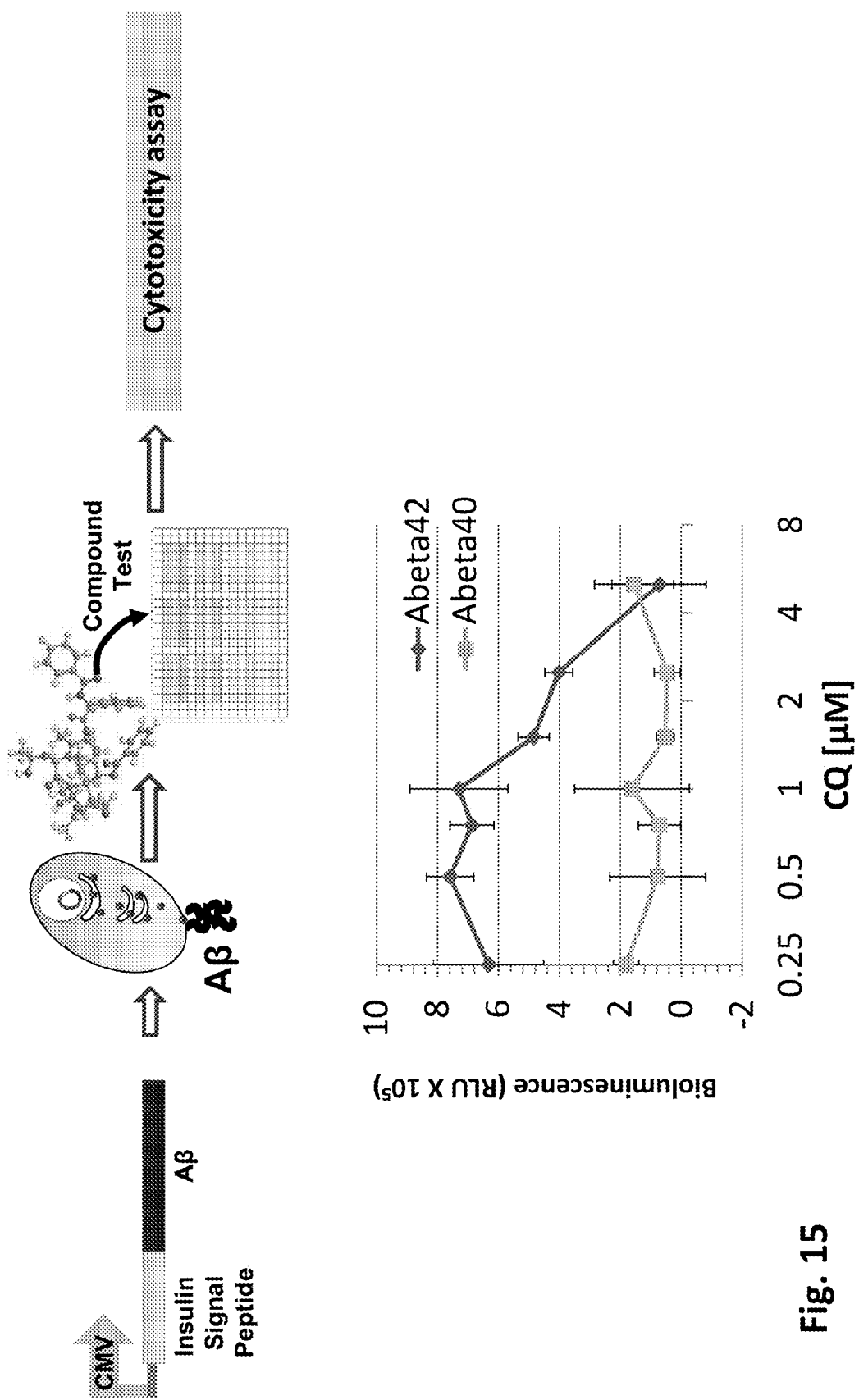
FIG. 15 is a graph depicting the effect of clioquinol on Aβ-mediated cytotoxicity as determined by measuring adenylate kinase released from the damaged cells.

The cytotoxic model in 293T cells was used to test the effect of small molecule compounds to alleviate Aβ-mediated toxicity. The Aβ42 or Aβ40 expression construct was transiently transfected and small molecules were added in different dosages 12 hours post-transfection. Cytotoxicity was measured at different compound dosages by adenylate kinase released from the damaged cells by TOXILIGHT™ BioAssay Kit (Lonza) 96 hours post-transfection. One example of a compound-mediated effect of toxicity alleviation was by clioquinol (CQ), which rescued Aβ-mediated toxicity between concentrations of 2 and 5 µM (FIG. 15). Similar assays are also performed using virally-infected stable 293T cells harboring tetracycline (doxycycline)-inducible poly-Aβ expression constructs to identify compounds that rescue cytotoxicity caused by poly-Aβ expression constructs.

Example 8: An Aβ43 Expression Construct is Toxic to Yeast Cells

Figure 16A:
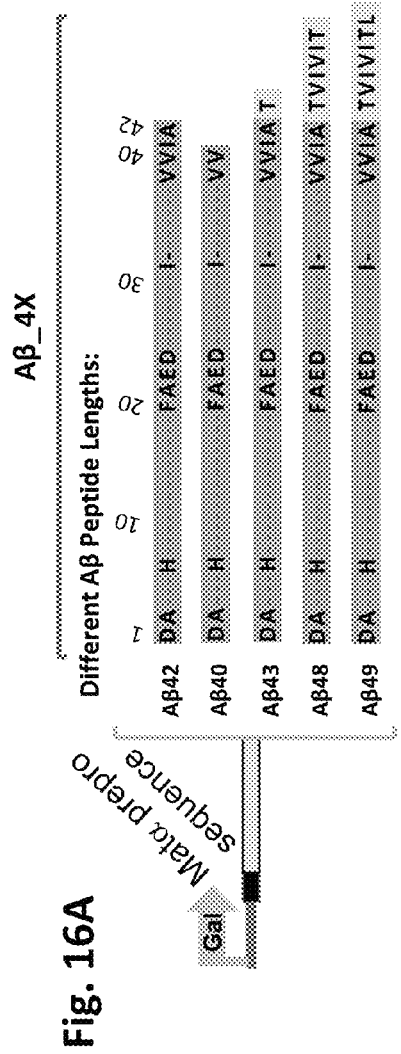
FIG. 16A depicts yeast poly-Aβ-4X (4 tandem Aβ peptides) expression constructs (various residues of amyloid beta peptides including SEQ ID NOS 1, 104, and 105).

Aβ43 was expressed in the yeast *S. cerevisiae* as a tandem polypeptide (four tandem Aβ peptides linked by 6-8 amino acid linkers) using a poly-Aβ expression construct under the control of the galactose-inducible GAL1 promoter. The Aβ polypeptide coding sequence is linked at the N-terminus to the mating factor α pre-pro signal sequence for directed expression of the transgene in the secretory pathway (FIG. 16A).

The yeast expression construct containing four copies (4X) of Aβ43 had the following nucleotide and amino acid sequences.

Matα-Aβ43_4X Nucleotide Sequence
(SEQ ID NO: 100)
GTCGACTGGATCCACAAGTTTGTACAAAAAAGCAGGCTGGTACCAAAAGA

ATGAGATTCCCATCTATTTTCACCGCTGTTTTGTTTGCTGCTTCTTCTGC

TTTGGCTGCTCCAGTTAACACTACTACTGAAGATGAAACTGCTCAAATTC

CAGCTGAAGCTGTTATTGGTTACTTGGATTTGGAAGGTGATTTCGATGTT

GCTGTTTTGCCATTCTCTAACTCTACCAACAATGGTTTGTTGTTCATCAA

CACCACCATTGCTTCTATTGCTGCTAAAGAAGAAGGTGTCTCTTTGGATA

AGAGAGAAGCTGAAGCAGACGCAGAATTCAGACATGATTCTGGTTATGAA

GTTCACCACCAAAAGTTGGTTTTCTTCGCTGAAGATGTTGGTTCTAACAA

GGGTGCTATTATCGGTTTGATGGTTGGTGGTGTAGTTATTGCTACAAAAA

GAGAAGCCGAAGCTGAAGCTGATGCCGAATTCAGACACGATAGTGGTTAC

GAAGTACATCATCAAAAATTAGTCTTTTTTGCCGAAGATGTCGGTAGTAA

CAAAGGTGCAATCATTGGTTTAATGGTCGGTGGTGTCGTAATAGCAACTA

AGAGAGAAGCAGACGCCGAAGCCGATGCAGAATTCAGACACGACTCCGGT

TACGAAGTCCATCACCAAAAGTTGGTATTCTTTGCCGAAGATGTCGGTTC

AAACAAGGGTGCCATAATAGGTTTAATGGTTGGTGGTGTCGTTATCGCTA

CCAAGAGAGAAGCTGACGCTGAAGCAGACGCCGAATTCAGACACGACTCA

GGTTATGAAGTACACCATCAAAAATTGGTATTTTTCGCAGAAGATGTTGG

TTCCAACAAAGGTGCCATTATTGGTTTGATGGTTGGTGGTGTCGTCATAG

CTACTTAAACCCAGCTTTCTTGTACAAAGTGGTGCGGCCGCACTCGAG

Matα-Aβ43_4X Amino Acid Sequence
(SEQ ID NO: 101)
MRFPSIFTAVLFAASSALAAPVNTTTEDETAQIPAEAVIGYLDLEGDFDV

AVLPFSNSTNNGLLFINTTIASIAAKEEGVSLDKREAEADAEFRHDSGYE

-continued

VHHQKLVFFAEDVGSNKGAIIGLMVGGVVIATKREAEAEADAEFRHDSGY

EVHHQKLVFFAEDVGSNKGAIIGLMVGGVVIATKREADAEADAEFRHDSG

YEVHHQKLVFFAEDVGSNKGAIIGLMVGGVVIATKREADAEADAEFRHDS

GYEVHHQKLVFFAEDVGSNKGAIIGLMVGGVVIAT

Figure 16B:
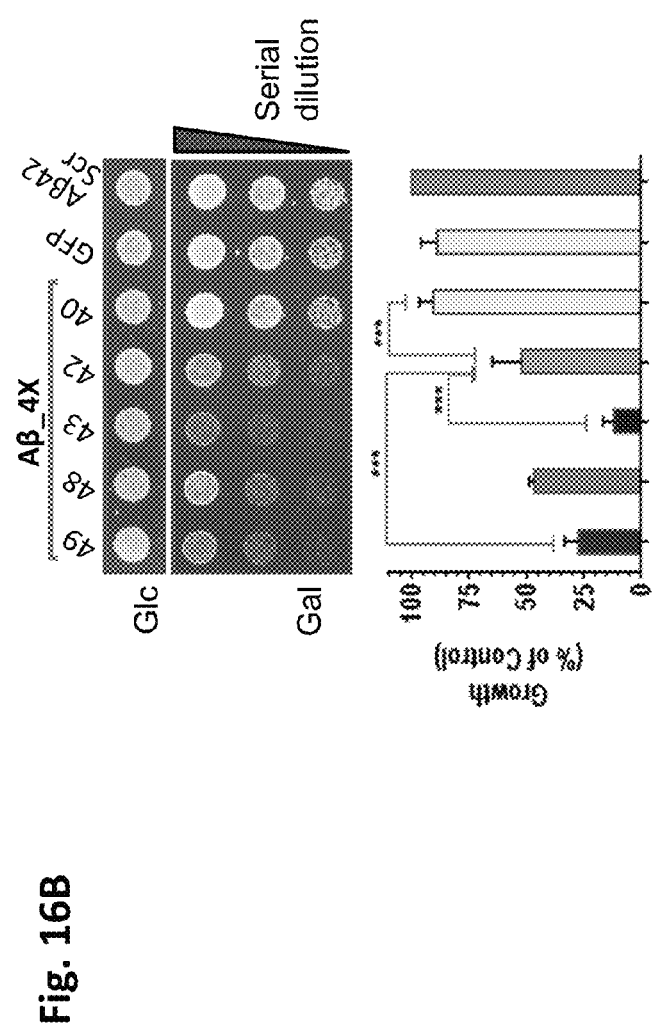
FIG. 16B is a series of photographs depicting yeast toxicity resulting from expression of the indicated poly-Aβ-4X expression construct and a graph depicting the quantification of the growth. Glc, glucose; Gal, galactose. *** indicates P-value≤0.001.

The toxicity of Aβ43 to yeast cells was compared to that of similar poly-Aβ expression constructs expressing Aβ42, Aβ40, Aβ48, or Aβ49. The Aβ_scrambled construct, in which the amino acid sequence of Aβ42 was randomly scrambled, served as a control tandem peptide, and a GFP construct served as a vector control. The transgenes were expressed from an episomal expression plasmid (2-micron) under the selection of leucine auxotrophy. The growth of the transformed yeast was measured on synthetic agar media lacking leucine and containing galactose for induction of the transgene. The transformed strains were also grown on similar media with glucose as a measure of growth without the induction of transgene expression. An ImageJ spot assay quantification macro was used to quantify yeast growth on solid media. Aβ43 was significantly more cytotoxic than other Aβ peptides when expressed in yeast (FIG. 16B). The relative toxicity was Aβ43>Aβ49≥Aβ48≥Aβ42>Aβ40.

Example 9: An Aβ43 Expression Construct is Toxic to Mammalian Cells

To express Aβ43 peptide in mammalian cells, an expression construct was generated by fusing the insulin signal peptide to the N-terminus of the Aβ43 peptide coding sequence (FIGS. 17A and 17B).

The mammalian expression construct encoding Aβ43 had the following nucleotide and amino acid sequences.

Ins-Aβ43_1X Nucleotide Sequence
(SEQ ID NO: 102)
CACCATGGCCCTGTGGATGCGCCTCCTGCCCCTGCTGGCGCTGCTGGCCC

TCTGGGGACCTGACCCAGCCGCAGCCGATGCGGAATTTCGCCATGATTCT

GGCTATGAAGTGCATCATCAGAAACTGGTGTTTTTTGCGGAAGATGTGGG

CTCTAACAAAGGCGCGATTATTGGCCTGATGGTGGGCGGCGTGGTGATTG

CGACATAA

Ins-Aβ43_1X Amino Acid Sequence
(SEQ ID NO: 103)
MALWMRLLPLLALLALWGPDPAAADAEFRHDSGYEVHHQKLVFFAEDVG

SNKGAIIGLMVGGVVIAT

The expression construct is expressed under the CMV promoter using pCMV vector as described above (see Example 2 and FIG. 6). The cytotoxic effect of Aβ43 in mammalian cells was tested in 293T cells by transiently transfecting the expression construct and measuring adenylate kinase released from the damaged cells 96 hours post-transfection. Cytotoxicity was measured using the TOXILIGHT™ BioAssay Kit (Lonza) following the manufacturer's instructions (see Example 2). Similar to the results from yeast cells described in Example 8, Aβ43 was significantly more cytotoxic compared to Aβ42, Aβ48, Aβ49, or Aβ40 (FIG. 17C).

Other Embodiments

It is to be understood that, while the invention has been described in conjunction with the detailed description thereof, the foregoing description is intended to illustrate and not limit the scope of the invention. It is also to be understood that claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all embodiments in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise and such embodiments do not constitute added matter or extend beyond the content of the application as filed. Where elements are presented as lists, it is to be understood that each subgroup of the elements is also disclosed, and any one or more element(s) can be removed from the group, and such subgroup or resulting list is explicitly disclosed herein and does not constitute added matter or extend beyond the content of the application as filed. It should be understood that, in general, where the invention, or aspects of the invention, is/are referred to as comprising particular elements, features, etc., certain embodiments of the invention or aspects of the invention consist, or consist essentially of, such elements, features, etc. It should also be understood that any embodiment of the invention, can be explicitly excluded from the claims without constituting added matter or extending beyond the content of the application as filed. Other aspects, advantages, and modifications of the invention are within the scope of the claims set forth below.

What is claimed is:

1. An expression construct comprising a promoter operably linked to a nucleic acid encoding a polypeptide comprising a signal sequence, a Golgi-directing pro sequence, and a human amyloid beta protein.

2. An expression construct comprising a promoter operably linked to a nucleic acid encoding a polypeptide comprising a signal sequence, a Golgi-directing pro sequence, and a polypeptide having the formula $[X-Y]_n$, wherein each X is, independently, absent or is a linker; each Y is, independently, a human amyloid beta peptide; and n is an integer between two and eight, inclusive.

3. The expression construct of claim 1, wherein the signal sequence is identical to the signal sequence of a naturally occurring yeast protein.

4. The expression construct of claim 3, wherein the signal sequence is the yeast mating factor alpha signal sequence.

5. The expression construct of claim 1, wherein the Golgi-directing pro sequence is the pro sequence of yeast mating factor alpha, KEX2, carboxypeptidase Y, Pep4, or Prb1.

6. The expression construct of claim 1, wherein the promoter is an inducible promoter.

7. The expression construct of claim 6, wherein the inducible promoter is GALL-10, GAL1, GALL, GALS, GPD, ADH, TEF, CYC1, MRP7, MET25, TET, VP16, or VP16-ER.

8. The expression construct of claim 1, wherein each human amyloid beta protein is independently selected from the group consisting of wild type Aβ38, wild type Aβ39, wild type Aβ40, wild type Aβ41, wild type Aβ42, wild type Aβ43, wild type Aβ48, and wild type Aβ49.

9. The expression construct of claim 1, wherein the polypeptide comprises a plurality of amyloid beta proteins.

10. The expression construct of claim 9, wherein the polypeptide comprises at least two amyloid beta proteins.

11. The expression of claim 9, wherein the polypeptide comprises at least four amyloid beta proteins.

12. The expression construct of claim 1, wherein the polypeptide comprises the amino acid sequence of SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, or SEQ ID NO:101.

13. The expression construct of claim 1, wherein the expression construct is an episomal plasmid or an integrative plasmid.

14. The expression construct of claim 13, wherein the integrative plasmid is pAG303, pAG304, pAG305, pAG306, pRS303, pRS304, pRS305, pRS306, or a derivative thereof.

15. A yeast cell comprising the expression construct of claim 1, wherein expression of the nucleic acid and production of the polypeptide in the cell results in a decrease in growth or viability of the cell or renders the cell non-viable.

16. The yeast cell of claim 15, wherein the expression construct is episomal or is integrated in the genome of the yeast cell.

17. The yeast cell of claim 15, wherein the yeast is *Saccharomyces cerevisiae, Saccharomyces uvae, Saccharomyces kluyveri, Schizosaccharomyces pombe, Kluyveromyces lactis, Hansenula polymorpha, Pichia pastoris, Pichia methanolica, Pichia kluyveri, Yarrowia lipolytica, Candida* sp., *Candida utilis, Candida cacaoi, Geotrichum* sp., or *Geotrichum fermentans.*

18. The yeast cell of claim 15, wherein at least one gene that encodes a protein involved in drug efflux or cell permeability is disrupted.

19. The yeast cell of claim 18, wherein the at least one gene is PDR1, PDR3, PDR5, SNQ2, or ERG6.

20. A method of inducing toxicity in a cell, the method comprising:
providing the cell of claim 15; and
inducing a level of expression of the nucleic acid in the cell that is toxic to the cell.

21. A method of identifying a compound that prevents or suppresses amyloid beta-induced toxicity, the method comprising:
culturing the cell of claim 15 in the presence of a candidate agent and under conditions that allow for expression of the nucleic acid at a level that, in the absence of the candidate agent, is sufficient to induce toxicity in the cell;
measuring cell growth or viability in the presence of the candidate agent; and
comparing cell growth or viability measured in the presence of the candidate agent to cell growth or viability in the absence of the candidate agent,
wherein if cell growth or viability is increased in the presence of the candidate agent as compared to in the absence of the candidate agent, then the candidate agent is identified as a compound that prevents or suppresses amyloid beta-induced toxicity.

22. A method of identifying a genetic suppressor or enhancer of amyloid beta-induced toxicity, the method comprising:
providing the cell of claim 15, wherein the cell has been genetically modified to overexpress a gene;
culturing the cell under conditions that allow for expression of the protein at a level that, in the absence of overexpression of the gene, is sufficient to induce toxicity in the cell;
measuring cell growth or viability in the presence of overexpression of the gene; and
comparing cell growth or viability measured in the presence of overexpression of the gene to cell growth or viability in the absence of overexpression of the gene,
wherein (i) if cell growth or viability is increased in the presence of overexpression of the gene as compared to in the absence of overexpression of the gene, then the gene is identified as a genetic suppressor of amyloid beta-induced toxicity, and (ii) if cell growth or viability is decreased in the presence of overexpression of the gene as compared to in the absence of overexpression of the gene, then the gene is identified as a genetic enhancer of amyloid beta-induced toxicity.

23. A method of identifying a genetic suppressor or enhancer of amyloid beta-induced toxicity, the method comprising:
providing the cell of claim 15, wherein an endogenous gene of the cell has been disrupted;
culturing the cell under conditions that allow for expression of the protein at a level that, in the absence of disruption of the endogenous gene, is sufficient to induce toxicity in the cell;
measuring cell growth or viability in the presence of disruption of the endogenous gene; and
comparing cell growth or viability measured in the presence of disruption of the endogenous gene to cell growth or viability in the absence of disruption of the endogenous gene,
wherein (i) if cell growth or viability is increased in the presence of disruption of the endogenous gene as compared to in the absence of disruption of the endogenous gene, then the gene is identified as a genetic enhancer of amyloid beta-induced toxicity, and (ii) if cell growth or viability is decreased in the presence of disruption of the endogenous gene as compared to in the absence of disruption of the endogenous gene, then the gene is identified as a genetic suppressor of amyloid beta-induced toxicity.

24. The expression construct of claim 3, wherein the signal sequence is the signal sequence of yeast killer toxin K1, secreted acid phosphatase, invertase (sucrase), or Pst1.

25. The expression construct of claim 1 wherein each human amyloid beta protein is independently selected from the group consisting of Aβ38, Aβ39, Aβ40, Aβ41, Aβ42, Aβ43, Aβ48, and Aβ49 and comprises a mutation selected from the group consisting of A2T, A2V, H6R, D7N, E11K, F20E, A21G, E22G, E22Q, E22K, E22 deletion, D23N, I31E, E22G/I31E, A42T, and A42V.

26. An expression construct comprising a promoter operably linked to a nucleic acid encoding a polypeptide comprising a signal sequence and a human amyloid beta protein, wherein the signal sequence is an insulin signal sequence or a trypsin signal sequence.

27. An expression construct comprising a promoter operably linked to a nucleic acid encoding a polypeptide comprising a signal sequence and a polypeptide having the formula $[X-Y]_n$, wherein each X is, independently, absent or is a linker; each Y is, independently, a human amyloid beta peptide; and n is an integer between two and eight, inclusive, wherein the signal sequence is an insulin signal sequence or a trypsin signal sequence.

28. The expression construct of claim 26 wherein each human amyloid beta protein is independently selected from the group consisting of wild type Aβ38, wild type Aβ39, wild type Aβ40, wild type Aβ41, wild type Aβ42, wild type Aβ43, wild type Aβ48, and wild type Aβ49.

29. The expression construct of claim 26 wherein each human amyloid beta protein is independently selected from the group consisting of Aβ38, Aβ39, Aβ40, Aβ41, Aβ42, Aβ43, Aβ48, and Aβ49 and comprises a mutation selected from the group consisting of A2T, A2V, H6R, D7N, E11K, F20E, A21G, E22G, E22Q, E22K, E22 deletion, D23N, I31E, E22G/I31E, A42T, and A42V.

30. The expression construct of claim 26, wherein the polypeptide comprises the amino acid sequence of SEQ ID NO:93, SEQ ID NO:95, or SEQ ID NO: 103.

31. The expression construct of claim 26 wherein the expression construct is a plasmid or viral vector.

32. The expression construct of claim 26 wherein the polypeptide comprises a plurality of amyloid beta proteins.

33. The expression construct of claim 32, wherein the polypeptide comprises at least two amyloid beta proteins.

34. The expression of claim 32 wherein the polypeptide comprises at least four amyloid beta proteins.

35. A mammalian cell comprising the expression construct of claim 26 wherein expression of the nucleic acid and production of the polypeptide in the cell results in a decrease in growth or viability of the cell or renders the cell nonviable.

36. The mammalian cell of claim 35 wherein the cell is a neuronal cell.

* * * * *

SEQUENCE LISTING

```
<160> NUMBER OF SEQ ID NOS: 105

<210> SEQ ID NO 1
<211> LENGTH: 43
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15
```

```
Leu Val Phe Phe Ala Glu Asp Val Gly Ser Asn Lys Gly Ala Ile Ile
            20                  25                  30

Gly Leu Met Val Gly Gly Val Val Ile Ala Thr
            35                  40
```

<210> SEQ ID NO 2
<211> LENGTH: 936
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
gtcgactgga tccacaagtt tgtacaaaaa agcaggctgg taccaaaaga atgagattcc      60
catctatttt caccgctgtt ttgtttgctg cttcttctgc tttggctgct ccagttaaca    120
ctactactga agatgaaact gctcaaattc cagctgaagc tgttattggt tacttggatt    180
tggaaggtga tttcgatgtt gctgttttgc cattctctaa ctctaccaac aatggtttgt    240
tgttcatcaa caccaccatt gcttctattg ctgctaaaga agaaggtgtt tctttggacg    300
gttctgctgg ttctggtgat gcagaattca gacatgattc tggttacgaa gttcaccacc    360
aaaagttggt ttttttcgct gaagatgtcg gttctaacaa gggtgctatt attggtttga    420
tggttggtgg tgtagttatt gctggttcag caggttcagc tggtagtgac gccgaattca    480
gacacgatag tggttatgaa gtccatcatc aaaaattagt tttctttgcc gaagatgttg    540
gtagtaacaa aggtgcaatc atcggtttaa tggtcggtgg tgtcgtaata gcaggtagtg    600
caggttccgc cggttctgat gccgaattca gacacgactc cggttatgaa gtacatcacc    660
aaaagttggt attcttcgca gaagatgtag gttcaaacaa aggtgccata ataggtttaa    720
tggttggtgg tgtcgttatc gcaggttctg ccggtagtgc tggttcagac gcagaattca    780
gacatgacag tggttacgaa gtacaccatc aaaaattagt cttttttgca gaagatgttg    840
gtagtaacaa gggtgctata ataggtttga tggtcggtgg tgtagtcata gcttaaaccc    900
agctttcttg tacaaagtgg tgcggccgca ctcgag                              936
```

<210> SEQ ID NO 3
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Met Arg Phe Pro Ser Ile Phe Thr Ala Val Leu Phe Ala Ala Ser Ser
1               5                  10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Asp Gly Ser Ala Gly Ser Gly Asp Ala Glu Phe Arg His Asp
                85                  90                  95
```

```
Ser Gly Tyr Glu Val His His Gln Lys Leu Val Phe Phe Ala Glu Asp
            100                 105                 110

Val Gly Ser Asn Lys Gly Ala Ile Ile Gly Leu Met Val Gly Gly Val
        115                 120                 125

Val Ile Ala Gly Ser Ala Gly Ser Ala Gly Ser Asp Ala Glu Phe Arg
    130                 135                 140

His Asp Ser Gly Tyr Glu Val His His Gln Lys Leu Val Phe Phe Ala
145                 150                 155                 160

Glu Asp Val Gly Ser Asn Lys Gly Ala Ile Ile Gly Leu Met Val Gly
                165                 170                 175

Gly Val Val Ile Ala Gly Ser Ala Gly Ser Ala Gly Ser Asp Ala Glu
            180                 185                 190

Phe Arg His Asp Ser Gly Tyr Glu Val His His Gln Lys Leu Val Phe
        195                 200                 205

Phe Ala Glu Asp Val Gly Ser Asn Lys Gly Ala Ile Ile Gly Leu Met
    210                 215                 220

Val Gly Gly Val Val Ile Ala Gly Ser Ala Gly Ser Ala Gly Ser Asp
225                 230                 235                 240

Ala Glu Phe Arg His Asp Ser Gly Tyr Glu Val His His Gln Lys Leu
                245                 250                 255

Val Phe Phe Ala Glu Asp Val Gly Ser Asn Lys Gly Ala Ile Ile Gly
            260                 265                 270

Leu Met Val Gly Gly Val Val Ile Ala
        275                 280

<210> SEQ ID NO 4
<211> LENGTH: 936
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gtcgactgga tccacaagtt tgtacaaaaa agcaggctgg taccaaaaga atgagattcc      60
catctatttt caccgctgtt tgtttgctg cttcttctgc tttggctgct ccagttaaca     120
ctactactga agatgaaact gctcaaattc cagctgaagc tgttattggt tacttggatt     180
tggaaggtga tttcgatgtt gctgttttgc cattctctaa ctctaccaac aatggtttgt     240
tgttcatcaa caccaccatt gcttctattg ctgctaaaga agaaggtgtc tctttggata     300
agagagaagc tgaagcagac gcagaattca gacatgattc tggttatgaa gttcaccacc     360
aaaagttggt tttcttcgct gaagatgttg gttctaacaa gggtgctatt atcggtttga     420
tggttggtgg tgtagttatt gctggttctg caggttcagc tggttcagat gccgaattca     480
gacacgatag tggttacgaa gtacatcatc aaaaattagt cttttttgcc gaagatgtcg     540
gtagtaacaa aggtgcaatc attggtttaa tggtcggtgg tgtcgtaata gcaggtagtg     600
ccggttctgc tggtagtgat gcagaattca gacacgactc cggttacgaa gtccatcacc     660
aaaagttggt attctttgcc gaagatgtcg gttcaaacaa gggtgccata ataggtttaa     720
tggttggtgg tgtcgttatc gccggtagtg ctggtagtgc aggttccgac gccgaattca     780
gacatgactc aggttacgaa gtacaccatc aaaagttggt attttttcgca gaagatgtag     840 gttccaacaa aggtgcaatc ataggtttga tggttggtgg tgtcgtaatt gcctaaaccc     900
agctttcttg tacaaagtgg tgcggccgca ctcgag                                936
```

<210> SEQ ID NO 5
<211> LENGTH: 281
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Asp Ala Glu Phe Arg His Asp
                85                  90                  95

Ser Gly Tyr Glu Val His His Gln Lys Leu Val Phe Phe Ala Glu Asp
            100                 105                 110

Val Gly Ser Asn Lys Gly Ala Ile Ile Gly Leu Met Val Gly Gly Val
        115                 120                 125

Val Ile Ala Gly Ser Ala Gly Ser Ala Gly Ser Asp Ala Glu Phe Arg
    130                 135                 140

His Asp Ser Gly Tyr Glu Val His His Gln Lys Leu Val Phe Phe Ala
145                 150                 155                 160

Glu Asp Val Gly Ser Asn Lys Gly Ala Ile Ile Gly Leu Met Val Gly
                165                 170                 175

Gly Val Val Ile Ala Gly Ser Ala Gly Ser Ala Gly Ser Asp Ala Glu
            180                 185                 190

Phe Arg His Asp Ser Gly Tyr Glu Val His His Gln Lys Leu Val Phe
        195                 200                 205

Phe Ala Glu Asp Val Gly Ser Asn Lys Gly Ala Ile Ile Gly Leu Met
    210                 215                 220

Val Gly Gly Val Val Ile Ala Gly Ser Ala Gly Ser Ala Gly Ser Asp
225                 230                 235                 240

Ala Glu Phe Arg His Asp Ser Gly Tyr Glu Val His His Gln Lys Leu
                245                 250                 255

Val Phe Phe Ala Glu Asp Val Gly Ser Asn Lys Gly Ala Ile Ile Gly
            260                 265                 270

Leu Met Val Gly Gly Val Val Ile Ala
        275                 280
```

<210> SEQ ID NO 6
<211> LENGTH: 936
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
gtcgactgga tccacaagtt tgtacaaaaa agcaggctgg taccaaaaga atgagattcc      60
catctatttt caccgctgtt tgtttgctg cttcttctgc tttggctgct ccagttaaca     120
```

```
ctactactga agatgaaact gctcaaattc cagctgaagc tgttattggt tacttggatt      180
tggaaggtga tttcgatgtt gctgttttgc cattctctaa ctctaccaac aatggtttgt      240
tgttcatcaa caccaccatt gcttctattg ctgctaaaga agaaggtgtc tctttggata      300
agagagaagc tgaagcagac gcagaattca gacatgattc tggttatgaa gttcaccacc      360
aaaagttggt tttcttcgct gaagatgttg gttctaacaa gggtgctatt atcggtttga      420
tggttggtgg tgtagttatt gctggttctg caggttcagc tggttcagat gccgaattca      480
gacacgatag tggttacgaa gtacatcatc aaaaattagt cttttttgcc gaagatgtcg      540
gtagtaacaa aggtgcaatc attggtttaa tggtcggtgg tgtcgtaatc gctaaaagag      600
aagccgacgc tgaagctgat gccgaattca gacatgactc aggttacgaa gtccatcacc      660
aaaagttggt attctttgcc gaagatgtcg gttcaaacaa gggtgccata ataggtttaa      720
tggttggtgg tgtcgttata gcaggtagtg ctggttccgc tggtagtgat gcagaattca      780
gacatgacag tggttatgaa gtccaccatc aaaaattggt cttttttcgca gaagatgtag      840 gttccaacaa aggtgcaatc ataggtttga tggttggtgg tgtcgtaatt gcctaaaccc      900
agctttcttg tacaaagtgg tgcggccgca ctcgag                                936
```

<210> SEQ ID NO 7
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Asp Ala Glu Phe Arg His Asp
                85                  90                  95

Ser Gly Tyr Glu Val His His Gln Lys Leu Val Phe Phe Ala Glu Asp
            100                 105                 110

Val Gly Ser Asn Lys Gly Ala Ile Ile Gly Leu Met Val Gly Gly Val
        115                 120                 125

Val Ile Ala Gly Ser Ala Gly Ser Ala Gly Ser Asp Ala Glu Phe Arg
    130                 135                 140

His Asp Ser Gly Tyr Glu Val His His Gln Lys Leu Val Phe Phe Ala
145                 150                 155                 160

Glu Asp Val Gly Ser Asn Lys Gly Ala Ile Ile Gly Leu Met Val Gly
                165                 170                 175

Gly Val Val Ile Ala Lys Arg Glu Ala Asp Ala Glu Ala Asp Ala Glu
            180                 185                 190

Phe Arg His Asp Ser Gly Tyr Glu Val His His Gln Lys Leu Val Phe
        195                 200                 205

```
Phe Ala Glu Asp Val Gly Ser Asn Lys Gly Ala Ile Ile Gly Leu Met
    210                 215                 220
Val Gly Gly Val Val Ile Ala Gly Ser Ala Gly Ser Ala Gly Ser Asp
225                 230                 235                 240
Ala Glu Phe Arg His Asp Ser Gly Tyr Glu Val His His Gln Lys Leu
            245                 250                 255
Val Phe Phe Ala Glu Asp Val Gly Ser Asn Lys Gly Ala Ile Ile Gly
        260                 265                 270
Leu Met Val Gly Gly Val Val Ile Ala
        275                 280
```

<210> SEQ ID NO 8
<211> LENGTH: 480
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
gtcgactgga tccacaagtt tgtacaaaaa agcaggctgg taccaaaaga atgagatttc    60
cttcaatttt tactgcagtt ttattcgcag catcctccgc attagctgct ccagtcaaca   120
ctacaacaga agatgaaacg gcacaaattc cggctgaagc tgtcatcggt tacttagatt   180
tagaagggga tttcgatgtt gctgttttgc catttccaa cagcacaaat aacgggttat    240
tgtttataaa tactactatt gccagcattg ctgctaaaga agaagggggta tctttggata   300
aaagagaggc tgaagctgat gctgaattta gacatgattc tggttatgaa gttcatcatc   360
aaaaattggt ttttttttgct gaagatgttg gttctaataa aggtgctatt attggtttga   420
tggttggtgg tgttgtctaa acccagcttt cttgtacaaa gtggtgcggc cgcactcgag   480
```

<210> SEQ ID NO 9
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Met Arg Phe Pro Ser Ile Phe Thr Ala Val Leu Phe Ala Ala Ser Ser
1               5                   10                  15
Ala Leu Ala Ala Pro Val Asn Thr Thr Thr Glu Asp Glu Thr Ala Gln
            20                  25                  30
Ile Pro Ala Glu Ala Val Ile Gly Tyr Leu Asp Leu Glu Gly Asp Phe
        35                  40                  45
Asp Val Ala Val Leu Pro Phe Ser Asn Ser Thr Asn Asn Gly Leu Leu
    50                  55                  60
Phe Ile Asn Thr Thr Ile Ala Ser Ile Ala Ala Lys Glu Glu Gly Val
65                  70                  75                  80
Ser Leu Asp Lys Arg Glu Ala Glu Ala Asp Ala Glu Phe Arg His Asp
                85                  90                  95
Ser Gly Tyr Glu Val His His Gln Lys Leu Val Phe Phe Ala Glu Asp
            100                 105                 110
Val Gly Ser Asn Lys Gly Ala Ile Ile Gly Leu Met Val Gly Gly Val
        115                 120                 125
Val
```

<210> SEQ ID NO 10
<211> LENGTH: 624
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 10

```
gtcgactgga tccacaagtt tgtacaaaaa agcaggctgg taccaaaaga atgagattcc      60
catctatttt caccgctgtt ttgtttgctg cttcttctgc tttggctgct ccagttaaca     120
ctactactga agatgaaact gctcaaattc cagctgaagc tgttattggt tacttggatt     180
tggaaggtga tttcgatgtt gctgttttgc cattctctaa ctctaccaac aatggtttgt     240
tgttcatcaa caccaccatt gcttctattg ctgctaaaga agaaggtgtc tctttggata     300
agagagaagc tgaagcagac gcagaattca gacatgattc tggttatgaa gttcaccacc     360
aaaagttggt tttcttcgct gaagatgttg gttctaacaa gggtgctatt atcggtttga     420
tggttggtgg tgtagtaaaa agagaagccg aagctgaagc tgatgccgaa ttcagacacg     480
atagtggtta cgaagtacat catcaaaaat tagtcttttt tgccgaagat gtcggtagta     540
acaaaggtgc aatcattggt ttaatggtcg gtggtgtcgt ttgaacccag ctttcttgta     600
caaagtggtg cggccgcact cgag                                            624
```

<210> SEQ ID NO 11
<211> LENGTH: 177
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 11

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Leu Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Asp Ala Glu Phe Arg His Asp
                85                  90                  95

Ser Gly Tyr Glu Val His His Gln Lys Leu Val Phe Phe Ala Glu Asp
                100                 105                 110

Val Gly Ser Asn Lys Gly Ala Ile Ile Gly Leu Met Val Gly Gly Val
            115                 120                 125

Val Lys Arg Glu Ala Glu Ala Glu Asp Ala Glu Phe Arg His Asp
        130                 135                 140

Ser Gly Tyr Glu Val His His Gln Lys Leu Val Phe Phe Ala Glu Asp
145                 150                 155                 160

Val Gly Ser Asn Lys Gly Ala Ile Ile Gly Leu Met Val Gly Gly Val
                165                 170                 175

Val
```

<210> SEQ ID NO 12
<211> LENGTH: 924
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

| | | | | | |
|---|---|---|---|---|---|
| gtcgactgga | tccacaagtt | tgtacaaaaa | agcaggctgg | taccaaaaga | atgagattcc    60 |
| catctatttt | caccgctgtt | ttgtttgctg | cttcttctgc | tttggctgct | ccagttaaca   120 |
| ctactactga | agatgaaact | gctcaaattc | cagctgaagc | tgttattggt | tacttggatt   180 |
| tggaaggtga | tttcgatgtt | gctgttttgc | cattctctaa | ctctaccaac | aatggtttgt   240 |
| tgttcatcaa | caccaccatt | gcttctattg | ctgctaaaga | agaaggtgtc | tctttggata   300 |
| agagagaagc | tgaagcagac | gcagaattca | gacatgattc | tggttatgaa | gttcaccacc   360 |
| aaaagttggt | tttcttcgct | gaagatgttg | gttctaacaa | gggtgctatt | atcggtttga   420 |
| tggttggtgg | tgtagttatt | gctaaaagag | aagccgaagc | tgaagctgat | gccgaattca   480 |
| gacacgatag | tggttacgaa | gtacatcatc | aaaaattagt | cttttttgcc | gaagatgtcg   540 |
| gtagtaacaa | aggtgcaatc | attggtttaa | tggtcggtgg | tgtcgtaata | gccaagagag   600 |
| aagcagacgc | cgaagccgat | gcagaattca | gacacgactc | cggttacgaa | gtccatcacc   660 |
| aaaagttggt | attctttgcc | gaagatgtcg | gttcaaacaa | gggtgccata | ataggtttaa   720 |
| tggttggtgg | tgtcgttaag | agagaagctg | acgctgaagc | agacgccgaa | ttcagacacg   780 |
| actcaggtta | tgaagtacac | catcaaaaat | tggtattttt | cgcagaagat | gttggttcca   840 |
| acaaaggtgc | cattattggt | ttgatggttg | gtggtgtcgt | ttaaacccag | ctttcttgta   900 |
| caaagtggtg | cggccgcact | cgag | | |              924 |

<210> SEQ ID NO 13
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Asp Ala Glu Phe Arg His Asp
                85                  90                  95

Ser Gly Tyr Glu Val His His Gln Lys Leu Val Phe Phe Ala Glu Asp
            100                 105                 110

Val Gly Ser Asn Lys Gly Ala Ile Ile Gly Leu Met Val Gly Gly Val
        115                 120                 125

Val Ile Ala Lys Arg Glu Ala Glu Ala Glu Ala Asp Ala Glu Phe Arg

```
                130                 135                 140
His Asp Ser Gly Tyr Glu Val His His Gln Lys Leu Val Phe Phe Ala
145                 150                 155                 160

Glu Asp Val Gly Ser Asn Lys Gly Ala Ile Ile Gly Leu Met Val Gly
                165                 170                 175

Gly Val Val Ile Ala Lys Arg Glu Ala Asp Ala Glu Ala Asp Ala Glu
            180                 185                 190

Phe Arg His Asp Ser Gly Tyr Glu Val His His Gln Lys Leu Val Phe
        195                 200                 205

Phe Ala Glu Asp Val Gly Ser Asn Lys Gly Ala Ile Ile Gly Leu Met
    210                 215                 220

Val Gly Gly Val Val Lys Arg Glu Ala Asp Ala Glu Ala Asp Ala Glu
225                 230                 235                 240

Phe Arg His Asp Ser Gly Tyr Glu Val His His Gln Lys Leu Val Phe
                245                 250                 255

Phe Ala Glu Asp Val Gly Ser Asn Lys Gly Ala Ile Ile Gly Leu Met
            260                 265                 270

Val Gly Gly Val Val
        275

<210> SEQ ID NO 14
<211> LENGTH: 924
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
gtcgactgga tccacaagtt tgtacaaaaa agcaggctgg taccaaaaga atgagattcc      60
catctatttt caccgctgtt ttgtttgctg cttcttctgc tttggctgct ccagttaaca     120
ctactactga agatgaaact gctcaaattc agctgaagc tgttattggt tacttggatt     180
tggaaggtga tttcgatgtt gctgttttgc cattctctaa ctctaccaac aatggtttgt     240
tgttcatcaa caccaccatt gcttctattg ctgctaaaga agaaggtgtc tctttggata     300
agagagaagc tgaagcagac gcagaattca gacatgattc tggttatgaa gttcaccacc     360
aaaagttggt tttcttcgct gaagatgttg gttctaacaa gggtgctatt atcggtttga     420
tggttggtgg tgtagttatt gctaaaagag aagccgaagc tgaagctgat gccgaattca     480
gacacgatag tggttacgaa gtacatcatc aaaaattagt cttttttgcc gaagatgtcg     540
gtagtaacaa aggtgcaatc attggtttaa tggtcggtgg tgtcgtaata gccaagagag     600
aagcagacgc cgaagctgct attgctgaag gtgattcaca tgttttgaaa gaaggtgcct     660
acatggaaat cttcgatgtt caaggtcatg ttttcggtgg taagatcttc agagttgttg     720
atttgggttc ccacaacaaa agagaagctg acgcagaagc cgcaatagcc gaaggtgact     780
ctcacgtctt aaaagaaggt gcttatatgg aaatttttga cgtccaaggt cacgtctttg     840
gtggtaagat ttttagagta gtcgacttgg gtagtcataa ctaaacccag ctttcttgta     900
caaagtggtg cggccgcact cgag                                            924

<210> SEQ ID NO 15
<211> LENGTH: 277
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 15

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Asp Ala Glu Phe Arg His Asp
                85                  90                  95

Ser Gly Tyr Glu Val His His Gln Lys Leu Val Phe Phe Ala Glu Asp
            100                 105                 110

Val Gly Ser Asn Lys Gly Ala Ile Ile Gly Leu Met Val Gly Gly Val
        115                 120                 125

Val Ile Ala Lys Arg Glu Ala Glu Ala Asp Ala Glu Phe Arg
    130                 135                 140

His Asp Ser Gly Tyr Glu Val His His Gln Lys Leu Val Phe Phe Ala
145                 150                 155                 160

Glu Asp Val Gly Ser Asn Lys Gly Ala Ile Ile Gly Leu Met Val Gly
                165                 170                 175

Gly Val Val Ile Ala Lys Arg Glu Ala Asp Ala Glu Ala Ala Ile Ala
            180                 185                 190

Glu Gly Asp Ser His Val Leu Lys Glu Gly Ala Tyr Met Glu Ile Phe
        195                 200                 205

Asp Val Gln Gly His Val Phe Gly Gly Lys Ile Phe Arg Val Val Asp
    210                 215                 220

Leu Gly Ser His Asn Lys Arg Glu Ala Asp Ala Glu Ala Ala Ile Ala
225                 230                 235                 240

Glu Gly Asp Ser His Val Leu Lys Glu Gly Ala Tyr Met Glu Ile Phe
                245                 250                 255

Asp Val Gln Gly His Val Phe Gly Gly Lys Ile Phe Arg Val Val Asp
            260                 265                 270

Leu Gly Ser His Asn
        275
```

<210> SEQ ID NO 16
<211> LENGTH: 205
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

```
caccatggcc ctgtggatgc gcctcctgcc cctgctggcg ctgctggccc tctggggacc    60
tgacccagcc gcagccgatg cggaatttcg ccatgattct ggctatgaag tgcatcatca   120
gaaactggtg ttttttgcgg gagatgtggg ctctaacaaa ggcgcgatta ttggcctgat   180
ggtgggcggc gtggtgattg cgtaa                                         205
```

<210> SEQ ID NO 17

<210> SEQ ID NO 17
<211> LENGTH: 66
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Ala Leu Trp Met Arg Leu Leu Pro Leu Leu Ala Leu Leu Ala Leu
1               5                   10                  15

Trp Gly Pro Asp Pro Ala Ala Asp Ala Glu Phe Arg His Asp Ser
            20                  25                  30

Gly Tyr Glu Val His His Gln Lys Leu Val Phe Phe Ala Gly Asp Val
        35                  40                  45

Gly Ser Asn Lys Gly Ala Ile Ile Gly Leu Met Val Gly Gly Val Val
    50                  55                  60

Ile Ala
65

<210> SEQ ID NO 18
<211> LENGTH: 205
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
caccatggcc ctgtggatgc gcctcctgcc cctgctggcg ctgctggccc tctggggacc      60
tgacccagcc gcagccgatg cggaatttcg ccatgattct ggctatgaag tgcatcatca     120
gaaactggtg tttgaggcgg aagatgtggg ctctaacaaa ggcgcgatta ttggcctgat     180
ggtgggcggc gtggtgattg cgtaa                                           205

<210> SEQ ID NO 19
<211> LENGTH: 66
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Ala Leu Trp Met Arg Leu Leu Pro Leu Leu Ala Leu Leu Ala Leu
1               5                   10                  15

Trp Gly Pro Asp Pro Ala Ala Asp Ala Glu Phe Arg His Asp Ser
            20                  25                  30

Gly Tyr Glu Val His His Gln Lys Leu Val Phe Glu Ala Glu Asp Val
        35                  40                  45

Gly Ser Asn Lys Gly Ala Ile Ile Gly Leu Met Val Gly Gly Val Val
    50                  55                  60

Ile Ala
65

<210> SEQ ID NO 20
<211> LENGTH: 205
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
caccatggcc ctgtggatgc gcctcctgcc cctgctggcg ctgctggccc tctggggacc      60
tgacccagcc gcagccgatg cggaatttcg ccatgattct ggctatgaag tgcatcatca     120
gaaactggtg ttttttgcgg aagatgtggg ctctaacaaa ggcgcggaga ttggcctgat     180
ggtgggcggc gtggtgattg cgtaa                                           205
```

<210> SEQ ID NO 21
<211> LENGTH: 66
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

Met Ala Leu Trp Met Arg Leu Leu Pro Leu Leu Ala Leu Leu Ala Leu
1               5                   10                  15

Trp Gly Pro Asp Pro Ala Ala Ala Asp Ala Glu Phe Arg His Asp Ser
            20                  25                  30

Gly Tyr Glu Val His His Gln Lys Leu Val Phe Phe Ala Glu Asp Val
        35                  40                  45

Gly Ser Asn Lys Gly Ala Glu Ile Gly Leu Met Val Gly Gly Val Val
    50                  55                  60

Ile Ala
65

<210> SEQ ID NO 22
<211> LENGTH: 205
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
caccatggcc ctgtggatgc gcctcctgcc cctgctggcg ctgctggccc tctggggacc      60
tgacccagcc gcagccgatg cggaatttcg ccatgattct ggctatgaag tgcatcatca     120
gaaactggtg ttttttgcgg agatgtggg ctctaacaaa ggcgcggaga ttggcctgat      180
ggtgggcggc gtggtgattg cgtaa                                           205
```

<210> SEQ ID NO 23
<211> LENGTH: 66
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

Met Ala Leu Trp Met Arg Leu Leu Pro Leu Leu Ala Leu Leu Ala Leu
1               5                   10                  15

Trp Gly Pro Asp Pro Ala Ala Ala Asp Ala Glu Phe Arg His Asp Ser
            20                  25                  30

Gly Tyr Glu Val His His Gln Lys Leu Val Phe Phe Ala Gly Asp Val
        35                  40                  45

Gly Ser Asn Lys Gly Ala Glu Ile Gly Leu Met Val Gly Gly Val Val
    50                  55                  60

Ile Ala
65

<210> SEQ ID NO 24
<211> LENGTH: 172
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
caccatgtct gcacttctga tcctagctct tgttggagct gcagttgctg atgcggaatt      60
tcgccatgat tctggctatg aagtgcatca tcagaaactg gtgttttttg cggaagatgt     120
gggctctaac aaaggcgcga ttattggcct gatggtgggc ggcgtggtgt aa             172

<210> SEQ ID NO 25
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Ser Ala Leu Leu Ile Leu Ala Leu Val Gly Ala Ala Val Ala Asp
1               5                   10                  15

Ala Glu Phe Arg His Asp Ser Gly Tyr Glu Val His His Gln Lys Leu
            20                  25                  30

Val Phe Phe Ala Glu Asp Val Gly Ser Asn Lys Gly Ala Ile Ile Gly
        35                  40                  45

Leu Met Val Gly Gly Val Val
    50                  55

<210> SEQ ID NO 26
<211> LENGTH: 178
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
caccatgctg ctgctgctgc tgctgctggg cctgaggcta cagctctccc tgggcgatgc      60
ggaatttcgc catgattctg gctatgaagt gcatcatcag aaactggtgt tttttgcgga     120
agatgtgggc tctaacaaag gcgcgattat tggcctgatg gtgggcggcg tggtgtaa      178

<210> SEQ ID NO 27
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Leu Leu Leu Leu Leu Leu Gly Leu Arg Leu Gln Leu Ser Leu
1               5                   10                  15

Gly Asp Ala Glu Phe Arg His Asp Ser Gly Tyr Glu Val His His Gln
            20                  25                  30

Lys Leu Val Phe Phe Ala Glu Asp Val Gly Ser Asn Lys Gly Ala Ile
        35                  40                  45

Ile Gly Leu Met Val Gly Gly Val Val 50                  55

<210> SEQ ID NO 28
<211> LENGTH: 178
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
caccatggac atcaaggtgg tgttcaccct ggtgttcagc gccctggtgc aggccgatgc    60
ggaatttcgc catgattctg gctatgaagt gcatcatcag aaactggtgt tttttgcgga   120
agatgtgggc tctaacaaag gcgcgattat tggcctgatg gtgggcggcg tggtgtaa    178

<210> SEQ ID NO 29
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Asp Ile Lys Val Val Phe Thr Leu Val Phe Ser Ala Leu Val Gln
1               5                   10                  15

Ala Asp Ala Glu Phe Arg His Asp Ser Gly Tyr Glu Val His His Gln
            20                  25                  30

Lys Leu Val Phe Phe Ala Glu Asp Val Gly Ser Asn Lys Gly Ala Ile
        35                  40                  45

Ile Gly Leu Met Val Gly Gly Val Val
    50                  55

<210> SEQ ID NO 30
<211> LENGTH: 178
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
caccatgctg cccggtttgg cactgctcct gctggccgcc tggacggctc gggcggatgc    60
ggaatttcgc catgattctg gctatgaagt gcatcatcag aaactggtgt tttttgcgga   120
agatgtgggc tctaacaaag gcgcgattat tggcctgatg gtgggcggcg tggtgtaa    178

<210> SEQ ID NO 31
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Leu Pro Gly Leu Ala Leu Leu Leu Ala Ala Trp Thr Ala Arg
1               5                   10                  15

Ala Asp Ala Glu Phe Arg His Asp Ser Gly Tyr Glu Val His His Gln
            20                  25                  30

Lys Leu Val Phe Phe Ala Glu Asp Val Gly Ser Asn Lys Gly Ala Ile
        35                  40                  45

```
Ile Gly Leu Met Val Gly Gly Val Val
    50                  55
```

<210> SEQ ID NO 32
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
caccatggat gcggaatttc gccatgattc tggctatgaa gtgcatcatc agaaactggt     60
gttttttgcg gaagatgtgg gctctaacaa aggcgcgatt attggcctga tggtgggcgg    120
cgtggtgtaa                                                           130

<210> SEQ ID NO 33
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Met Asp Ala Glu Phe Arg His Asp Ser Gly Tyr Glu Val His His Gln
1               5                   10                  15

Lys Leu Val Phe Phe Ala Glu Asp Val Gly Ser Asn Lys Gly Ala Ile
            20                  25                  30

Ile Gly Leu Met Val Gly Gly Val Val
        35                  40
```

<210> SEQ ID NO 34
<211> LENGTH: 601
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
caccatggcc ctgtggatga gactgctgcc cctgctggct ctgctggcac tgtggggacc     60
tgatcctgcc gccgctgatg ccgagttcag cacgatagc ggctacgagg tgcaccacca    120
gaaactggtg ttcttcgccg aggacgtggg cagcaacaag ggcgccatca tcggcctgat    180
ggtgggaggc gtcgtgatcg ccagaaggga cgccgagttt aggcacgact ctggatatga    240
agtgcatcat cagaaactgg tgttttttgc tgaagatgtg gggtccaaca agggggccat    300
tattggactg atggtgggcg gagtcgtgat tgctaagcgc gacgccgaat ccggcacga    360 ttccggctac gaagtgcacc atcagaaact ggtgtttttc gcagaggatg tgggctctaa    420
caagggggct atcatcggac tgatggtggg cggggtcgtg atcgctcgga gagatgccga    480
gttccggcat gacagcggat atgaagtgca ccaccagaaa ctggtgtttt tgccgagga    540 tgtgggaagt aacaaagggg caatcattgg cctgatggtg ggaggggtcg tgattgcctg    600
a                                                                   601

<210> SEQ ID NO 35
<211> LENGTH: 198
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 35

```
Met Ala Leu Trp Met Arg Leu Leu Pro Leu Leu Ala Leu Leu Ala Leu
1               5                   10                  15
Trp Gly Pro Asp Pro Ala Ala Ala Asp Ala Glu Phe Arg His Asp Ser
            20                  25                  30
Gly Tyr Glu Val His His Gln Lys Leu Val Phe Phe Ala Glu Asp Val
        35                  40                  45
Gly Ser Asn Lys Gly Ala Ile Ile Gly Leu Met Val Gly Gly Val Val
    50                  55                  60
Ile Ala Arg Arg Asp Ala Glu Phe Arg His Asp Ser Gly Tyr Glu Val
65                  70                  75                  80
His His Gln Lys Leu Val Phe Phe Ala Glu Asp Val Gly Ser Asn Lys
                85                  90                  95
Gly Ala Ile Ile Gly Leu Met Val Gly Gly Val Val Ile Ala Lys Arg
            100                 105                 110
Asp Ala Glu Phe Arg His Asp Ser Gly Tyr Glu Val His His Gln Lys
        115                 120                 125
Leu Val Phe Phe Ala Glu Asp Val Gly Ser Asn Lys Gly Ala Ile Ile
    130                 135                 140
Gly Leu Met Val Gly Gly Val Val Ile Ala Arg Arg Asp Ala Glu Phe
145                 150                 155                 160
Arg His Asp Ser Gly Tyr Glu Val His His Gln Lys Leu Val Phe Phe
                165                 170                 175
Ala Glu Asp Val Gly Ser Asn Lys Gly Ala Ile Ile Gly Leu Met Val
            180                 185                 190
Gly Gly Val Val Ile Ala
        195
```

<210> SEQ ID NO 36
<211> LENGTH: 601
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 36

```
caccatggcc ctgtggatga gactgctgcc cctgctggct ctgctggcac tgtggggacc      60
tgatcctgcc gccgctgatg ccgagttcag acacgatagc ggctacgagg tgcaccacca    120
gaaactggtg ttctttgccg cgacgtgggg cagcaacaag ggcgccatca tcggcctgat    180
ggtgggaggc gtcgtgatcg ccagaaggga cgccgagttt aggcacgact ctggatatga    240
agtgcatcat cagaaactgg tgttttttcgc tggggatgtg gggtccaaca aaggggccat    300
tattggactg atggtgggcg gagtcgtgat tgctaagcgc gacgccgaat tccggcacga    360
ttccggctac gaagtgcacc atcagaaact ggtgttcttc gccggggacg tgggatctaa    420
caagggggct atcattgggc tgatggtggg aggggtcgtg attgctcggc gggatgctga    480
gttccggcat gacagcggat atgaggtgca ccatcagaaa ctggtgtttt ttgccgggga    540
cgtgggctca aacaaaggcg caattatcgg gctgatggtg ggcggggtcg tgatcgctta    600
a                                                                    601
```

<210> SEQ ID NO 37

<211> LENGTH: 198
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

```
Met Ala Leu Trp Met Arg Leu Leu Pro Leu Leu Ala Leu Leu Ala Leu
1               5                   10                  15
Trp Gly Pro Asp Pro Ala Ala Asp Ala Glu Phe Arg His Asp Ser
            20                  25                  30
Gly Tyr Glu Val His His Gln Lys Leu Val Phe Phe Ala Gly Asp Val
        35                  40                  45
Gly Ser Asn Lys Gly Ala Ile Ile Gly Leu Met Val Gly Gly Val Val
    50                  55                  60
Ile Ala Arg Arg Asp Ala Glu Phe Arg His Asp Ser Gly Tyr Glu Val
65                  70                  75                  80
His His Gln Lys Leu Val Phe Phe Ala Gly Asp Val Gly Ser Asn Lys
                85                  90                  95
Gly Ala Ile Ile Gly Leu Met Val Gly Gly Val Val Ile Ala Lys Arg
            100                 105                 110
Asp Ala Glu Phe Arg His Asp Ser Gly Tyr Glu Val His His Gln Lys
        115                 120                 125
Leu Val Phe Phe Ala Gly Asp Val Gly Ser Asn Lys Gly Ala Ile Ile
    130                 135                 140
Gly Leu Met Val Gly Gly Val Val Ile Ala Arg Arg Asp Ala Glu Phe
145                 150                 155                 160
Arg His Asp Ser Gly Tyr Glu Val His His Gln Lys Leu Val Phe Phe
                165                 170                 175
Ala Gly Asp Val Gly Ser Asn Lys Gly Ala Ile Ile Gly Leu Met Val
            180                 185                 190
Gly Gly Val Val Ile Ala
        195
```

<210> SEQ ID NO 38
<211> LENGTH: 865
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38

| | | | | | |
|---|---|---|---|---|---|
| caccatggcc | ctgtggatga | gactgctgcc | cctgctggct | ctgctggcac | tgtggggacc | 60 |
| tgatcctgcc | gccgctgatg | ccgagttcag | acacgatagc | ggctacgagg | tgcaccacca | 120 |
| gaaactggtg | ttcttcgccg | gagacgtggg | cagcaacaag | ggcgccatca | tcggcctgat | 180 |
| ggtgggaggc | gtcgtgatcg | ccagaaggga | cgccgagttt | aggcacgact | ctggatatga | 240 |
| agtgcatcat | cagaaactgg | tgttttttgc | tgaagatgtg | gggtccaaca | aggggccat | 300 |
| tattggactg | atggtgggcg | gagtcgtgat | tgctaagcgc | gacgccgaat | tccggcacga | 360 |
| ttccggctac | gaagtgcacc | atcagaaact | ggtgttttc | gcagaggatg | tgggctctaa | 420 |
| caagggggct | atcatcggac | tgatggtggg | cggggtcgtg | atcgctcgga | gagatgccga | 480 |
| gttccggcat | gacagcggat | atgaagtgca | ccaccagaaa | ctggtgtttt | ttgccgagga | 540 |
| tgtgggaagt | aacaaagggg | caatcattgg | cctgatggtg | ggaggggtcg | tgattgctaa | 600 |

```
acgggatgct gagttccgcc acgactcagg ctatgaggtg caccatcaga aactggtgtt    660
ctttgccgaa gatgtgggat ctaacaaggg cgcaattatt gggctgatgg tgggcggcgt    720
cgtgatcgca agacgggatg cagaattcag acatgactcc ggatacgagg tgcaccatca    780
gaaactggtg ttttttgctg aggacgtggg gagcaacaaa ggggctatta tcgggctgat    840
ggtgggaggc gtcgtgattg cctga                                          865
```

<210> SEQ ID NO 39
<211> LENGTH: 286
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Met Ala Leu Trp Met Arg Leu Leu Pro Leu Leu Ala Leu Leu Ala Leu
1               5                   10                  15

Trp Gly Pro Asp Pro Ala Ala Ala Asp Ala Glu Phe Arg His Asp Ser
            20                  25                  30

Gly Tyr Glu Val His His Gln Lys Leu Val Phe Phe Ala Glu Asp Val
        35                  40                  45

Gly Ser Asn Lys Gly Ala Ile Ile Gly Leu Met Val Gly Gly Val Val
    50                  55                  60

Ile Ala Arg Arg Asp Ala Glu Phe Arg His Asp Ser Gly Tyr Glu Val
65                  70                  75                  80

His His Gln Lys Leu Val Phe Phe Ala Glu Asp Val Gly Ser Asn Lys
                85                  90                  95

Gly Ala Ile Ile Gly Leu Met Val Gly Gly Val Val Ile Ala Lys Arg
            100                 105                 110

Asp Ala Glu Phe Arg His Asp Ser Gly Tyr Glu Val His His Gln Lys
        115                 120                 125

Leu Val Phe Phe Ala Glu Asp Val Gly Ser Asn Lys Gly Ala Ile Ile
    130                 135                 140

Gly Leu Met Val Gly Gly Val Val Ile Ala Arg Arg Asp Ala Glu Phe
145                 150                 155                 160

Arg His Asp Ser Gly Tyr Glu Val His His Gln Lys Leu Val Phe Phe
                165                 170                 175

Ala Glu Asp Val Gly Ser Asn Lys Gly Ala Ile Ile Gly Leu Met Val
            180                 185                 190

Gly Gly Val Val Ile Ala Lys Arg Asp Ala Glu Phe Arg His Asp Ser
        195                 200                 205

Gly Tyr Glu Val His His Gln Lys Leu Val Phe Phe Ala Glu Asp Val
    210                 215                 220

Gly Ser Asn Lys Gly Ala Ile Ile Gly Leu Met Val Gly Gly Val Val
225                 230                 235                 240

Ile Ala Arg Arg Asp Ala Glu Phe Arg His Asp Ser Gly Tyr Glu Val
                245                 250                 255

His His Gln Lys Leu Val Phe Phe Ala Glu Asp Val Gly Ser Asn Lys
            260                 265                 270

Gly Ala Ile Ile Gly Leu Met Val Gly Gly Val Val Ile Ala
        275                 280                 285
```

<210> SEQ ID NO 40
<211> LENGTH: 577
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 40

```
caccatggcc ctgtggatga gactgctgcc cctgctggct ctgctggcac tgtggggacc      60
tgatcctgcc gccgctgatg ccgagttcag acacgatagc ggctacgagg tgcaccacca    120
gaaactggtg ttcttcgccg aggacgtggg cagcaacaag ggcgccatca tcggcctgat    180
ggtgggaggc gtcgtgcgga gagatgccga attccggcac gactccggat atgaagtgca    240
tcatcagaaa ctggtgtttt ttgctgaaga tgtggggtcc aacaaagggg ccattattgg    300
actgatggtg ggcggagtcg tgaagcggga cgccgagttt aggcatgact ctggctacga    360
agtgcaccat cagaaactgg tgttttcgc agaggatgtg ggctctaaca agggggctat    420
catcggactg atggtgggcg gggtcgtgcg cagagatgct gagtttagac acgattctgg    480
atatgaagtg caccaccaga aactggtgtt ttttgccgag gatgtgggaa gtaacaaagg    540
ggcaatcatt ggcctgatgg tgggaggggt ggtgtaa                             577
```

<210> SEQ ID NO 41
<211> LENGTH: 190
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

```
Met Ala Leu Trp Met Arg Leu Leu Pro Leu Leu Ala Leu Leu Ala Leu
1               5                   10                  15

Trp Gly Pro Asp Pro Ala Ala Ala Asp Ala Glu Phe Arg His Asp Ser
            20                  25                  30

Gly Tyr Glu Val His His Gln Lys Leu Val Phe Phe Ala Glu Asp Val
        35                  40                  45

Gly Ser Asn Lys Gly Ala Ile Ile Gly Leu Met Val Gly Gly Val Val
    50                  55                  60

Arg Arg Asp Ala Glu Phe Arg His Asp Ser Gly Tyr Glu Val His His
65                  70                  75                  80

Gln Lys Leu Val Phe Phe Ala Glu Asp Val Gly Ser Asn Lys Gly Ala
                85                  90                  95

Ile Ile Gly Leu Met Val Gly Gly Val Val Lys Arg Asp Ala Glu Phe
            100                 105                 110

Arg His Asp Ser Gly Tyr Glu Val His His Gln Lys Leu Val Phe Phe
        115                 120                 125

Ala Glu Asp Val Gly Ser Asn Lys Gly Ala Ile Ile Gly Leu Met Val
    130                 135                 140

Gly Gly Val Val Arg Arg Asp Ala Glu Phe Arg His Asp Ser Gly Tyr
145                 150                 155                 160

Glu Val His His Gln Lys Leu Val Phe Phe Ala Glu Asp Val Gly Ser
                165                 170                 175

Asn Lys Gly Ala Ile Ile Gly Leu Met Val Gly Gly Val Val
            180                 185                 190
```

<210> SEQ ID NO 42
<211> LENGTH: 829
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 42

```
caccatggcc ctgtggatga gactgctgcc cctgctggct ctgctggcac tgtggggacc     60
tgatcctgcc gccgctgatg ccgagttcag acacgatagc ggctacgagg tgcaccacca    120
gaaactggtg ttcttcgccg aggacgtggg cagcaacaag ggcgccatca tcggcctgat    180
ggtgggaggc gtcgtgcgga gagatgccga attccggcac gactccggat atgaagtgca    240
tcatcagaaa ctggtgtttt ttgctgaaga tgtggggtcc aacaaagggg ccattattgg    300
actgatggtg ggcggagtcg tgaagcggga cgccgagttt aggcatgact ctggctacga    360
agtgcaccat cagaaactgg tgtttttcgc agaggatgtg ggctctaaca agggggctat    420
catcggactg atggtgggcg gggtcgtgcg cagagatgct gagtttagac acgattctgg    480
atatgaagtg caccaccaga aactggtgtt ttttgccgag gatgtgggaa gtaacaaagg    540
ggcaatcatt ggcctgatgg tgggaggggt cgtgaaaagg gatgcagagt ttcggcacga    600
cagtggctat gaagtgcatc accagaaact ggtgttcttc gcagaagatg tggggagtaa    660
caagggcgct attatcgggc tgatggtggg cggagtcgtg cggagggacg ctgagttccg    720
ccatgacagc ggatatgagg tgcaccatca gaaactggtg ttctttgccg aagatgtggg    780
atcaaacaag ggcgcaatca ttgggctgat ggtgggcggc gtggtgtaa                829
```

<210> SEQ ID NO 43
<211> LENGTH: 274
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 43

```
Met Ala Leu Trp Met Arg Leu Leu Pro Leu Leu Ala Leu Leu Ala Leu
1               5                   10                  15

Trp Gly Pro Asp Pro Ala Ala Ala Asp Ala Glu Phe Arg His Asp Ser
            20                  25                  30

Gly Tyr Glu Val His His Gln Lys Leu Val Phe Phe Ala Glu Asp Val
        35                  40                  45

Gly Ser Asn Lys Gly Ala Ile Ile Gly Leu Met Val Gly Gly Val Val
    50                  55                  60

Arg Arg Asp Ala Glu Phe Arg His Asp Ser Gly Tyr Glu Val His His
65                  70                  75                  80

Gln Lys Leu Val Phe Phe Ala Glu Asp Val Gly Ser Asn Lys Gly Ala
                85                  90                  95

Ile Ile Gly Leu Met Val Gly Gly Val Val Lys Arg Asp Ala Glu Phe
            100                 105                 110

Arg His Asp Ser Gly Tyr Glu Val His His Gln Lys Leu Val Phe Phe
        115                 120                 125

Ala Glu Asp Val Gly Ser Asn Lys Gly Ala Ile Ile Gly Leu Met Val
    130                 135                 140

Gly Gly Val Val Arg Arg Asp Ala Glu Phe Arg His Asp Ser Gly Tyr
145                 150                 155                 160

Glu Val His His Gln Lys Leu Val Phe Phe Ala Glu Asp Val Gly Ser
                165                 170                 175

Asn Lys Gly Ala Ile Ile Gly Leu Met Val Gly Gly Val Val Lys Arg
```

```
                    180                 185                 190
Asp Ala Glu Phe Arg His Asp Ser Gly Tyr Glu Val His His Gln Lys
            195                 200                 205

Leu Val Phe Phe Ala Glu Asp Val Gly Ser Asn Lys Gly Ala Ile Ile
        210                 215                 220

Gly Leu Met Val Gly Gly Val Val Arg Arg Asp Ala Glu Phe Arg His
225                 230                 235                 240

Asp Ser Gly Tyr Glu Val His His Gln Lys Leu Val Phe Phe Ala Glu
            245                 250                 255

Asp Val Gly Ser Asn Lys Gly Ala Ile Ile Gly Leu Met Val Gly Gly
            260                 265                 270

Val Val

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Lys Arg Glu Ala Glu Ala
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Lys Arg Glu Ala Glu Ala Glu Ala
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Lys Arg Glu Ala Asp Ala Glu Ala
1               5

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Glu Ala Glu Ala
1

<210> SEQ ID NO 48
<211> LENGTH: 6
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 48

Glu Ala Glu Ala Glu Ala
1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Glu Ala Asp Ala Glu Ala
1               5

<210> SEQ ID NO 50
<211> LENGTH: 636
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
gtcgactgga tccacaagtt tgtacaaaaa agcaggctgg taccaaaaga atgagatttc      60
cttcaatttt tactgcagtt ttattcgcag catcctccgc attagctgct ccagtcaaca     120
ctacaacaga agatgaaacg gcacaaattc cggctgaagc tgtcatcggt tacttagatt     180
tagaagggga tttcgatgtt gctgttttgc catttccaa cagcacaaat aacgggttat      240
tgtttataaa tactactatt gccagcattg ctgctaaaga agaagggta tctttggata      300 aaagagaggc tgaagctgat gctgaattta gacatgattc tggttatgaa gttcatcatc     360
aaaaattggt tttttttgct gaagatgttg gttctaataa aggtgctatt attggtttga     420
tggttggtgg tgttgtcatt gctaagagag aagccgaagc tgaagctgat gctgaattta     480
gacatgattc tggttatgaa gttcatcatc aaaaattggt tttttttgct gaagatgttg     540
gttctaataa aggtgctatt attggtttga tggttggtgg tgttgtcatt gcttaaaccc     600
agctttcttg tacaaagtgg tgcggccgca ctcgag                              636

<210> SEQ ID NO 51
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Asp Ala Glu Phe Arg His Asp
                85                  90                  95

Ser Gly Tyr Glu Val His His Gln Lys Leu Val Phe Phe Ala Glu Asp
            100                 105                 110

Val Gly Ser Asn Lys Gly Ala Ile Ile Gly Leu Met Val Gly Gly Val
        115                 120                 125

Val Ile Ala
    130

<210> SEQ ID NO 52
<211> LENGTH: 636
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
gtcgactgga tccacaagtt tgtacaaaaa agcaggctgg taccaaaaga atgagattcc      60
catctatttt caccgctgtt ttgtttgctg cttcttctgc tttggctgct ccagttaaca    120
ctactactga agatgaaact gctcaaattc agctgaagc tgttattggt tacttggatt     180
tggaaggtga tttcgatgtt gctgttttgc cattctctaa ctctaccaac aatggtttgt    240
tgttcatcaa caccaccatt gcttctattg ctgctaaaga agaaggtgtc tctttggata    300
agagagaagc tgaagcagac gcagaattca gacatgattc tggttatgaa gttcaccacc    360
aaaagttggt tttcttcgct gaagatgttg gttctaacaa gggtgctatt atcggtttga    420
tggttggtgg tgtagttatt gctaaaagag aagccgaagc tgaagctgat gccgaattca    480
gacacgatag tggttacgaa gtacatcatc aaaaattagt cttttttgcc gaagatgtcg    540
gtagtaacaa aggtgcaatc attggtttaa tggtcggtgg tgtcgtaatc gcttaaaccc    600
agctttcttg tacaaagtgg tgcggccgca ctcgag                              636

<210> SEQ ID NO 53
<211> LENGTH: 181
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Leu Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Asp Ala Glu Phe Arg His Asp
                85                  90                  95

Ser Gly Tyr Glu Val His His Gln Lys Leu Val Phe Phe Ala Glu Asp

```
            100                 105                 110
Val Gly Ser Asn Lys Gly Ala Ile Ile Gly Leu Met Val Gly Gly Val
        115                 120                 125

Val Ile Ala Lys Arg Glu Ala Glu Ala Glu Ala Asp Ala Glu Phe Arg
    130                 135                 140

His Asp Ser Gly Tyr Glu Val His His Gln Lys Leu Val Phe Phe Ala
145                 150                 155                 160

Glu Asp Val Gly Ser Asn Lys Gly Ala Ile Ile Gly Leu Met Val Gly
                165                 170                 175

Gly Val Val Ile Ala
            180
```

<210> SEQ ID NO 54
<211> LENGTH: 936
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54

```
gtcgactgga tccacaagtt tgtacaaaaa agcaggctgg taccaaaaga atgagatttc    60
cttcaatttt tactgcagtt ttattcgcag catcctccgc attagctgct ccagtcaaca   120
ctacaacaga agatgaaacg gcacaaattc cggctgaagc tgtcatcggt tacttagatt   180
tagaagggga tttcgatgtt gctgttttgc catttccaa cagcacaaat aacgggttat    240
tgtttataaa tactactatt gccagcattg ctgctaaaga agaagggta tctttggata    300
aaagagaggc tgaagctgat gctgaattta gacatgattc tggttatgaa gttcatcatc   360
aaaaattggt ttttttgct gaagatgttg gttctaataa aggtgctatt attggtttga    420
tggttggtgg tgttgtcatt gctaagagag aagccgaagc tgaagctgat gctgaattta   480
gacatgattc tggttatgaa gttcatcatc aaaaattggt ttttttgct gaagatgttg    540
gttctaataa aggtgctatt attggtttga tggttggtgg tgttgtcatt gctaaaagag   600
aagccgacgc tgaagctgat gctgaattta gacatgattc tggttatgaa gttcatcatc   660
aaaaattggt ttttttgct gaagatgttg gttctaataa aggtgctatt attggtttga    720
tggttggtgg tgttgtcatt gctaaaagag aagccgacgc tgaagctgat gctgaattta   780
gacatgattc tggttatgaa gttcatcatc aaaaattggt ttttttgct gaagatgttg    840
gttctaataa aggtgctatt attggtttga tggttggtgg tgttgtcatt gcttaaaccc   900
agctttcttg tacaaagtgg tgcggccgca ctcgag                             936
```

<210> SEQ ID NO 55
<211> LENGTH: 281
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45
```

```
Asp Val Ala Val Leu Pro Phe Ser Asn Ser Thr Asn Asn Gly Leu Leu
         50                  55                  60

Phe Ile Asn Thr Thr Ile Ala Ser Ile Ala Ala Lys Glu Glu Gly Val
 65                  70                  75                  80

Ser Leu Asp Lys Arg Glu Ala Glu Ala Asp Ala Glu Phe Arg His Asp
                 85                  90                  95

Ser Gly Tyr Glu Val His His Gln Lys Leu Val Phe Phe Ala Glu Asp
                100                 105                 110

Val Gly Ser Asn Lys Gly Ala Ile Ile Gly Leu Met Val Gly Gly Val
            115                 120                 125

Val Ile Ala Lys Arg Glu Ala Glu Ala Glu Ala Asp Ala Glu Phe Arg
        130                 135                 140

His Asp Ser Gly Tyr Glu Val His His Gln Lys Leu Val Phe Phe Ala
145                 150                 155                 160

Glu Asp Val Gly Ser Asn Lys Gly Ala Ile Ile Gly Leu Met Val Gly
                165                 170                 175

Gly Val Val Ile Ala Lys Arg Glu Ala Asp Ala Glu Ala Asp Ala Glu
                180                 185                 190

Phe Arg His Asp Ser Gly Tyr Glu Val His His Gln Lys Leu Val Phe
195                 200                 205

Phe Ala Glu Asp Val Gly Ser Asn Lys Gly Ala Ile Ile Gly Leu Met
210                 215                 220

Val Gly Gly Val Val Ile Ala Lys Arg Glu Ala Asp Ala Glu Ala Asp
225                 230                 235                 240

Ala Glu Phe Arg His Asp Ser Gly Tyr Glu Val His His Gln Lys Leu
                245                 250                 255

Val Phe Phe Ala Glu Asp Val Gly Ser Asn Lys Gly Ala Ile Ile Gly
            260                 265                 270

Leu Met Val Gly Gly Val Val Ile Ala
        275                 280

<210> SEQ ID NO 56
<211> LENGTH: 1236
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
gtcgactgga tccacaagtt tgtacaaaaa agcaggctgg taccaaaaga atgagattcc      60
catctatttt caccgctgtt ttgtttgctg cttcttctgc tttggctgct ccagttaaca     120
ctactactga agatgaaact gctcaaattc agctgaagc tgttattggt tacttggatt     180
tggaaggtga tttcgatgtt gctgttttgc cattctctaa ctctaccaac aatggtttgt     240
tgttcatcaa caccaccatt gcttctattg ctgctaaaga agaaggtgtc tctttggata     300
agagagaagc tgaagcagac gcagaattca gacatgattc tggttatgaa gttcaccacc     360
aaaaagttgg ttttcttcgct gaagatgttg gttctaacaa gggtgctatt atcggtttga     420
tggttggtgg tgtagttatt gctaaaagag aagccgaagc tgaagctgat gccgaattca     480
gacacgatag tggttacgaa gtacatcatc aaaaattagt cttttttgcc gaagatgtcg     540
gtagtaacaa aggtgcaatc attggttaa tggtcggtgg tgtcgtaata gccaagagag     600
aagcagacgc cgaagccgat gcagaattca gacacgactc cggttacgaa gtccatcacc     660
```

```
aaaagttggt attctttgcc gaagatgtcg gttcaaacaa gggtgccata ataggtttaa    720
tggttggtgg tgtcgttatc gcaaaaagag aagctgacgc agaagcagac gccgaattca    780
gacacgattc aggttacgaa gttcaccatc aaaaattggt attttcgca gaagatgttg    840 gttccaacaa aggtgccatt attggtttga tggttggtgg tgtcgtcatt gccaagagag    900
aagctgaagc tgaagccgac gcagaattca gacacgacag tggttatgaa gtccaccatc    960
aaaagttggt cttttttgct gaagatgttg gttctaacaa aggtgcaatc ataggtttga   1020
tggttggtgg tgtagtcata gcaaaaagag aagcagacgc tgaagcagat gccgaattca   1080
gacatgacag tggttatgaa gttcatcacc aaaaattagt attcttcgct gaagatgtag   1140
gtagtaacaa aggtgccata atcggtttga tggtcggtgg tgtcgttata gcttaaaccc   1200
agctttcttg tacaaagtgg tgcggccgca ctcgag                              1236
```

<210> SEQ ID NO 57
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Leu Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Lys Glu Glu Gly Val
65                  70                  75                  80

Ser Leu Asp Lys Arg Glu Ala Glu Ala Asp Ala Glu Phe Arg His Asp
                85                  90                  95

Ser Gly Tyr Glu Val His His Gln Lys Leu Val Phe Phe Ala Glu Asp
                100                 105                 110

Val Gly Ser Asn Lys Gly Ala Ile Ile Gly Leu Met Val Gly Gly Val
            115                 120                 125

Val Ile Ala Lys Arg Glu Ala Glu Ala Glu Ala Asp Ala Glu Phe Arg
        130                 135                 140

His Asp Ser Gly Tyr Glu Val His His Gln Lys Leu Val Phe Phe Ala
145                 150                 155                 160

Glu Asp Val Gly Ser Asn Lys Gly Ala Ile Ile Gly Leu Met Val Gly
                165                 170                 175

Gly Val Val Ile Ala Lys Arg Glu Ala Asp Ala Glu Ala Asp Ala Glu
            180                 185                 190

Phe Arg His Asp Ser Gly Tyr Glu Val His His Gln Lys Leu Val Phe
        195                 200                 205

Phe Ala Glu Asp Val Gly Ser Asn Lys Gly Ala Ile Ile Gly Leu Met
    210                 215                 220

Val Gly Gly Val Val Ile Ala Lys Arg Glu Ala Asp Ala Glu Ala Asp
225                 230                 235                 240

Ala Glu Phe Arg His Asp Ser Gly Tyr Glu Val His His Gln Lys Leu
                245                 250                 255
```

Val Phe Phe Ala Glu Asp Val Gly Ser Asn Lys Gly Ala Ile Ile Gly
                260                 265                 270

Leu Met Val Gly Gly Val Val Ile Ala Lys Arg Glu Ala Glu Ala Glu
            275                 280                 285

Ala Asp Ala Glu Phe Arg His Asp Ser Gly Tyr Glu Val His His Gln
        290                 295                 300

Lys Leu Val Phe Phe Ala Glu Asp Val Gly Ser Asn Lys Gly Ala Ile
305                 310                 315                 320

Ile Gly Leu Met Val Gly Gly Val Val Ile Ala Lys Arg Glu Ala Asp
                325                 330                 335

Ala Glu Ala Asp Ala Glu Phe Arg His Asp Ser Gly Tyr Glu Val His
            340                 345                 350

His Gln Lys Leu Val Phe Phe Ala Glu Asp Val Gly Ser Asn Lys Gly
        355                 360                 365

Ala Ile Ile Gly Leu Met Val Gly Gly Val Val Ile Ala
    370                 375                 380

<210> SEQ ID NO 58
<211> LENGTH: 1538
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
gtcgactgga tccacaagtt tgtacaaaaa agcaggctac ggtacctaca aaatgagatt      60
cccatctatt ttcaccgctg ttttgtttgc tgcttcttct gctttggctg ctccagttaa    120
cactactact gaagatgaaa ctgctcaaat tccagctgaa gctgttattg gttacttgga    180
tttggaaggt gatttcgatg ttgctgtttt gccattctct aactctacca acaatggttt    240
gttgttcatc aacaccacca ttgcttctat tgctgctaaa gaagaaggtg tctctttgga    300
taagagagaa gctgaagcag acgcagaatt cagacatgat tctggttatg aagttcacca    360
ccaaaagttg gtttttcttcg ctgaagatgt tggttctaac aagggtgcta ttatcggttt    420
gatggttggt ggtgtagtta ttgctaaaag agaagccgaa gctgaagctg atgccgaatt    480
cagacacgat agtggttacg aagtacatca tcaaaaatta gtcttttttg ccgaagatgt    540
cggtagtaac aaaggtgcaa tcattggttt aatggtcggt ggtgtcgtaa tagccaagag    600
agaagcagac gccgaagccg atgcagaatt cagacacgac tccggttacg aagtccatca    660
ccaaaagttg gtattctttg ccgaagatgt cggttcaaac aagggtgcca ataggtttt    720 aatggttggt ggtgtcgtta tcgcaaaaag agaagctgac gcagaagcag acgccgaatt    780
cagacacgat tcaggttacg aagttcacca tcaaaaattg gtattttcg cagaagatgt    840 tggttccaac aaaggtgcca ttattggttt gatggttggt ggtgtcgtca ttgccaagag    900
agaagctgaa gctgaagccg acgcagaatt cagacacgac agtggttatg aagtccacca    960
tcaaaagttg gtcttttttg ctgaagatgt tggttctaac aaaggtgcaa tcataggttt   1020
gatggttggt ggtgtagtca tagcaaaaag agaagcagac gctgaagcag atgccgaatt   1080
cagacatgac agtggttatg aagttcatca ccaaaaatta gtattcttcg ctgaagatgt   1140
aggtagtaac aaaggtgcca taatcggttt gatggtcggt ggtgtcgtta tcgctaagag   1200
agaagcagac gctgaagctg acgcagaatt cagacatgac tcaggttacg aagtacacca   1260
tcaaaagtta gtattcttcg ccgaagatgt aggttcaaac aaaggtgcta tcatcggttt   1320

```
aatggttggt ggtgtcgtaa ttgctaaaag agaagctgaa gccgaagcag atgcagaatt   1380
cagacatgat tcaggttacg aagtccatca ccaaaaattg gtcttttcg ctgaagatgt    1440 cggttcaaac aagggtgcaa ttattggttt gatggtcggt ggtgtagtaa ttgcctaaac   1500
ccagctttct tgtacaaagt ggtgcggccg cactcgag                           1538
```

<210> SEQ ID NO 59
<211> LENGTH: 481
<212> TYPE: PRT
<213> ORGANISM: Artificial Sequence
<220> FEATURE:
<223> OTHER INFORMATION: Description of Artificial Sequence: Synthetic
   polypeptide

<400> SEQUENCE: 59

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Asp Ala Glu Phe Arg His Asp
                85                  90                  95

Ser Gly Tyr Glu Val His His Gln Lys Leu Val Phe Phe Ala Glu Asp
            100                 105                 110

Val Gly Ser Asn Lys Gly Ala Ile Ile Gly Leu Met Val Gly Gly Val
        115                 120                 125

Val Ile Ala Lys Arg Glu Ala Glu Ala Asp Ala Glu Phe Arg
    130                 135                 140

His Asp Ser Gly Tyr Glu Val His His Gln Lys Leu Val Phe Phe Ala
145                 150                 155                 160

Glu Asp Val Gly Ser Asn Lys Gly Ala Ile Ile Gly Leu Met Val Gly
                165                 170                 175

Gly Val Val Ile Ala Lys Arg Glu Ala Asp Ala Glu Ala Asp Ala Glu
            180                 185                 190

Phe Arg His Asp Ser Gly Tyr Glu Val His His Gln Lys Leu Val Phe
        195                 200                 205

Phe Ala Glu Asp Val Gly Ser Asn Lys Gly Ala Ile Ile Gly Leu Met
    210                 215                 220

Val Gly Gly Val Val Ile Ala Lys Arg Glu Ala Asp Ala Glu Ala Asp
225                 230                 235                 240

Ala Glu Phe Arg His Asp Ser Gly Tyr Glu Val His His Gln Lys Leu
                245                 250                 255

Val Phe Phe Ala Glu Asp Val Gly Ser Asn Lys Gly Ala Ile Ile Gly
            260                 265                 270

Leu Met Val Gly Gly Val Val Ile Ala Lys Arg Glu Ala Glu Ala Glu
        275                 280                 285

Ala Asp Ala Glu Phe Arg His Asp Ser Gly Tyr Glu Val His His Gln
    290                 295                 300

Lys Leu Val Phe Phe Ala Glu Asp Val Gly Ser Asn Lys Gly Ala Ile
305                 310                 315                 320
```

```
Ile Gly Leu Met Val Gly Gly Val Val Ile Ala Lys Arg Glu Ala Asp
            325                 330                 335

Ala Glu Ala Asp Ala Glu Phe Arg His Asp Ser Gly Tyr Glu Val His
        340                 345                 350

His Gln Lys Leu Val Phe Phe Ala Glu Asp Val Gly Ser Asn Lys Gly
    355                 360                 365

Ala Ile Ile Gly Leu Met Val Gly Gly Val Val Ile Ala Lys Arg Glu
370                 375                 380

Ala Asp Ala Glu Ala Asp Ala Glu Phe Arg His Asp Ser Gly Tyr Glu
385                 390                 395                 400

Val His His Gln Lys Leu Val Phe Phe Ala Glu Asp Val Gly Ser Asn
                405                 410                 415

Lys Gly Ala Ile Ile Gly Leu Met Val Gly Gly Val Val Ile Ala Lys
            420                 425                 430

Arg Glu Ala Glu Ala Glu Ala Asp Ala Glu Phe Arg His Asp Ser Gly
        435                 440                 445

Tyr Glu Val His His Gln Lys Leu Val Phe Phe Ala Glu Asp Val Gly
    450                 455                 460

Ser Asn Lys Gly Ala Ile Ile Gly Leu Met Val Gly Gly Val Val Ile
465                 470                 475                 480

Ala
```

<210> SEQ ID NO 60
<211> LENGTH: 912
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 60

```
gtcgactgga tccacaagtt tgtacaaaaa agcaggctgg taccaaaaga atgagattcc    60
catctatttt caccgctgtt tgtttgctg cttcttctgc tttggctgct ccagttaaca   120
ctactactga agatgaaact gctcaaattc agctgaagc tgttattggt tacttggatt   180
tggaaggtga tttcgatgtt gctgttttgc cattctctaa ctctaccaac aatggtttgt   240
tgttcatcaa caccaccatt gcttctattg ctgctaaaga agaaggtgtc tctttggata   300
agagagaagc tgaagcagac gcagaattca gacatgattc tggttatgaa gttcaccacc   360
aaaagttggt tttcttcgct gaagatgttg gttctaacaa gggtgctatt atcggtttga   420
tggttggtgg tgtagtaaaa agagaagccg aagctgaagc tgatgccgaa ttcagacacg   480
atagtggtta cgaagtacat catcaaaaat tagtcttttt tgccgaagat gtcggtagta   540
acaaaggtgc aatcattggt ttaatggtcg gtggtgtcgt taagagagaa gcagacgccg   600
aagccgatgc agaattcaga cacgactccg gttacgaagt ccatcaccaa agttggtat   660
tctttgccga agatgtcggt tcaaacaagg gtgccataat aggtttaatg gttggtggtg   720
tcgtcaaaag agaagctgac gctgaagcag acgccgaatt cagacacgac tcaggttatg   780
aagtacacca tcaaaaattg gtattttttcg cagaagatgt tggttccaac aaaggtgcca   840
ttattggttt gatggttggt ggtgtcgttt aaacccagct tcttgtaca aagtggtgcg   900
gccgcactcg ag                                                       912
```

<210> SEQ ID NO 61
<211> LENGTH: 273
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 61

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Asp Ala Glu Phe Arg His Asp
                85                  90                  95

Ser Gly Tyr Glu Val His His Gln Lys Leu Val Phe Phe Ala Glu Asp
            100                 105                 110

Val Gly Ser Asn Lys Gly Ala Ile Ile Gly Leu Met Val Gly Gly Val
        115                 120                 125

Val Lys Arg Glu Ala Glu Ala Asp Ala Glu Phe Arg His Asp
130                 135                 140

Ser Gly Tyr Glu Val His His Gln Lys Leu Val Phe Phe Ala Glu Asp
145                 150                 155                 160

Val Gly Ser Asn Lys Gly Ala Ile Ile Gly Leu Met Val Gly Gly Val
            165                 170                 175

Val Lys Arg Glu Ala Asp Ala Glu Ala Asp Ala Glu Phe Arg His Asp
        180                 185                 190

Ser Gly Tyr Glu Val His His Gln Lys Leu Val Phe Phe Ala Glu Asp
            195                 200                 205

Val Gly Ser Asn Lys Gly Ala Ile Ile Gly Leu Met Val Gly Gly Val
        210                 215                 220

Val Lys Arg Glu Ala Asp Ala Glu Ala Asp Ala Glu Phe Arg His Asp
225                 230                 235                 240

Ser Gly Tyr Glu Val His His Gln Lys Leu Val Phe Phe Ala Glu Asp
                245                 250                 255

Val Gly Ser Asn Lys Gly Ala Ile Ile Gly Leu Met Val Gly Gly Val
            260                 265                 270

Val

<210> SEQ ID NO 62
<211> LENGTH: 1200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
gtcgactgga tccacaagtt tgtacaaaaa agcaggctgg taccaaaaga atgagattcc      60
catctatttt caccgctgtt ttgtttgctg cttcttctgc tttggctgct ccagttaaca     120
ctactactga agatgaaact gctcaaattc cagctgaagc tgttattggt tacttggatt     180
tggaaggtga tttcgatgtt gctgttttgc cattctctaa ctctaccaac aatggtttgt     240

```
tgttcatcaa caccaccatt gcttctattg ctgctaaaga agaaggtgtc tctttggata    300
agagagaagc tgaagcagac gcagaattca gacatgattc tggttatgaa gttcaccacc    360
aaaagttggt tttcttcgct gaagatgttg ttctaacaa gggtgctatt atcggtttga    420
tggttggtgg tgtagtaaaa agagaagccg aagctgaagc tgatgccgaa ttcagacacg    480
atagtggtta cgaagtacat catcaaaaat tagtcttttt tgccgaagat gtcggtagta    540
acaaaggtgc aatcattggt ttaatggtcg gtggtgtcgt taagagagaa gcagacgccg    600
aagccgatgc agaattcaga cacgactccg gttacgaagt ccatcaccaa aagttggtat    660
tctttgccga gatgtcggt tcaaacaagg gtgccataat aggtttaatg gttggtggtg    720
tcgtcaaaag agaagctgac gctgaagcag acgccgaatt cagacacgac tcaggttatg    780
aagtacacca tcaaaaattg gtattttcg cagaagatgt tggttccaac aaaggtgcca    840
ttattggttt gatggttggt ggtgtcgtca agagagaagc cgaagccgaa gctgacgcag    900
aattcagaca tgacagtggt tacgaagtcc accatcaaaa gttggtcttt tttgctgaag    960
atgttggttc taacaaaggt gcaatcatag gtttgatggt tggtggtgta gttaagagag   1020
aagctgacgc tgaagctgat gcagaattca gacatgattc aggttacgaa gtccatcatc   1080
aaaaattggt tttcttcgcc gaagatgtag gttcaaacaa aggtgctatc atcggtttaa   1140
tggttggtgg tgtcgtttga acccagcttt cttgtacaaa gtggtgcggc cgcactcgag   1200
```

<210> SEQ ID NO 63  
<211> LENGTH: 369  
<212> TYPE: PRT  
<213> ORGANISM: Artificial Sequence  
<220> FEATURE:  
<223> OTHER INFORMATION: Description of Artificial Sequence: Synthetic polypeptide

<400> SEQUENCE: 63

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Asp Ala Glu Phe Arg His Asp
                85                  90                  95

Ser Gly Tyr Glu Val His His Gln Lys Leu Val Phe Phe Ala Glu Asp
            100                 105                 110

Val Gly Ser Asn Lys Gly Ala Ile Ile Gly Leu Met Val Gly Gly Val
        115                 120                 125

Val Lys Arg Glu Ala Glu Ala Glu Ala Asp Ala Glu Phe Arg His Asp
    130                 135                 140

Ser Gly Tyr Glu Val His His Gln Lys Leu Val Phe Phe Ala Glu Asp
145                 150                 155                 160

Val Gly Ser Asn Lys Gly Ala Ile Ile Gly Leu Met Val Gly Gly Val
                165                 170                 175

Val Lys Arg Glu Ala Asp Ala Glu Ala Asp Ala Glu Phe Arg His Asp
            180                 185                 190

-continued

```
Ser Gly Tyr Glu Val His His Gln Lys Leu Val Phe Phe Ala Glu Asp
            195                 200                 205

Val Gly Ser Asn Lys Gly Ala Ile Ile Gly Leu Met Val Gly Gly Val
        210                 215                 220

Val Lys Arg Glu Ala Asp Ala Glu Ala Asp Ala Glu Phe Arg His Asp
225                 230                 235                 240

Ser Gly Tyr Glu Val His His Gln Lys Leu Val Phe Phe Ala Glu Asp
                245                 250                 255

Val Gly Ser Asn Lys Gly Ala Ile Ile Gly Leu Met Val Gly Gly Val
            260                 265                 270

Val Lys Arg Glu Ala Glu Ala Glu Ala Asp Ala Glu Phe Arg His Asp
        275                 280                 285

Ser Gly Tyr Glu Val His His Gln Lys Leu Val Phe Phe Ala Glu Asp
    290                 295                 300

Val Gly Ser Asn Lys Gly Ala Ile Ile Gly Leu Met Val Gly Gly Val
305                 310                 315                 320

Val Lys Arg Glu Ala Asp Ala Glu Ala Asp Ala Glu Phe Arg His Asp
                325                 330                 335

Ser Gly Tyr Glu Val His His Gln Lys Leu Val Phe Phe Ala Glu Asp
            340                 345                 350

Val Gly Ser Asn Lys Gly Ala Ile Ile Gly Leu Met Val Gly Gly Val
        355                 360                 365

Val
```

<210> SEQ ID NO 64
<211> LENGTH: 936
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 64

```
gtcgactgga tccacaagtt tgtacaaaaa agcaggctgg taccaaaaga atgagattcc    60
catctatttt caccgctgtt ttgtttgctg cttcttctgc tttggctgct ccagttaaca   120
ctactactga agatgaaact gctcaaattc agctgaagc tgttattggt tacttggatt   180
tggaaggtga tttcgatgtt gctgttttgc cattctctaa ctctaccaac aatggtttgt   240
tgttcatcaa caccaccatt gcttctattg ctgctaaaga agaaggtgtc tctttggata   300
agagagaagc tgaagcagac gcagaattta gaagagattc tggttacgaa gttcaccacc   360
aaaagttggt ttttttcgct gaagatgtcg gttctaacaa gggtgctatt attggtttga   420
tggttggtgg tgtcgttatt gctaaaagag aagccgaagc tgaagctgat gccgaattca   480
gaagagactc aggttacgaa gtacatcatc aaaaattagt attctttgcc gaagatgttg   540
gtagtaacaa aggtgcaatc atcggtttaa tggtcggtgg tgtagtaata gccaagagag   600
aagcagacgc cgaagccgac gcagaattca agagagattc aggttacgaa gtccatcacc   660
aaaagttagt tttcttcgca gaagatgtcg gttcaaacaa aggtgccata ataggtttaa   720
tggttggtgg tgtagttatc gctaagagag aagctgacgc tgaagcagat gcagaattca   780
gaagagactc cggttacgaa gttcaccatc aaaaattagt cttttcgca gaagatgttg   840
gtagtaacaa gggtgctata ataggtttga tggtcggtgg tgtcgtcata gcttaaaccc   900
agctttcttg tacaaagtgg tgcggccgca ctcgag                              936
```

<210> SEQ ID NO 65
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Asp Ala Glu Phe Arg Arg Asp
                85                  90                  95

Ser Gly Tyr Glu Val His His Gln Lys Leu Val Phe Phe Ala Glu Asp
            100                 105                 110

Val Gly Ser Asn Lys Gly Ala Ile Ile Gly Leu Met Val Gly Gly Val
        115                 120                 125

Val Ile Ala Lys Arg Glu Ala Glu Ala Glu Asp Ala Glu Phe Arg
    130                 135                 140

Arg Asp Ser Gly Tyr Glu Val His His Gln Lys Leu Val Phe Phe Ala
145                 150                 155                 160

Glu Asp Val Gly Ser Asn Lys Gly Ala Ile Ile Gly Leu Met Val Gly
                165                 170                 175

Gly Val Val Ile Ala Lys Arg Glu Ala Asp Ala Glu Ala Asp Ala Glu
            180                 185                 190

Phe Arg Arg Asp Ser Gly Tyr Glu Val His His Gln Lys Leu Val Phe
        195                 200                 205

Phe Ala Glu Asp Val Gly Ser Asn Lys Gly Ala Ile Ile Gly Leu Met
    210                 215                 220

Val Gly Gly Val Val Ile Ala Lys Arg Glu Ala Asp Ala Glu Ala Asp
225                 230                 235                 240

Ala Glu Phe Arg Arg Asp Ser Gly Tyr Glu Val His His Gln Lys Leu
                245                 250                 255

Val Phe Phe Ala Glu Asp Val Gly Ser Asn Lys Gly Ala Ile Ile Gly
            260                 265                 270

Leu Met Val Gly Gly Val Val Ile Ala
        275                 280

<210> SEQ ID NO 66
<211> LENGTH: 936
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
gtcgactgga tccacaagtt tgtacaaaaa agcaggctgg taccaaaaga atgagattcc      60
catctatttt caccgctgtt ttgtttgctg cttcttctgc tttggctgct ccagttaaca     120

```
ctactactga agatgaaact gctcaaattc cagctgaagc tgttattggt tacttggatt      180
tggaaggtga tttcgatgtt gctgttttgc cattctctaa ctctaccaac aatggtttgt      240
tgttcatcaa caccaccatt gcttctattg ctgctaaaga agaaggtgtc tctttggata      300
agagagaagc tgaagcagac gcagaattca gacatgattc tggttatgaa gttcaccacc      360
aaaagttggt ttttgaagcc gaagatgttg gttctaacaa gggtgctatt atcggtttga      420
tggttggtgg tgtagttatt gctaaaagag aagccgaagc tgaagctgat gccgaattca      480
gacacgatag tggttacgaa gtacatcatc aaaaattagt attcgaagct gaagatgtcg      540
gtagtaacaa aggtgcaatc attggtttaa tggtcggtgg tgtcgtaata gccaagagag      600
aagcagacgc cgaagccgat gcagaattca gacacgactc cggttacgaa gtccatcacc      660
aaaagttagt ctttgaagct gaagatgtcg gttcaaacaa aggtgccata ataggtttaa      720
tggttggtgg tgtcgttatc gcaaaaagag aagctgacgc agaagcagac gccgaattca      780
gacacgattc aggttacgaa gttcaccatc aaaaattggt ctttgaagct gaagatgttg      840
gtagtaacaa gggtgccata ataggtttga tggtcggtgg tgtagtcata gcttaaaccc      900
agctttcttg tacaaagtgg tgcggccgca ctcgag                               936
```

<210> SEQ ID NO 67
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Leu Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Asp Ala Glu Phe Arg His Asp
                85                  90                  95

Ser Gly Tyr Glu Val His His Gln Lys Leu Val Phe Glu Ala Glu Asp
            100                 105                 110

Val Gly Ser Asn Lys Gly Ala Ile Ile Gly Leu Met Val Gly Gly Val
        115                 120                 125

Val Ile Ala Lys Arg Glu Ala Glu Ala Glu Asp Ala Glu Phe Arg
    130                 135                 140

His Asp Ser Gly Tyr Glu Val His His Gln Lys Leu Val Phe Glu Ala
145                 150                 155                 160

Glu Asp Val Gly Ser Asn Lys Gly Ala Ile Ile Gly Leu Met Val Gly
                165                 170                 175

Gly Val Val Ile Ala Lys Arg Glu Ala Asp Ala Glu Ala Asp Ala Glu
            180                 185                 190

Phe Arg His Asp Ser Gly Tyr Glu Val His His Gln Lys Leu Val Phe
        195                 200                 205

Glu Ala Glu Asp Val Gly Ser Asn Lys Gly Ala Ile Ile Gly Leu Met
```

Val Gly Gly Val Val Ile Ala Lys Arg Glu Ala Asp Ala Glu Ala Asp
225                 230                 235                 240

Ala Glu Phe Arg His Asp Ser Gly Tyr Glu Val His His Gln Lys Leu
            245                 250                 255

Val Phe Glu Ala Glu Asp Val Gly Ser Asn Lys Gly Ala Ile Ile Gly
        260                 265                 270

Leu Met Val Gly Gly Val Val Ile Ala
        275                 280

<210> SEQ ID NO 68
<211> LENGTH: 936
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
gtcgactgga tccacaagtt tgtacaaaaa agcaggctgg taccaaaaga atgagattcc    60
catctatttt caccgctgtt ttgtttgctg cttcttctgc tttggctgct ccagttaaca   120
ctactactga agatgaaact gctcaaattc agctgaagc tgttattggt tacttggatt    180
tggaaggtga tttcgatgtt gctgttttgc cattctctaa ctctaccaac aatggtttgt   240
tgttcatcaa caccaccatt gcttctattg ctgctaaaga agaaggtgtc tctttggata   300
agagagaagc tgaagcagac gcagaattca gacatgattc tggttatgaa gttcaccacc   360
aaaagttggt tttcttcggt gaagatgttg gttctaacaa gggtgctatt atcggtttga   420
tggttggtgg tgtagttatt gctaaaagag aagccgaagc tgaagctgat gccgaattca   480
gacacgatag tggttacgaa gtacatcatc aaaaattagt cttttttggt gaagatgtcg   540
gtagtaacaa aggtgccata attggtttaa tggtcggtgg tgtcgtaata gccaagagag   600
aagcagacgc cgaagccgat gcagaattca gacacgactc cggttacgaa gtccatcacc   660
aaaagttggt ttttttggt gaagatgtcg gttccaacaa gggtgcaatc ataggtttaa    720
tggttggtgg tgtcgttatc gcaaaaagag aagctgacgc agaagcagac gccgaattca   780
gacacgattc aggttacgaa gttcaccatc aaaaattggt attctttggt gaagatgtag   840
gttcaaacaa aggtgccatc attggtttga tggttggtgg tgtcgtaatt gcctaaaccc   900
agctttcttg tacaaagtgg tgcggccgca ctcgag                            936

<210> SEQ ID NO 69
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
 65                  70                  75                  80

Ser Leu Asp Lys Arg Glu Ala Glu Ala Asp Ala Glu Phe Arg His Asp
             85                  90                  95

Ser Gly Tyr Glu Val His His Gln Lys Leu Val Phe Phe Gly Glu Asp
         100                 105                 110

Val Gly Ser Asn Lys Gly Ala Ile Ile Gly Leu Met Val Gly Gly Val
     115                 120                 125

Val Ile Ala Lys Arg Glu Ala Glu Ala Glu Ala Asp Ala Glu Phe Arg
130                 135                 140

His Asp Ser Gly Tyr Glu Val His His Gln Lys Leu Val Phe Phe Gly
145                 150                 155                 160

Glu Asp Val Gly Ser Asn Lys Gly Ala Ile Ile Gly Leu Met Val Gly
                165                 170                 175

Gly Val Val Ile Ala Lys Arg Glu Ala Asp Ala Glu Ala Asp Ala Glu
            180                 185                 190

Phe Arg His Asp Ser Gly Tyr Glu Val His His Gln Lys Leu Val Phe
        195                 200                 205

Phe Gly Glu Asp Val Gly Ser Asn Lys Gly Ala Ile Ile Gly Leu Met
    210                 215                 220

Val Gly Gly Val Val Ile Ala Lys Arg Glu Ala Asp Ala Glu Ala Asp
225                 230                 235                 240

Ala Glu Phe Arg His Asp Ser Gly Tyr Glu Val His His Gln Lys Leu
                245                 250                 255

Val Phe Phe Gly Glu Asp Val Gly Ser Asn Lys Gly Ala Ile Ile Gly
            260                 265                 270

Leu Met Val Gly Gly Val Val Ile Ala
        275                 280

<210> SEQ ID NO 70
<211> LENGTH: 936
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
gtcgactgga tccacaagtt tgtacaaaaa agcaggctgg taccaaaaga atgagattcc      60
catctatttt caccgctgtt ttgtttgctg cttcttctgc tttggctgct ccagttaaca     120
ctactactga agatgaaact gctcaaattc agctgaagc tgttattggt tacttggatt     180
tggaaggtga tttcgatgtt gctgttttgc cattctctaa ctctaccaac aatggttttg     240
tgttcatcaa caccaccatt gcttctattg ctgctaaaga agaaggtgtc tctttggata     300
agagagaagc tgaagcagac gcagaattca gacatgattc tggttatgaa gttcaccacc     360
aaaagttggt tttcttcgct caagatgttg gttctaacaa gggtgctatt atcggtttga     420
tggttggtgg tgtagttatt gctaaaagag aagccgaagc tgaagctgat gccgaattca     480
gacacgatag tggttacgaa gtacatcatc aaaaattagt cttttttcgcc caagacgtcg     540 gtagtaacaa aggtgcaatc attggtttaa tggtcggtgg tgtcgtaata gccaagagag     600
aagcagacgc cgaagccgat gcagaattca gacacgactc cggttacgaa gtccatcacc     660
aaaagttggt atttttgcc caagacgtag gttcaaacaa gggtgccata ataggtttaa     720
tggttggtgg tgtcgttatc gcaaaaagag aagctgacgc agaagcagac gccgaattca     780

```
gacacgattc aggttacgaa gttcaccatc aaaaattggt attctttgcc caagatgttg    840
gttccaacaa aggtgccatt attggtttga tggttggtgg tgtcgtcata gcttaaaccc    900
agctttcttg tacaaagtgg tgcggccgca ctcgag                              936
```

<210> SEQ ID NO 71
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Ala Glu Phe Arg His Asp
                85                  90                  95

Ser Gly Tyr Glu Val His His Gln Lys Leu Val Phe Phe Ala Gln Asp
            100                 105                 110

Val Gly Ser Asn Lys Gly Ala Ile Ile Gly Leu Met Val Gly Gly Val
        115                 120                 125

Val Ile Ala Lys Arg Glu Ala Glu Ala Glu Asp Ala Glu Phe Arg
    130                 135                 140

His Asp Ser Gly Tyr Glu Val His His Gln Lys Leu Val Phe Phe Ala
145                 150                 155                 160

Gln Asp Val Gly Ser Asn Lys Gly Ala Ile Ile Gly Leu Met Val Gly
                165                 170                 175

Gly Val Val Ile Ala Lys Arg Glu Ala Asp Ala Glu Ala Asp Ala Glu
            180                 185                 190

Phe Arg His Asp Ser Gly Tyr Glu Val His His Gln Lys Leu Val Phe
        195                 200                 205

Phe Ala Gln Asp Val Gly Ser Asn Lys Gly Ala Ile Ile Gly Leu Met
    210                 215                 220

Val Gly Gly Val Val Ile Ala Lys Arg Glu Ala Asp Ala Glu Ala Asp
225                 230                 235                 240

Ala Glu Phe Arg His Asp Ser Gly Tyr Glu Val His His Gln Lys Leu
                245                 250                 255

Val Phe Phe Ala Gln Asp Val Gly Ser Asn Lys Gly Ala Ile Ile Gly
            260                 265                 270

Leu Met Val Gly Gly Val Val Ile Ala
        275                 280
```

<210> SEQ ID NO 72
<211> LENGTH: 936
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72

```
gtcgactgga tccacaagtt tgtacaaaaa agcaggctgg taccaaaaga atgagattcc      60
catctatttt caccgctgtt ttgtttgctg cttcttctgc tttggctgct ccagttaaca     120
ctactactga agatgaaact gctcaaattc cagctgaagc tgttattggt tacttggatt     180
tggaaggtga tttcgatgtt gctgtttttgc cattctctaa ctctaccaac aatggtttgt    240
tgttcatcaa caccaccatt gcttctattg ctgctaaaga agaaggtgtc tctttggata     300
agagagaagc tgaagcagac gcagaattca gacatgattc tggttatgaa gttcaccacc     360
aaaagttggt tttcttcgct aaagatgtcg gttctaacaa gggtgctatt atcggtttga     420
tggttggtgg tgtagttatt gctaaaagag aagccgaagc tgaagctgat gccgaattca     480
gacacgatag tggttacgaa gtacatcatc aaaaattagt cttttttcgcc aaggacgtcg    540
gtagtaacaa aggtgcaatc attggtttaa tggtcggtgg tgtcgtaata gccaagagag     600
aagcagacgc cgaagccgat gcagaattca gacacgactc cggttacgaa gtccatcacc     660
aaaagttggt atttttttgcc aaggacgttg gttcaaacaa gggtgccata ataggtttaa    720
tggttggtgg tgtcgttatc gcaaaaagag aagctgacgc agaagcagac gccgaattca     780
gacacgattc aggttacgaa gttcaccatc aaaaattggt attctttgcc aaagatgtag     840
gtagtaacaa gggtgccata attggtttga tggtcggtgg tgtagtcata gcttaaaccc     900
agctttcttg tacaaagtgg tgcggccgca ctcgag                               936
```

<210> SEQ ID NO 73
<211> LENGTH: 281
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 73

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Asp Ala Glu Phe Arg His Asp
                85                  90                  95

Ser Gly Tyr Glu Val His His Gln Lys Leu Val Phe Phe Ala Lys Asp
            100                 105                 110

Val Gly Ser Asn Lys Gly Ala Ile Ile Gly Leu Met Val Gly Gly Val
        115                 120                 125

Val Ile Ala Lys Arg Glu Ala Glu Ala Glu Ala Asp Ala Glu Phe Arg
    130                 135                 140

His Asp Ser Gly Tyr Glu Val His His Gln Lys Leu Val Phe Phe Ala
145                 150                 155                 160

Lys Asp Val Gly Ser Asn Lys Gly Ala Ile Ile Gly Leu Met Val Gly
                165                 170                 175
```

Gly Val Val Ile Ala Lys Arg Glu Ala Asp Ala Glu Ala Asp Ala Glu
            180                 185                 190

Phe Arg His Asp Ser Gly Tyr Glu Val His His Gln Lys Leu Val Phe
        195                 200                 205

Phe Ala Lys Asp Val Gly Ser Asn Lys Gly Ala Ile Ile Gly Leu Met
    210                 215                 220

Val Gly Gly Val Val Ile Ala Lys Arg Glu Ala Asp Ala Glu Ala Asp
225                 230                 235                 240

Ala Glu Phe Arg His Asp Ser Gly Tyr Glu Val His His Gln Lys Leu
                245                 250                 255

Val Phe Phe Ala Lys Asp Val Gly Ser Asn Lys Gly Ala Ile Ile Gly
            260                 265                 270

Leu Met Val Gly Gly Val Val Ile Ala
        275                 280

<210> SEQ ID NO 74
<211> LENGTH: 936
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
gtcgactgga tccacaagtt tgtacaaaaa agcaggctgg taccaaaaga atgagattcc     60
catctatttt caccgctgtt ttgtttgctg cttcttctgc tttggctgct ccagttaaca    120
ctactactga agatgaaact gctcaaattc agctgaagc tgttattggt tacttggatt    180
tggaaggtga tttcgatgtt gctgttttgc cattctctaa ctctaccaac aatggtttgt    240
tgttcatcaa caccaccatt gcttctattg ctgctaaaga agaaggtgtc tctttggata    300
agagagaagc tgaagcagac gcagaattca gacatgattc tggttatgaa gttcaccacc    360
aaaagttggt ttttttcgct ggtgatgttg gttctaacaa gggtgctatt attggtttga    420
tggttggtgg tgtcgttatt gctaaaagag aagccgaagc tgaagctgat gccgaattca    480
gacacgatag tggttacgaa gtacatcatc aaaaattagt tttctttgcc ggtgacgtcg    540
gtagtaacaa aggtgcaatc ataggtttaa tggtcggtgg tgtagtcata gccaagagag    600
aagcagacgc gaagccgat gcagaattca gacacgactc cggttacgaa gtccatcacc    660
aaaagttggt attctttgcc ggtgacgtag gttcaaacaa gggtgccata atcggtttaa    720
tggttggtgg tgtagtaatc gcaaaaagag aagctgacgc tgaagcagac gccgaattca    780
gacacgactc aggttatgaa gtacaccatc aaaaattggt cttttttcgcc ggtgatgtag    840
gtagtaacaa gggtgcaatt atcggtttga tggtcggtgg tgtagttatc gcttaaaccc    900
agctttcttg tacaaagtgg tgcggccgca ctcgag                              936

<210> SEQ ID NO 75
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Met Arg Phe Pro Ser Ile Phe Thr Ala Val Leu Phe Ala Ala Ser Ser
1               5                   10                  15

```
Ala Leu Ala Ala Pro Val Asn Thr Thr Thr Glu Asp Glu Thr Ala Gln
             20                  25                  30

Ile Pro Ala Glu Ala Val Ile Gly Tyr Leu Asp Leu Glu Gly Asp Phe
         35                  40                  45

Asp Val Ala Val Leu Pro Phe Ser Asn Ser Thr Asn Asn Gly Leu Leu
     50                  55                  60

Phe Ile Asn Thr Thr Ile Ala Ser Ile Ala Ala Lys Glu Glu Gly Val
 65                  70                  75                  80

Ser Leu Asp Lys Arg Glu Ala Glu Ala Asp Ala Glu Phe Arg His Asp
                 85                  90                  95

Ser Gly Tyr Glu Val His His Gln Lys Leu Val Phe Phe Ala Gly Asp
            100                 105                 110

Val Gly Ser Asn Lys Gly Ala Ile Ile Gly Leu Met Val Gly Gly Val
        115                 120                 125

Val Ile Ala Lys Arg Glu Ala Glu Ala Glu Ala Asp Ala Glu Phe Arg
    130                 135                 140

His Asp Ser Gly Tyr Glu Val His His Gln Lys Leu Val Phe Phe Ala
145                 150                 155                 160

Gly Asp Val Gly Ser Asn Lys Gly Ala Ile Ile Gly Leu Met Val Gly
                165                 170                 175

Gly Val Val Ile Ala Lys Arg Glu Ala Asp Ala Glu Ala Asp Ala Glu
            180                 185                 190

Phe Arg His Asp Ser Gly Tyr Glu Val His His Gln Lys Leu Val Phe
        195                 200                 205

Phe Ala Gly Asp Val Gly Ser Asn Lys Gly Ala Ile Ile Gly Leu Met
    210                 215                 220

Val Gly Gly Val Val Ile Ala Lys Arg Glu Ala Asp Ala Glu Ala Asp
225                 230                 235                 240

Ala Glu Phe Arg His Asp Ser Gly Tyr Glu Val His His Gln Lys Leu
                245                 250                 255

Val Phe Phe Ala Gly Asp Val Gly Ser Asn Lys Gly Ala Ile Ile Gly
            260                 265                 270

Leu Met Val Gly Gly Val Val Ile Ala
        275                 280

<210> SEQ ID NO 76
<211> LENGTH: 936
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
gtcgactgga tccacaagtt tgtacaaaaa agcaggctgg taccaaaaga atgagattcc     60
catctatttt caccgctgtt ttgtttgctg cttcttctgc tttggctgct ccagttaaca    120
ctactactga agatgaaact gctcaaattc cagctgaagc tgttattggt tacttggatt    180
tggaaggtga tttcgatgtt gctgttttgc cattctctaa ctctaccaac aatggtttgt    240
tgttcatcaa caccaccatt gcttctattg ctgctaaaga agaaggtgtc tctttggata    300
agagagaagc tgaagcagac gcagaattca gacatgattc tggttatgaa gttcaccacc    360
aaaagttggt ttttttcgct ggtgatgttg gttctaacaa gggtgctgaa attggtttga    420
tggttggtgg tgtagttatt gctaaaagag aagccgaagc tgaagctgat gccgaattca    480
gacacgatag tggttacgaa gtacatcatc aaaaattagt tttctttgcc ggtgacgtcg    540
```

```
gtagtaacaa aggtgcagaa ataggtttaa tggtcggtgg tgtcgtaata gccaagagag    600
aagcagacgc cgaagccgat gcagaattca gacacgactc cggttacgaa gtccatcacc    660
aaaagttggt attctttgcc ggtgacgtag gttcaaacaa gggtgcagaa atcggtttaa    720
tggttggtgg tgtagtcata gcaaagagag aagctgacgc tgaagcagac gccgaattca    780
gacacgactc aggttatgaa gtacaccatc aaaaattggt cttttcgcc ggtgatgtag     840 gtagtaacaa gggtgccgaa atcggtttga tggtcggtgg tgtcgttatc gcttaaaccc    900
agctttcttg tacaaagtgg tgcggccgca ctcgag                              936
```

<210> SEQ ID NO 77
<211> LENGTH: 281
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 77

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Leu Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Asp Ala Glu Phe Arg His Asp
                85                  90                  95

Ser Gly Tyr Glu Val His His Gln Lys Leu Val Phe Phe Ala Gly Asp
            100                 105                 110

Val Gly Ser Asn Lys Gly Ala Glu Ile Gly Leu Met Val Gly Gly Val
        115                 120                 125

Val Ile Ala Lys Arg Glu Ala Glu Ala Glu Asp Ala Glu Phe Arg
    130                 135                 140

His Asp Ser Gly Tyr Glu Val His His Gln Lys Leu Val Phe Phe Ala
145                 150                 155                 160

Gly Asp Val Gly Ser Asn Lys Gly Ala Glu Ile Gly Leu Met Val Gly
                165                 170                 175

Gly Val Val Ile Ala Lys Arg Glu Ala Asp Ala Glu Ala Asp Ala Glu
            180                 185                 190

Phe Arg His Asp Ser Gly Tyr Glu Val His His Gln Lys Leu Val Phe
        195                 200                 205

Phe Ala Gly Asp Val Gly Ser Asn Lys Gly Ala Glu Ile Gly Leu Met
    210                 215                 220

Val Gly Gly Val Val Ile Ala Lys Arg Glu Ala Asp Ala Glu Ala Asp
225                 230                 235                 240

Ala Glu Phe Arg His Asp Ser Gly Tyr Glu Val His His Gln Lys Leu
                245                 250                 255

Val Phe Phe Ala Gly Asp Val Gly Ser Asn Lys Gly Ala Glu Ile Gly
            260                 265                 270

Leu Met Val Gly Gly Val Val Ile Ala
        275                 280
```

<210> SEQ ID NO 78
<211> LENGTH: 924
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78

```
gtcgactgga tccacaagtt tgtacaaaaa agcaggctgg taccaaaaga atgagattcc      60
catctatttt caccgctgtt ttgtttgctg cttcttctgc tttggctgct ccagttaaca     120
ctactactga agatgaaact gctcaaattc agctgaagc tgttattggt tacttggatt      180
tggaaggtga tttcgatgtt gctgttttgc cattctctaa ctctaccaac aatggtttgt     240
tgttcatcaa caccaccatt gcttctattg ctgctaaaga agaaggtgtc tctttggata     300
agagagaagc tgaagcagac gcagaattca gacatgattc tggttatgaa gttcaccacc     360
aaaagttggt tttcttcgct gatgttggtt ctaacaaggg tgctattatt ggtttgatgg     420
ttggtggtgt cgttattgct aaaagagaag ccgaagctga agctgatgcc gaattcagac     480
acgatagtgg ttacgaagta catcatcaaa aattagtctt tttcgccgat gtcggtagta     540
acaaaggtgc aatcataggt ttaatggtcg gtggtgtagt catagccaag agagaagcag     600
acgccgaagc cgatgcagaa ttcagacacg actccggtta cgaagtccat caccaaaagt     660 tggtatttt tgccgacgta ggttcaaaca aggtgccat aatcggttta atggttggtg      720
gtgtagtaat cgcaaaaaga gaagctgacg ctgaagcaga cgccgaattc agacacgact     780
caggttatga agtacaccat caaaaattgg tattctttgc tgacgttggt agtaacaagg     840
gtgccataat aggtttgatg gtcggtggtg tcgtaatcgc ttaaacccag ctttcttgta     900
caaagtggtg cggccgcact cgag                                            924
```

<210> SEQ ID NO 79
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Asp Ala Glu Phe Arg His Asp
                85                  90                  95

Ser Gly Tyr Glu Val His His Gln Lys Leu Val Phe Phe Ala Asp Val
            100                 105                 110

Gly Ser Asn Lys Gly Ala Ile Ile Gly Leu Met Val Gly Gly Val Val
        115                 120                 125

```
Ile Ala Lys Arg Glu Ala Glu Ala Asp Ala Glu Phe Arg His
    130                 135                 140

Asp Ser Gly Tyr Glu Val His His Gln Lys Leu Val Phe Phe Ala Asp
145                 150                 155                 160

Val Gly Ser Asn Lys Gly Ala Ile Ile Gly Leu Met Val Gly Gly Val
                165                 170                 175

Val Ile Ala Lys Arg Glu Ala Asp Ala Glu Ala Asp Ala Glu Phe Arg
            180                 185                 190

His Asp Ser Gly Tyr Glu Val His His Gln Lys Leu Val Phe Phe Ala
        195                 200                 205

Asp Val Gly Ser Asn Lys Gly Ala Ile Ile Gly Leu Met Val Gly Gly
    210                 215                 220

Val Val Ile Ala Lys Arg Glu Ala Asp Ala Glu Ala Asp Ala Glu Phe
225                 230                 235                 240

Arg His Asp Ser Gly Tyr Glu Val His His Gln Lys Leu Val Phe Phe
                245                 250                 255

Ala Asp Val Gly Ser Asn Lys Gly Ala Ile Ile Gly Leu Met Val Gly
            260                 265                 270

Gly Val Val Ile Ala
        275

<210> SEQ ID NO 80
<211> LENGTH: 936
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
gtcgactgga tccacaagtt tgtacaaaaa agcaggctgg taccaaaaga atgagattcc      60
catctatttt caccgctgtt ttgtttgctg cttcttctgc tttggctgct ccagttaaca     120
ctactactga agatgaaact gctcaaattc agctgaagc tgttattggt tacttggatt      180
tggaaggtga tttcgatgtt gctgttttgc cattctctaa ctctaccaac aatggttttgt    240 tgttcatcaa caccaccatt gcttctattg ctgctaaaga agaaggtgtc tctttggata     300
agagagaagc tgaagcagac gcagaattca gacatgattc tggttatgaa gttcaccacc    360
aaaagttggt tttcttcgct gaaatgtcg gttctaacaa gggtgctatt atcggtttga     420
tggttggtgg tgtagttatt gctaaagag aagccgaagc tgaagctgat gccgaattca    480
gacacgatag tggttacgaa gtacatcatc aaaaattagt cttttttcgcc gaaaacgttg    540 gtagtaacaa aggtgcaatc attggtttaa tggtcggtgg tgtcgtaata gccaagagag    600
aagcagacgc gaagccgat gcagaattca gacacgactc cggttacgaa gtccatcacc    660
aaaagttggt atttttttgcc gaaaacgttg gttcaaacaa gggtgccata ataggtttaa    720
tggttggtgg tgtcgttatc gcaaaaagag aagctgacgc agaagcagac gccgaattca    780
gacacgattc aggttacgaa gttcaccatc aaaaattggt attcttcgca gaaaacgttg    840
gttccaacaa aggtgctatt attggtttaa tggttggtgg tgtcgtcatt gcttaaaccc    900
agctttcttg tacaaagtgg tgcggccgca ctcgag                               936

<210> SEQ ID NO 81
<211> LENGTH: 281
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 81

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Asp Ala Glu Phe Arg His Asp
                85                  90                  95

Ser Gly Tyr Glu Val His His Gln Lys Leu Val Phe Phe Ala Glu Asn
            100                 105                 110

Val Gly Ser Asn Lys Gly Ala Ile Ile Gly Leu Met Val Gly Gly Val
        115                 120                 125

Val Ile Ala Lys Arg Glu Ala Glu Ala Glu Asp Ala Glu Phe Arg
    130                 135                 140

His Asp Ser Gly Tyr Glu Val His His Gln Lys Leu Val Phe Phe Ala
145                 150                 155                 160

Glu Asn Val Gly Ser Asn Lys Gly Ala Ile Ile Gly Leu Met Val Gly
                165                 170                 175

Gly Val Val Ile Ala Lys Arg Glu Ala Asp Ala Glu Ala Asp Ala Glu
            180                 185                 190

Phe Arg His Asp Ser Gly Tyr Glu Val His His Gln Lys Leu Val Phe
        195                 200                 205

Phe Ala Glu Asn Val Gly Ser Asn Lys Gly Ala Ile Ile Gly Leu Met
    210                 215                 220

Val Gly Gly Val Val Ile Ala Lys Arg Glu Ala Asp Ala Glu Ala Asp
225                 230                 235                 240

Ala Glu Phe Arg His Asp Ser Gly Tyr Glu Val His His Gln Lys Leu
                245                 250                 255

Val Phe Phe Ala Glu Asn Val Gly Ser Asn Lys Gly Ala Ile Ile Gly
            260                 265                 270

Leu Met Val Gly Gly Val Val Ile Ala
        275                 280

<210> SEQ ID NO 82
<211> LENGTH: 936
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 82
gtcgactgga tccacaagtt tgtacaaaaa agcaggctgg taccaaaaga atgagattcc     60
catctatttt caccgctgtt tgtttgctg cttcttctgc tttggctgct ccagttaaca    120
ctactactga agatgaaact gctcaaattc cagctgaagc tgttattggt tacttggatt    180
tggaaggtga tttcgatgtt gctgttttgc cattctctaa ctctaccaac aatggtttgt    240
tgttcatcaa caccaccatt gcttctattg ctgctaaaga agaaggtgtc tctttggata    300

```
agagagaagc tgaagcagac gcagaattca gacataattc tggttacgaa gttcaccacc    360
aaaagttggt ttttttcgct gaagatgtcg gttctaacaa gggtgctatt attggtttga    420
tggttggtgg tgtcgttatt gctaaaagag aagccgaagc tgaagctgat gccgaattca    480
gacacaatag tggttatgaa gtccatcatc aaaaattagt tttctttgcc gaagatgttg    540
gtagtaacaa aggtgcaatc atcggtttaa tggtcggtgg tgtagtaata gccaagagag    600
aagcagacgc cgaagccgat gcagaattca gacacaactc cggttatgaa gtacatcacc    660
aaaagttagt cttttttcgcc gaagatgttg gttcaaacaa aggtgccatt ataggtttaa    720
tggttggtgg tgtagttatc gctaagagag aagctgacgc tgaagcagac gccgaattca    780
gacacaactc aggttacgaa gtccaccatc aaaaattggt attcttcgca gaagatgtag    840
gtagtaacaa gggtgccata ataggtttga tggtcggtgg tgtcgtcata gcttaaaccc    900
agctttcttg tacaaagtgg tgcggccgca ctcgag                              936
```

<210> SEQ ID NO 83  
<211> LENGTH: 281  
<212> TYPE: PRT  
<213> ORGANISM: Artificial Sequence  
<220> FEATURE:  
<223> OTHER INFORMATION: Description of Artificial Sequence: Synthetic polypeptide

<400> SEQUENCE: 83

```
Met Arg Phe Pro Ser Ile Phe Thr Ala Val Leu Phe Ala Ala Ser Ser
1               5                  10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Asp Ala Glu Phe Arg His Asn
                85                  90                  95

Ser Gly Tyr Glu Val His His Gln Lys Leu Val Phe Phe Ala Glu Asp
            100                 105                 110

Val Gly Ser Asn Lys Gly Ala Ile Ile Gly Leu Met Val Gly Gly Val
        115                 120                 125

Val Ile Ala Lys Arg Glu Ala Glu Ala Glu Ala Asp Ala Glu Phe Arg
    130                 135                 140

His Asn Ser Gly Tyr Glu Val His His Gln Lys Leu Val Phe Phe Ala
145                 150                 155                 160

Glu Asp Val Gly Ser Asn Lys Gly Ala Ile Ile Gly Leu Met Val Gly
                165                 170                 175

Gly Val Val Ile Ala Lys Arg Glu Ala Asp Ala Glu Ala Asp Ala Glu
            180                 185                 190

Phe Arg His Asn Ser Gly Tyr Glu Val His His Gln Lys Leu Val Phe
        195                 200                 205

Phe Ala Glu Asp Val Gly Ser Asn Lys Gly Ala Ile Ile Gly Leu Met
    210                 215                 220

Val Gly Gly Val Val Ile Ala Lys Arg Glu Ala Asp Ala Glu Ala Asp
225                 230                 235                 240
```

```
Ala Glu Phe Arg His Asn Ser Gly Tyr Glu Val His His Gln Lys Leu
            245                 250                 255

Val Phe Phe Ala Glu Asp Val Gly Ser Asn Lys Gly Ala Ile Ile Gly
        260                 265                 270

Leu Met Val Gly Gly Val Val Ile Ala
        275                 280

<210> SEQ ID NO 84
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
acaagtttgt acaaaaaagc aggct                                           25

<210> SEQ ID NO 85
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Cys Cys Cys Ala Gly Cys Thr Thr Thr Cys Thr Thr Gly Thr Ala
1               5                   10                  15

Cys Ala Ala Ala Gly Thr Gly Gly Thr
            20                  25

<210> SEQ ID NO 86
<211> LENGTH: 184
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
caccatgctg ctgctgctgc tgctgctggg cctgaggcta cagctctccc tgggcgatgc        60
ggaatttcgc catgattctg gctatgaagt gcatcatcag aaactggtgt ttttgcgga       120 agatgtgggc tctaacaaag gcgcgattat tggcctgatg gtgggcggcg tggtgattgc       180
gtaa                                                                   184

<210> SEQ ID NO 87
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Leu Leu Leu Leu Leu Leu Leu Gly Leu Arg Leu Gln Leu Ser Leu
1               5                   10                  15

Gly Asp Ala Glu Phe Arg His Asp Ser Gly Tyr Glu Val His His Gln
            20                  25                  30

Lys Leu Val Phe Phe Ala Glu Asp Val Gly Ser Asn Lys Gly Ala Ile
        35                  40                  45

Ile Gly Leu Met Val Gly Gly Val Val Ile Ala
        50                  55
```

<210> SEQ ID NO 88
<211> LENGTH: 184
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
caccatggac atcaaggtgg tgttcaccct ggtgttcagc gccctggtgc aggccgatgc      60
ggaatttcgc catgattctg gctatgaagt gcatcatcag aaactggtgt tttttgcgga     120
agatgtgggc tctaacaaag gcgcgattat tggcctgatg gtgggcggcg tggtgattgc     180
gtaa                                                                  184

<210> SEQ ID NO 89
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Met Asp Ile Lys Val Val Phe Thr Leu Val Phe Ser Ala Leu Val Gln
1               5                   10                  15

Ala Asp Ala Glu Phe Arg His Asp Ser Gly Tyr Glu Val His His Gln
            20                  25                  30

Lys Leu Val Phe Phe Ala Glu Asp Val Gly Ser Asn Lys Gly Ala Ile
        35                  40                  45

Ile Gly Leu Met Val Gly Gly Val Val Ile Ala
    50                  55

<210> SEQ ID NO 90
<211> LENGTH: 184
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
caccatgctg cccggtttgg cactgctcct gctggccgcc tggacggctc gggcggatgc      60
ggaatttcgc catgattctg gctatgaagt gcatcatcag aaactggtgt tttttgcgga     120
agatgtgggc tctaacaaag gcgcgattat tggcctgatg gtgggcggcg tggtgattgc     180
gtaa                                                                  184

<210> SEQ ID NO 91
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Met Leu Pro Gly Leu Ala Leu Leu Leu Ala Ala Trp Thr Ala Arg
1               5                   10                  15

Ala Asp Ala Glu Phe Arg His Asp Ser Gly Tyr Glu Val His His Gln
            20                  25                  30

-continued

Lys Leu Val Phe Phe Ala Glu Asp Val Gly Ser Asn Lys Gly Ala Ile
         35                  40                  45

Ile Gly Leu Met Val Gly Gly Val Val Ile Ala
     50                  55

<210> SEQ ID NO 92
<211> LENGTH: 205
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
caccatggcc ctgtggatgc gcctcctgcc cctgctggcg ctgctggccc tctggggacc      60
tgacccagcc gcagccgatg cggaatttcg ccatgattct ggctatgaag tgcatcatca     120
gaaactggtg ttttttgcgg aagatgtggg ctctaacaaa ggcgcgatta ttggcctgat     180
ggtgggcggc gtggtgattg cgtaa                                            205

<210> SEQ ID NO 93
<211> LENGTH: 66
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Met Ala Leu Trp Met Arg Leu Leu Pro Leu Leu Ala Leu Leu Ala Leu
1               5                   10                  15

Trp Gly Pro Asp Pro Ala Ala Ala Asp Ala Glu Phe Arg His Asp Ser
            20                  25                  30

Gly Tyr Glu Val His His Gln Lys Leu Val Phe Phe Ala Glu Asp Val
         35                  40                  45

Gly Ser Asn Lys Gly Ala Ile Ile Gly Leu Met Val Gly Gly Val Val
     50                  55                  60

Ile Ala
65

<210> SEQ ID NO 94
<211> LENGTH: 178
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
caccatgtct gcacttctga tcctagctct tgttggagct gcagttgctg atgcggaatt      60
tcgccatgat tctggctatg aagtgcatca tcagaaactg gtgttttttg cggaagatgt     120
gggctctaac aaaggcgcga ttattggcct gatggtgggc ggcgtggtga ttgcgtaa      178

<210> SEQ ID NO 95
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

```
Met Ser Ala Leu Leu Ile Leu Ala Leu Val Gly Ala Ala Val Ala Asp
1               5                   10                  15

Ala Glu Phe Arg His Asp Ser Gly Tyr Glu Val His His Gln Lys Leu
            20                  25                  30

Val Phe Phe Ala Glu Asp Val Gly Ser Asn Lys Gly Ala Ile Ile Gly
        35                  40                  45

Leu Met Val Gly Gly Val Val Ile Ala
    50                  55
```

<210> SEQ ID NO 96
<211> LENGTH: 136
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 96

```
caccatggat gcggaattc gccatgattc tggctatgaa gtgcatcatc agaaactggt    60
gttttttgcg gaagatgtgg gctctaacaa aggcgcgatt attggcctga tggtgggcgg   120
cgtggtgatt gcgtaa                                                   136
```

<210> SEQ ID NO 97
<211> LENGTH: 43
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 97

```
Met Asp Ala Glu Phe Arg His Asp Ser Gly Tyr Glu Val His His Gln
1               5                   10                  15

Lys Leu Val Phe Phe Ala Glu Asp Val Gly Ser Asn Lys Gly Ala Ile
            20                  25                  30

Ile Gly Leu Met Val Gly Gly Val Val Ile Ala
        35                  40
```

<210> SEQ ID NO 98
<211> LENGTH: 199
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 98

```
caccatggcc ctgtggatgc gcctcctgcc cctgctggcg ctgctggccc tctggggacc    60
tgacccagcc gcagccgatg cggaatttcg ccatgattct ggctatgaag tgcatcatca   120
gaaactggtg ttttttgcgg aagatgtggg ctctaacaaa ggcgcgatta ttggcctgat   180
ggtgggcggc gtggtgtaa                                                199
```

<210> SEQ ID NO 99
<211> LENGTH: 64
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 99

```
Met Ala Leu Trp Met Arg Leu Leu Pro Leu Leu Ala Leu Leu Ala Leu
1               5                   10                  15

Trp Gly Pro Asp Pro Ala Ala Asp Ala Glu Phe Arg His Asp Ser
            20                  25                  30

Gly Tyr Glu Val His His Gln Lys Leu Val Phe Phe Ala Glu Asp Val
        35                  40                  45

Gly Ser Asn Lys Gly Ala Ile Ile Gly Leu Met Val Gly Gly Val Val
        50                  55                  60
```

<210> SEQ ID NO 100
<211> LENGTH: 948
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 100

```
gtcgactgga tccacaagtt tgtacaaaaa agcaggctgg taccaaaaga atgagattcc      60
catctatttt caccgctgtt ttgtttgctg cttcttctgc tttggctgct ccagttaaca    120
ctactactga agatgaaact gctcaaattc agctgaagc tgttattggt tacttggatt     180
tggaaggtga tttcgatgtt gctgttttgc cattctctaa ctctaccaac aatggtttgt    240
tgttcatcaa caccaccatt gcttctattg ctgctaaaga gaaggtgtc tctttggata     300
agagagaagc tgaagcagac gcagaattca gacatgattc tggttatgaa gttcaccacc    360
aaaagttggt ttcttcgct gaagatgttg gttctaacaa gggtgctatt atcggtttga     420
tggttggtgg tgtagttatt gctacaaaaa gagaagccga agctgaagct gatgccgaat    480
tcagacacga tagtggttac gaagtacatc atcaaaaatt agtcttttt gccgaagatg     540
tcggtagtaa caaaggtgca atcattggtt taatggtcgg tggtgtcgta atagcaacta    600
agagagaagc agacgccgaa gccgatgcag aattcagaca cgactccggt tacgaagtcc    660
atcaccaaaa gttggtattc tttgccgaag atgtcggttc aaacaagggt gccataatag    720
gtttaatggt tggtggtgtc gttatcgcta ccaagagaga agctgacgct gaagcagacg    780
ccgaattcag acacgactca ggttatgaag tacaccatca aaaattggta tttttcgcag    840
aagatgttgg ttccaacaaa ggtgccatta ttggtttgat ggttggtggt gtcgtcatag    900
ctacttaaac ccagctttct tgtacaaagt ggtgcggccg cactcgag                 948
```

<210> SEQ ID NO 101
<211> LENGTH: 285
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 101

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
        50                  55                  60
```

```
Phe Ile Asn Thr Thr Ile Ala Ser Ile Ala Ala Lys Glu Glu Gly Val
 65                  70                  75                  80

Ser Leu Asp Lys Arg Glu Ala Glu Ala Asp Ala Glu Phe Arg His Asp
                 85                  90                  95

Ser Gly Tyr Glu Val His His Gln Lys Leu Val Phe Phe Ala Glu Asp
            100                 105                 110

Val Gly Ser Asn Lys Gly Ala Ile Ile Gly Leu Met Val Gly Gly Val
        115                 120                 125

Val Ile Ala Thr Lys Arg Glu Ala Glu Ala Asp Ala Glu Phe
    130                 135                 140

Arg His Asp Ser Gly Tyr Glu Val His His Gln Lys Leu Val Phe Phe
145                 150                 155                 160

Ala Glu Asp Val Gly Ser Asn Lys Gly Ala Ile Ile Gly Leu Met Val
                165                 170                 175

Gly Gly Val Val Ile Ala Thr Lys Arg Glu Ala Asp Ala Glu Ala Asp
            180                 185                 190

Ala Glu Phe Arg His Asp Ser Gly Tyr Glu Val His His Gln Lys Leu
        195                 200                 205

Val Phe Phe Ala Glu Asp Val Gly Ser Asn Lys Gly Ala Ile Ile Gly
    210                 215                 220

Leu Met Val Gly Gly Val Val Ile Ala Thr Lys Arg Glu Ala Asp Ala
225                 230                 235                 240

Glu Ala Asp Ala Glu Phe Arg His Asp Ser Gly Tyr Glu Val His His
                245                 250                 255

Gln Lys Leu Val Phe Phe Ala Glu Asp Val Gly Ser Asn Lys Gly Ala
            260                 265                 270

Ile Ile Gly Leu Met Val Gly Gly Val Val Ile Ala Thr
        275                 280                 285

<210> SEQ ID NO 102
<211> LENGTH: 208
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
caccatggcc ctgtggatgc gcctcctgcc cctgctggcg ctgctggccc tctggggacc      60
tgacccagcc gcagccgatg cggaatttcg ccatgattct ggctatgaag tgcatcatca     120
gaaactggtg ttttttgcgg aagatgtggg ctctaacaaa ggcgcgatta ttggcctgat     180
ggtgggcggc gtggtgattg cgacataa                                        208

<210> SEQ ID NO 103
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Met Ala Leu Trp Met Arg Leu Leu Pro Leu Leu Ala Leu Leu Ala Leu
  1               5                  10                  15

Trp Gly Pro Asp Pro Ala Ala Ala Asp Ala Glu Phe Arg His Asp Ser
             20                  25                  30

Gly Tyr Glu Val His His Gln Lys Leu Val Phe Phe Ala Glu Asp Val
```

```
                35                  40                  45
Gly Ser Asn Lys Gly Ala Ile Ile Gly Leu Met Val Gly Val Val
    50                  55                  60

Ile Ala Thr
65

<210> SEQ ID NO 104
<211> LENGTH: 48
<212> TYPE: PRT
<213> ORGANISM: Homo sapiens

<400> SEQUENCE: 104

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr Val Ile Val Ile Thr
            35                  40                  45

<210> SEQ ID NO 105
<211> LENGTH: 49
<212> TYPE: PRT
<213> ORGANISM: Homo sapiens

<400> SEQUENCE: 105

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr Val Ile Val Ile Thr
            35                  40                  45

Leu
```